(12) United States Patent
Breitenkamp et al.

(10) Patent No.: US 7,618,944 B2
(45) Date of Patent: Nov. 17, 2009

(54) ENCAPSULATED AMYLOID-BETA PEPTIDES

(75) Inventors: Kurt Breitenkamp, Tampa, FL (US); Habib Skaff, Tampa, FL (US); Kevin N. Sill, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 0 days.

(21) Appl. No.: 12/040,774

(22) Filed: Feb. 29, 2008

(65) Prior Publication Data

US 2008/0274965 A1 Nov. 6, 2008

Related U.S. Application Data

(60) Provisional application No. 60/892,514, filed on Mar. 1, 2007, provisional application No. 60/917,000, filed on May 9, 2007.

(51) Int. Cl.
*A61K 38/17* (2006.01)
*A61K 38/08* (2006.01)
*A61K 38/10* (2006.01)

(52) U.S. Cl. ............... 514/12; 514/13; 514/15; 514/17; 514/772.3; 514/773

(58) Field of Classification Search ........................ None
See application file for complete search history.

(56) References Cited

U.S. PATENT DOCUMENTS

| | | | |
|---|---|---|---|
| 5,387,742 A | 2/1995 | Cordell | |
| 5,854,204 A | 12/1998 | Findeis et al. | |
| 6,455,308 B1 | 9/2002 | Freier | |
| 6,670,399 B2 | 12/2003 | Green et al. | |
| 6,761,888 B1 | 7/2004 | Schenk | |
| 6,875,434 B1 | 4/2005 | Schenk | |
| 6,890,535 B1 | 5/2005 | Schenk | |
| 6,905,686 B1 | 6/2005 | Schenk | |
| 6,972,127 B2 | 12/2005 | Schenk | |
| 7,060,671 B1 | 6/2006 | Stott | |
| 7,135,181 B2 | 11/2006 | Jensen et al. | |
| 7,179,892 B2 | 2/2007 | Basi et al. | |
| 7,189,819 B2 | 3/2007 | Basi et al. | |
| 7,479,550 B2 | 1/2009 | Rosenberg et al. | |
| 2003/0086938 A1 | 5/2003 | Jensen et al. | |
| 2003/0157117 A1 | 8/2003 | Rasmussen et al. | |
| 2004/0043935 A1 | 3/2004 | Frangione et al. | |
| 2005/0123553 A1 | 6/2005 | Monsonego et al. | |
| 2006/0135403 A1 | 6/2006 | Gervais et al. | |
| 2006/0142506 A1 | 6/2006 | Breitenkamp et al. | |
| 2006/0172914 A1 | 8/2006 | Breitenkamp et al. | |
| 2006/0240092 A1 | 10/2006 | Breitenkamp et al. | |
| 2007/0010435 A1 | 1/2007 | Frangione et al. | |
| 2007/0041945 A1 | 2/2007 | Jensen et al. | |
| 2007/0098721 A1 | 5/2007 | Hillen et al. | |
| 2007/0197452 A1 | 8/2007 | Mclaurin | |
| 2007/0218491 A1 | 9/2007 | Vasan et al. | |
| 2008/0207913 A1 | 8/2008 | Breitenkamp et al. | |

| | | |
|---|---|---|
| 2009/0092554 A1 | 4/2009 | Skaff et al. |

FOREIGN PATENT DOCUMENTS

| | | |
|---|---|---|
| WO | WO/01/62284 A2 | 8/2001 |
| WO | WO/03/015812 A2 | 2/2003 |
| WO | WO/2004/018997 A2 | 3/2004 |
| WO | WO/2004/024090 A2 | 3/2004 |
| WO | WO/2007/064917 A2 | 6/2007 |
| WO | WO/2008/098371 A1 | 8/2008 |

OTHER PUBLICATIONS

Bakar, N. K. A., et al., "The Chemical Speciation of Zinc in Human Saliva: Possible Correlation with Reduction of the Symptoms of the Common Cold Produced by Zinc Gluconate-Containing Lozenges", Chem. Spec. Bioavail. 1999, 11, 95-101.

Eby, G. A., "Zinc Ion Availability- the Determinant of Efficacy in Zinc Lozenge Treatment of Common Colds", J. Antimicrob. Chemo. 1997, 40, 483-493.

Cannan, R. K., et al, "Complex Formation Between Carboxylic Acids and Divalent Metal Cations", A. J. Am. Chem. Soc. 1938, 60, 2314-2320.

Kolb, H. C. et al., "In Situ Click Chemistry: Enzyme Inhibitors Made to Their Own Specifications", Chem. Int. Ed. 2001, 40, 2004-2021.

Wang, Q., et al., "Bioconjugation by Copper(1)-Catalyzed Azide-Alkyne [3+2] Cycloaddition", J. Am. Chem. Soc. 2003, 125, 3192-3193.

Link, A. J. et al., "Presentation and Detection of Azide Functionality in Bacterial Cell Surface Proteins", J. Am. Chem. Soc. 2004, 126, 10598-10602.

Deiters, A., et al., Adding Amino Acids with Novel Reactivity to the Genetic Code of Saccharomyces Cerevisiae, J. Am. Chem. Soc. 2003, 125, 11782-11783.

Allen, C., et al., "Nano-engineering Block Copolymer Aggregates for Drug Delivery", Colloid Surface B 1999, 16, 3-27.

Walsh, D. M. and D. J. Selkoe, "Deciphering the Molecular Basis of Memory Failure in Alzheimer's Disease", Neuron, 2004. 44(1): pp. 181-93.

Morgan, D., et al., "Aβ Peptide Vaccination Prevents Memory Loss in an Animal Model of Alzheimer's Disease", Nature, 2000. 408(6815): pp. 982-5.

Bard, F., et al., "Peripherally Administered Antibodies Against Amyloid β-Peptide Enter the Central Nervous System and Reduce Pathology in a Mouse Model of Alzheimer Disease", Nat Med, 2000. 6(8): pp. 916-9.

Dickey, C. A., et al., "Selectively Reduced Expression of Synaptic Plasticity-Related Genes in Amyloid Precursor Protein + Presenilin-1 Transgenic Mice", J Neurosci, 2003. 23(12): pp. 5219-26.

(Continued)

Primary Examiner—Cecilia Tsang
Assistant Examiner—Christina Bradley
(74) Attorney, Agent, or Firm—Andrea L. C. Robidoux; Choate Hall & Stewart LLP

(57) ABSTRACT

The present invention relates to the field of polymer chemistry and more particularly to encapsulated peptides and uses thereof.

10 Claims, 8 Drawing Sheets

OTHER PUBLICATIONS

Morgan, D., "Antibody Therapy for Alzheimer's Disease", Expert Rev Vaccines, 2003. 2(1): pp. 53-9.

Bayer, A. J., "Evaluation of the Safety and Immunogenicity of Synthetic Aβ42 (AN1792) in Patients with AD", et al., Neurology, 2005. 64(1): pp. 94-101.

Mathews, P. M., et al., "Setback for an Alzheimer's Disease Vaccine Lessons Learned", Neurology, 2003. 61(1): pp. 7-8.

Parihar, M. S., et al., "Alzheimer's Disease Pathogensis and Therapeutic Interventions", J Clin Neurosci, 2004. 11(5): pp. 456-67.

Kirkitadze, M. D., et al., "Paradigm Shifts in Alzheimer's Disease and Other Neurodegenerative Disorders: The Emerging Role of Oligomeric Assemblies", J Neurosci Res, 2002.69(5): pp. 567-77.

Chauhan, N. B., "Intracerebroventricular Passive Immunization With Anti-OligoAβ Antibody in TgCRND8", J Neurosci Res, 2007. 85(2): pp. 451-63.

Nilsson, L. N., et al., "Cognitive Impairment in PDAPP Mice Depends on ApoE and ACT-Catalyzed Amyloid Formation", Neurobiol Aging, 2004. 25(9): pp. 1153-67.

Zuliani, G., et al., "Plasma Cytokines Profile in Older Subjects With Late Onset Alzheimer's Disease or Vascular Dementia", J Psychiatr Res, 2007. 41(8): pp. 686-93.

Abbas, N., et al., "Up-Regulation of the Inflammatory Cytokines IFN-γ and IL-12 and Down-Regulation of IL-4 in Cerebral Cortex Regions of APP SWE Transgenic Mice", J Neuroimmunol, 2002. 126(1-2): pp. 50-7.

Antibody response to polymer encapsulated Aβ1-42 peptide

Cytokine response pre and post vaccination.

Anti-Aβ antibody response post vaccination by ELISA
Plate was coated with 50 μl wildtype Aβ1-35 peptide
at 10μg/ml.

Anti-Polymer antibody detection by ELISA, Polymer
were coated onto microplate with 50 μl at 40 μg/ml Immunostaining result of anti-sera in brain tissue from vaccination of APP/PS1 transgenic mouse

|  |  |  |  |
|---|---|---|---|
| 6E10 | PCTAD1 (Aβ1-25) | PCTAD2 (Aβ1-25+polymer) | PCTAD3 (Encapsulated Aβ1-25) |
|  | | | Immunostaining to APPPS1 mouse brain section with antisera from polymer encapsulated peptide vaccinated BALB/c mice |
| PCTAD4 (Aβ1-35) | PCTAD5(Aβ1-35+polymer) | PCTAD6 (Encapsulated Aβ1-35) | |

Western blot result of Aβ1-42 peptide at different aggregation conditions

SEQUENCE LISTING

<160> NUMBER OF SEQ ID NOS: 23

<210> SEQ ID NO 1
<211> LENGTH: 42
<212> TYPE: PRT
<213> ORGANISM: Artificial Sequence
<220> FEATURE:
<223> OTHER INFORMATION: Amyloid-beta peptide sequence -continued

```
<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 35
<212> TYPE: PRT
<213> ORGANISM: Artificial Sequence
<220> FEATURE:
<223> OTHER INFORMATION: Amyloid-beta peptide sequence

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met
        35

<210> SEQ ID NO 3
<211> LENGTH: 25
<212> TYPE: PRT
<213> ORGANISM: Artificial Sequence
<220> FEATURE:
<223> OTHER INFORMATION: Amyloid-beta peptide sequence

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly
            20                  25

<210> SEQ ID NO 4
<211> LENGTH: 16
<212> TYPE: PRT
<213> ORGANISM: Artificial Sequence
<220> FEATURE:
<223> OTHER INFORMATION: Amyloid-beta peptide sequence

<400> SEQUENCE: 4

Asp Ala Glu Phe Arg His Asp Ser Gly Tyr Glu Val His His Gln Lys
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Amyloid-beta peptide sequence

<400> SEQUENCE: 5

Gly Leu Met Val Gly Gly Val Val
1               5

<210> SEQ ID NO 6
<211> LENGTH: 10
<212> TYPE: PRT
<213> ORGANISM: Artificial Sequence
<220> FEATURE:
<223> OTHER INFORMATION: Amyloid-beta peptide sequence
```

-continued

```
<400> SEQUENCE: 6

Gly Leu Met Val Gly Gly Val Val Ile Ala
1               5                   10

<210> SEQ ID NO 7
<211> LENGTH: 42
<212> TYPE: PRT
<213> ORGANISM: Artificial Sequence
<220> FEATURE:
<223> OTHER INFORMATION: Amyloid-beta peptide sequence

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Cys His
        35                  40

<210> SEQ ID NO 8
<211> LENGTH: 42
<212> TYPE: PRT
<213> ORGANISM: Artificial Sequence
<220> FEATURE:
<223> OTHER INFORMATION: Amyloid-beta peptide sequence

<400> SEQUENCE: 8

Asp Ala Glu Phe Arg His Asp Ser Gly Tyr Glu Val His His Gln Lys
1               5                   10                  15

Leu Val Phe Phe Ala Trp Asp Met Gly Ser Asn Lys Gly Ala Ile Ile
            20                  25                  30

Gly Leu Met Val Gly Gly Val Val Ile Ala
        35                  40

<210> SEQ ID NO 9
<211> LENGTH: 35
<212> TYPE: PRT
<213> ORGANISM: Artificial Sequence
<220> FEATURE:
<223> OTHER INFORMATION: Amyloid-beta peptide sequence

<400> SEQUENCE: 9

Asp Ala Glu Phe Arg His Asp Ser Gly Tyr Glu Val His His Gln Lys
1               5                   10                  15

Leu Val Phe Phe Ala Trp Asp Met Gly Ser Asn Lys Gly Ala Ile Ile
            20                  25                  30

Gly Leu Met
        35

<210> SEQ ID NO 10
<211> LENGTH: 25
<212> TYPE: PRT
<213> ORGANISM: Artificial Sequence
<220> FEATURE:
<223> OTHER INFORMATION: Amyloid-beta peptide sequence

<400> SEQUENCE: 10

Asp Ala Glu Phe Arg His Asp Ser Gly Tyr Glu Val His His Gln Lys
1               5                   10                  15

Leu Val Phe Phe Ala Trp Asp Met Gly
            20                  25
```

```
<210> SEQ ID NO 11
<211> LENGTH: 42
<212> TYPE: PRT
<213> ORGANISM: Artificial Sequence
<220> FEATURE:
<223> OTHER INFORMATION: Amyloid-beta peptide sequence

<400> SEQUENCE: 11

Asp Ala Glu Phe Arg His Asp Ser Gly Tyr Glu Val His His Gln Lys
1               5                   10                  15

Leu Val Phe Phe Ala Trp Asp Val Gly Ser Asn Lys Gly Ala Ile Ile
            20                  25                  30

Gly Leu Met Val Gly Gly Val Val Ile Ala
        35                  40

<210> SEQ ID NO 12
<211> LENGTH: 35
<212> TYPE: PRT
<213> ORGANISM: Artificial Sequence
<220> FEATURE:
<223> OTHER INFORMATION: Amyloid-beta peptide sequence

<400> SEQUENCE: 12

Asp Ala Glu Phe Arg His Asp Ser Gly Tyr Glu Val His His Gln Lys
1               5                   10                  15

Leu Val Phe Phe Ala Trp Asp Val Gly Ser Asn Lys Gly Ala Ile Ile
            20                  25                  30

Gly Leu Met
        35

<210> SEQ ID NO 13
<211> LENGTH: 25
<212> TYPE: PRT
<213> ORGANISM: Artificial Sequence
<220> FEATURE:
<223> OTHER INFORMATION: Amyloid-beta peptide sequence

<400> SEQUENCE: 13

Asp Ala Glu Phe Arg His Asp Ser Gly Tyr Glu Val His His Gln Lys
1               5                   10                  15

Leu Val Phe Phe Ala Trp Asp Val Gly
            20                  25

<210> SEQ ID NO 14
<211> LENGTH: 42
<212> TYPE: PRT
<213> ORGANISM: Artificial Sequence
<220> FEATURE:
<223> OTHER INFORMATION: Amyloid-beta peptide sequence

<400> SEQUENCE: 14

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

Gly Leu Met Val Gly Gly Val Val Ile Ala
        35                  40

<210> SEQ ID NO 15
<211> LENGTH: 35
<212> TYPE: PRT
<213> ORGANISM: Artificial Sequence
<220> FEATURE:
<223> OTHER INFORMATION: Amyloid-beta peptide sequence
```

-continued

```
<400> SEQUENCE: 15

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

Gly Leu Met
        35

<210> SEQ ID NO 16
<211> LENGTH: 25
<212> TYPE: PRT
<213> ORGANISM: Artificial Sequence
<220> FEATURE:
<223> OTHER INFORMATION: Amyloid-beta peptide sequence

<400> SEQUENCE: 16

Asp Ala Glu Phe Arg His Asp Ser Gly Tyr Glu Val His His Gln Lys
1               5                   10                  15

Leu Val Phe Phe Ala Gln Asp Val Gly
            20                  25

<210> SEQ ID NO 17
<211> LENGTH: 42
<212> TYPE: PRT
<213> ORGANISM: Artificial Sequence
<220> FEATURE:
<223> OTHER INFORMATION: Amyloid-beta peptide sequence

<400> SEQUENCE: 17

Asp Ala Glu Phe Arg His Asp Ser Gly Tyr Glu Val His His Gln Lys
1               5                   10                  15

Leu Val Phe Phe Gly Gln Asp Val Gly Ser Asn Lys Gly Ala Ile Ile
            20                  25                  30

Gly Leu Met Val Gly Gly Val Val Ile Ala
        35                  40

<210> SEQ ID NO 18
<211> LENGTH: 35
<212> TYPE: PRT
<213> ORGANISM: Artificial Sequence
<220> FEATURE:
<223> OTHER INFORMATION: Amyloid-beta peptide sequence

<400> SEQUENCE: 18

Asp Ala Glu Phe Arg His Asp Ser Gly Tyr Glu Val His His Gln Lys
1               5                   10                  15

Leu Val Phe Phe Gly Gln Asp Val Gly Ser Asn Lys Gly Ala Ile Ile
            20                  25                  30

Gly Leu Met
        35

<210> SEQ ID NO 19
<211> LENGTH: 25
<212> TYPE: PRT
<213> ORGANISM: Artificial Sequence
<220> FEATURE:
<223> OTHER INFORMATION: Amyloid-beta peptide sequence
```

```
-continued

<400> SEQUENCE: 19

Asp Ala Glu Phe Arg His Asp Ser Gly Tyr Glu Val His His Gln Lys
1               5                   10                  15

Leu Val Phe Phe Gly Gln Asp Val Gly
            20                  25

<210> SEQ ID NO 20
<211> LENGTH: 35
<212> TYPE: PRT
<213> ORGANISM: Artificial Sequence
<220> FEATURE:
<223> OTHER INFORMATION: Amyloid-beta peptide sequence

<400> SEQUENCE: 20

Asp Ala Glu Phe Arg His Asp Asp Ala Glu Phe Arg His Asp Asp Ala
1               5                   10                  15

Glu Phe Arg His Asp Asp Ala Glu Phe Arg His Asp Asp Ala Glu Phe
            20                  25                  30

Arg His Asp
        35

<210> SEQ ID NO 21
<211> LENGTH: 10
<212> TYPE: PRT
<213> ORGANISM: Artificial Sequence
<220> FEATURE:
<223> OTHER INFORMATION: HIV Tat peptide sequence

<400> SEQUENCE: 21

Gly Arg Lys Lys Arg Arg Gln Arg Arg Arg
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Oligoarginine sequence

<400> SEQUENCE: 22

Arg Arg Arg Arg Arg Arg Arg Arg Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Oligohistidine sequence

<400> SEQUENCE: 23

His His His His His
1               5
```

US 7,618,944 B2

ENCAPSULATED AMYLOID-BETA PEPTIDES

CROSS-REFERENCE TO RELATED APPLICATIONS

The present application claims priority to U.S. provisional patent application Ser. No. 60/892,514, filed Mar. 1, 2007, and U.S. provisional patent application Ser. No. 60/917,000, filed May 9, 2007, the entirety of each of which is hereby incorporated herein by reference.

FIELD OF THE INVENTION

The present invention relates to the field of polymer chemistry and more particularly to encapsulated peptides and uses thereof.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs in response to the physiological environment encountered in diseased tissues, such as solid tumors.

Figure 1:
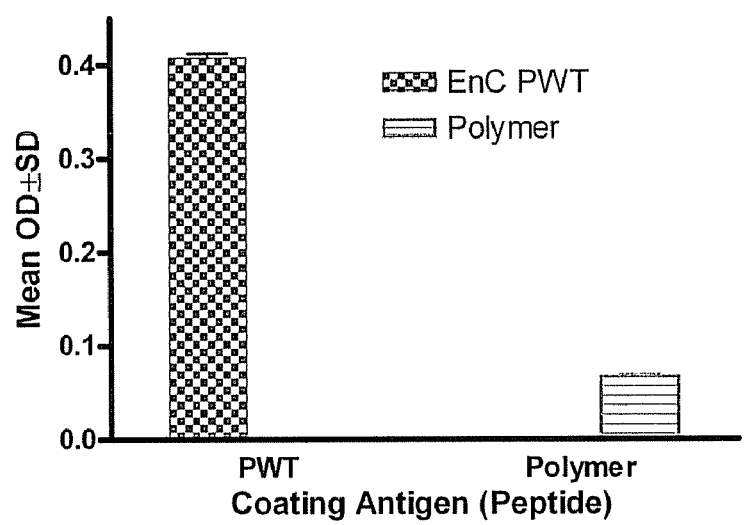
FIG. 1 depicts the ELISA result for antibody detection in sera resulting from administration of polymer encapsulated amyloid-beta (1-42) 10 days post-vaccination.

As used herein, the term "sequential polymerization", and variations thereof, refers to the method wherein, after a first monomer (e.g. NCA, lactam, or imide) is incorporated into the polymer, thus forming an amino acid "block", a second monomer (e.g. NCA, lactam, or imide) is added to the reaction to form a second amino acid block, which process may be continued in a similar fashion to introduce additional amino acid blocks into the resulting multi-block copolymers.

As used herein, the term "multiblock copolymer" refers to a polymer comprising at least two polymer portions, or "blocks". In certain embodiments, a multiblock copolymer is a diblock copolymer. In some embodiments, a multiblock copolymer is a diblock copolymer comprising one polymeric hydrophilic block and one polymeric hydrophobic block.

In certain embodiments, a multiblock copolymer of the present invention is a triblock copolymer. In some embodiments, a multiblock copolymer is a triblock copolymer comprising one synthetic polymer portion and two or more poly (amino acid) portions. In certain embodiments, multi-block copolymers include those having the format W-X'-X", wherein W is a synthetic polymer portion and X and X' are poly(amino acid) chains or "amino acid blocks". As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

In certain embodiments, the term "diblock copolymer" refers to a polymer comprising one synthetic hydrophilic polymer portion block and one synthetic hydrophobic polymer block.

In certain embodiments, the term "triblock copolymer" refers to a polymer comprising one synthetic polymer block and two poly(amino acid) blocks.

As used herein, the term "tetrablock copolymer" refers to a polymer comprising one synthetic polymer portion and either two poly(amino acid) portions, wherein 1 poly(amino acid) portion is a mixed block or a polymer comprising one synthetic polymer portion and three poly(amino acid) portions.

As used herein, the term "inner core" as it applies to a micelle of the present invention refers to the center of the micelle formed by the second (i.e., terminal) poly(amino acid) block. In accordance with the present invention, the inner core is not crosslinked. By way of illustration, in a triblock polymer of the format W-X'-X", as described above, the inner core corresponds to the X" block. It is contemplated that the X" block can be a mixed block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W-X'-X", as described above, the outer core corresponds to the X' block. It is contemplated that the X' block can be a mixed block. In certain embodiments, X" is a polymeric hydrophobic block.

As used herein, the term "crosslinkable" refers to a group which is capable of, or amenable to, crosslinking as described herein.

As used herein, the terms "drug-loaded" and "encapsulated", and derivatives thereof, are used interchangeably. In accordance with the present invention, a "drug-loaded" micelle refers to a micelle having a drug, or therapeutic agent, situated within the core of the micelle. This is also referred to as a drug, or therapeutic agent, being "encapsulated" within the micelle. In certain embodiments, the therapeutic agent is a wild-type or mutant amyloid-beta (1-42) peptide, or a fragment thereof.

As used herein, the term "amyloid-beta" is used interchangeably with "Aβ".

As used herein, the term "polymeric hydrophilic block" refers to a polymer that is not a poly(amino acid) and is hydrophilic in nature. Such hydrophilic polymers are well known in the art and include polyethyleneoxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxylethyl methacrylate), and derivatives thereof, and polymers of N-(2-hydroxypropyl)methacrylamide (HMPA) and derivatives thereof.

As used herein, the term "polymeric hydrophobic block" refers to a polymer that is hydrophobic in nature. Such hydrophobic polymers are well known in the art and include polyesters, poly(ortho esters), polyamides, poly(ester amides), polyanhydrides, polypropylene oxide, polybutylene oxide, poly(tetrahydrofuran), polystyrene, polybutadiene and derivatives thereof, poly(acrylates) and hydrophobic derivatives thereof, polymethacrylates and hydrophobic derivatives thereof, polyacrylamides and hydrophobic derivatives thereof, polymethacrylamides and hydrophobic derivatives thereof, and poly(amino acids). Exemplary polyesters include poly(δ-valerolactone), poly(ε-caprolactone), poly (lactide), poly(glycolide), poly(lactide-co-glycolide), poly (hydroxy alkanoates (e.g. poly(γ-hydroxybutyrate), poly(δ-hydroxyvalerate)), poly(β-malic acid), and derivatives thereof. Exemplary poly(amino acids) include poly(benzyl glutamate), poly(benzyl aspartate), poly(L-leucine-co-tyrosine), poly(D-leucine-co-tyrosine), poly(L-phenylalanine-co-tyrosine), poly(D-phenylalanine-co-tyrosine), poly(L-leucine-co-aspartic acid), poly(D-leucine-co-aspartic acid), poly(L-phenylalanine-co-aspartic acid), poly(D-phenylalanine-co-aspartic acid).

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit is in the L-configuration. Such poly(amino acids) include those having suitably protected functional groups. For example, amino acid monomers may have hydroxyl or amino moieties which are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In other embodiments, an amino acid block comprises one or more monomers such that the overall block is hydrophobic. In still other embodiments, amino acid blocks of the present invention include random amino acid blocks, ie blocks comprising a mixture of amino acid residues.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group.

As used herein, the term "D,L-mixed poly(amino acid) block" refers to a poly(amino acid) block wherein the poly (amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is the compound that reacts with an alkylene oxide to afford a polyalkylene oxide block. In other embodiments, the polymerization initiator is the amine salt described herein.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^+$)— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$°$; —(CH$_2$)$_{0-4}$OR$°$; —O—(CH$_2$)$_{0-4}$C(O)OR$°$; —(CH$_2$)$_{0-4}$CH(OR$°$)$_2$; —(CH$_2$)$_{0-4}$SR$°$; —(CH$_2$)$_{0-4}$Ph, which may be substituted with R$°$; —(CH$_2$)$_{0-4}$O(CH$_2$)$_{0-1}$Ph which may be substituted with R$°$; —CH=CHPh, which may be substituted with R$°$; —NO$_2$; —CN; —N$_3$; —(CH$_2$)$_{0-4}$N(R$°$)$_2$; —(CH$_2$)$_{0-4}$N(R$°$)C(O)R$°$; —N(R$°$)C(S)R$°$; —(CH$_2$)$_{0-4}$N(R$°$)C(O)NR$°_2$; —N(R$°$)C(S)NR$°_2$; —(CH$_2$)$_{0-4}$N(R$°$)C(O)OR$°$; —N(R$°$)N(R$°$)C(O)R$°$; —N(R$°$)N(R$°$)C(O)NR$°_2$; —N(R$°$)N(R$°$)C(O)OR$°$; —(CH$_2$)$_{0-4}$C(O)R$°$; —C(S)R$°$; —(CH$_2$)$_{0-4}$C(O)OR$°$; —(CH$_2$)$_{0-4}$C(O)SR$°$; —(CH$_2$)$_{0-4}$C(O)OSiR$°_3$; —(CH$_2$)$_{0-4}$OC(O)R$°$; —OC(O)(CH$_2$)$_{0-4}$SR—, SC(S)SR$°$; —(CH$_2$)$_{0-4}$SC(O)R$°$; —(CH$_2$)$_{0-4}$C(O)NR$°_2$; —C(S)NR$°_2$; —C(S)SR$°$; —SC(S)SR$°$, —(CH$_2$)$_{0-4}$OC(O)NR$°_2$; —C(O)N(OR$°$)R$°$; —C(O)C(O)R$°$;

—C(O)CH₂C(O)R°; —C(NOR°)R°; —(CH₂)₀₋₄SSR°; —(CH₂)₀₋₄S(O)₂R°; —(CH₂)₀₋₄S(O)₂OR°; —(CH₂)₀₋₄OS(O)₂R°; —S(O)₂NR°₂; —(CH₂)₀₋₄S(O)R°; —N(R°)S(O)₂NR°₂; —N(R°)S(O)₂R°; —N(OR°)R°; —C(NH)NR°₂; —P(O)₂R°; —P(O)R°₂; —OP(O)R°₂; —OP(O)(OR°)₂; SiR°₃; —(C₁₋₄ straight or branched alkylene)O—N(R°)₂; or —(C₁₋₄ straight or branched alkylene)C(O)O—N(R°)₂, wherein each R° may be substituted as defined below and is independently hydrogen, C₁₋₆ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH₂)₀₋₂R•, -(haloR•), —(CH₂)₀₋₂OH, —(CH₂)₀₋₂OR•, —(CH₂)₀₋₂CH(OR•)₂; —O(haloR•), —CN, —N₃, —(CH₂)₀₋₂C(O)R•, —(CH₂)₀₋₂C(O)OH, —(CH₂)₀₋₂C(O)OR•, —(CH₂)₀₋₂SR•, —(CH₂)₀₋₂SH, —(CH₂)₀₋₂NH₂, —(CH₂)₀₋₂NHR•, —(CH₂)₀₋₂NR•₂, —NO₂, —SiR•₃, —OSiR•₃, —C(O)SR•, —(C₁₋₄ straight or branched alkylene)C(O)OR•, or —SSR• wherein each R• is unsubstituted or where preceded by "halo" is substituted only with one or more halogens, and is independently selected from C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*₂, =NNHC(O)R*, =NNHC(O)OR*, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃O—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

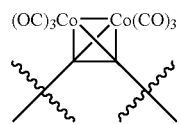

when depicted with the methylenes which bear it.

Suitable substituents on the aliphatic group of R* include halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable monoprotected amines further include, but are not limited to, aralkylamines, carbamates, allyl amines, amides, and the like.

Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —$CH_2CH_2O$—. Examples of crown ethers include 12-crown-4,15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

Other primary labels include those useful for positron emission tomography including molecules containing radioisotopes (e.g. $^{18}F$) or ligands with bound radioactive metals (e.g. $^{62}Cu$). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR , BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate", as used herein refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metallic or chemical coating, membranes (eg., nylon, polysulfone, silica), micro-beads (eg., latex, polystyrene, or other polymer), porous polymer matrices (eg., polyacrylamide gel, polysaccharide, polymethacrylate), macromolecular complexes (eg., protein, polysaccharide).

3. Description of Exemplary Embodiments

A. Multiblock Copolymers

As described generally above, in certain embodiments, the present invention provides a micelle having an amyloid-beta (1-42) peptide, or a fragment thereof, encapsulated therein, comprising a multiblock copolymer which comprises a polymeric hydrophilic block and a polymeric hydrophobic block.

In some embodiments, the present invention provides a micelle having an amyloid-beta (1-42) peptide, or a fragment thereof, encapsulated therein, comprising a multiblock copolymer which comprises a polymeric hydrophilic block, optionally a crosslinkable block, and a polymeric hydrophobic block.

One embodiment of the present invention provides a micelle having an amyloid-beta (1-42) peptide, or a fragment thereof, encapsulated therein, comprising a multiblock copolymer which comprises a polymeric hydrophilic block, optionally a poly(amino acid) block) that is optionally crosslinkable or crosslinked, and another poly(amino acid) block, characterized in that said micelle has an inner core, optionally a crosslinkable or crosslinked outer core, and a hydrophilic shell.

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the polymeric hydrophobic portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In some embodiments, these multiblock polymers comprise a poly(amino acid) block which optionally contains functionality suitable for crosslinking. It will be appreciated that this functionality is found on the corresponding amino acid side-chain.

In certain embodiments, the PEG block possesses a molecular weight of approx. 10,000 Da (225 repeat units) and contains at least one terminal amine hydrochloride salt used to initiate the synthesis of poly(amino acid) multi-block copolymers. In other embodiments, the PEG block possesses a molecular weight of approx. 12,000 Da (270 repeat units) and contains at least one terminal amine hydrochloride salt used to initiate the synthesis of poly(amino acid) multi-block copolymers. Without wishing to be bound by theory, it is believed that this particular PEG chain length imparts adequate water-solubility to the micelles and provides relatively long in vivo circulation times.

In certain embodiments, the present invention provides a micelle having an amyloid-beta (1-42) peptide, or a fragment thereof, encapsulated therein, wherein the micelle comprises a multiblock copolymer of formula I:

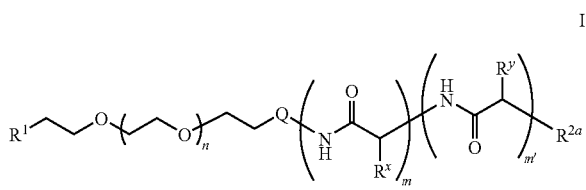

I wherein:
  n is 10-2500;
  m is 0 to 1000;
  m' is 1 to 1000;
  $R^x$ is a natural or unnatural amino acid side-chain group;
  $R^y$ is a hydrophobic or ionic, natural or unnatural amino acid side-chain group;
  $R^1$ is —Z(CH$_2$CH$_2$Y)$_p$(CH$_2$)$_t$R$^3$, wherein:
    Z is —O—, —S—, —C≡C—, or —CH$_2$—;
    each Y is independently —O— or —S—;
    p is 0-10;
    t is 0-10; and
    $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
  Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
    -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each R$^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the compound of formula I, as described above, has a polydispersity index ("PDI") of about 1.0 to about 1.2. According to another embodiment, the compound of formula I, as described above, has a polydispersity index ("PDI") of about 1.03 to about 1.15. According to yet another embodiment, the compound of formula I, as described above, has a polydispersity index ("PDI") of about 1.10 to about 1.20. According to other embodiments, the compound of formula I has a PDI of less than about 1.10.

As defined generally above, the n group of formula I is 10-2500. In certain embodiments, the present invention provides compounds of formula I, as described above, wherein n is about 225. In other embodiments, n is about 270. In other embodiments, n is about 350. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, 225±10, 275±10, 315±10, or 340±10

In certain embodiments, the m' group of formula I is about 5 to about 500. In certain embodiments, the m' group of formula I is about 10 to about 250. In other embodiments, m' is about 10 to about 50. According to yet another embodiment, m' is about 15 to about 40. In other embodiments, m' is about 20 to about 40. According to yet another embodiment, m' is about 50 to about 75. According to other embodiments, m and m' are independently about 10 to about 100. In certain embodiments, m is 5-50. In other embodiments, m is 5-25. In certain embodiments, m' is 5-50. In other embodiments, m' is 5-10. In other embodiments, m' is 10-20. In certain embodiments, m and m' add up to about 30 to about 60. In still other embodiments, m is 1-20 repeat units and m' is 10-50 repeat units.

In certain embodiments, the m group of formula I is zero, thereby forming a diblock copolymer.

In certain embodiments, the R$^3$ moiety of the R$^1$ group of formula I is —N$_3$.

In certain embodiments, the R$^3$ moiety of the R$^1$ group of formula I is —OCH$_3$.

In other embodiments, the R$^3$ moiety of the R$^1$ group of formula I is —CN.

In still other embodiments, the R$^3$ moiety of the R$^1$ group of formula I is a mono-protected amine or a di-protected amine.

In certain embodiments, the R$^3$ moiety of the R$^1$ group of formula I is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said R$^3$ moiety is an optionally substituted alkyl group. In other embodiments, said R$^3$ moiety is an optionally substituted alkynyl or alkenyl group. When said R$^3$ moiety is a substituted aliphatic group, suitable substituents on R$^3$ include CN, N$_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the R$^1$ group is 2-(N-methyl-N-(ethynylcarbonyl)amino)ethoxy, 4-ethynylbenzyloxy, or 2-(4-ethynylphenoxy)ethoxy.

In certain embodiments, the R$^3$ moiety of the R$^1$ group of formula I is an optionally substituted aryl group. Examples include optionally substituted phenyl and optionally substituted pyridyl. When said R$^3$ moiety is a substituted aryl group, suitable substituents on R$^3$ include CN, N$_3$, NO$_2$, —CH$_3$, —CH$_2$N$_3$, —CH═CH$_2$, —C≡CH, Br, I, F, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the R$^3$ moiety is an aryl group substituted with a suitably protected amino group. According to another aspect, the R$^3$ moiety is phenyl substituted with a suitably protected amino group.

In other embodiments, the R$^3$ moiety of the R$^1$ group of formula I is a protected hydroxyl group. In certain embodiments the protected hydroxyl of the R$^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the R$^3$ moiety of the R$^1$ group of formula I is a mono-protected or di-protected amino group. In certain embodiments R$^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula I is a protected aldehyde group. In certain embodiments the protected aldehydro moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl)acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula I is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiments, the $R^3$ moiety of the $R^1$ group of formula I is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodiments, $R^3$ is —S—S-pyridin-2-yl, —S—SBn, —S—SCH$_3$, or —S—S(p-ethynylbenzyl). In other embodiments, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula I is a crown ether. Examples of such crown ethers include 12-crown-4, 15-crown-5, and 18-crown-6.

In still other embodiments, the $R^3$ moiety of the $R^1$ group of formula I is a detectable moiety. According to one aspect of the invention, the $R^3$ moiety of the $R^1$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343. In certain embodiments, the $R^3$ moiety of the $R^1$ group of formula I is a detectable moiety selected from:

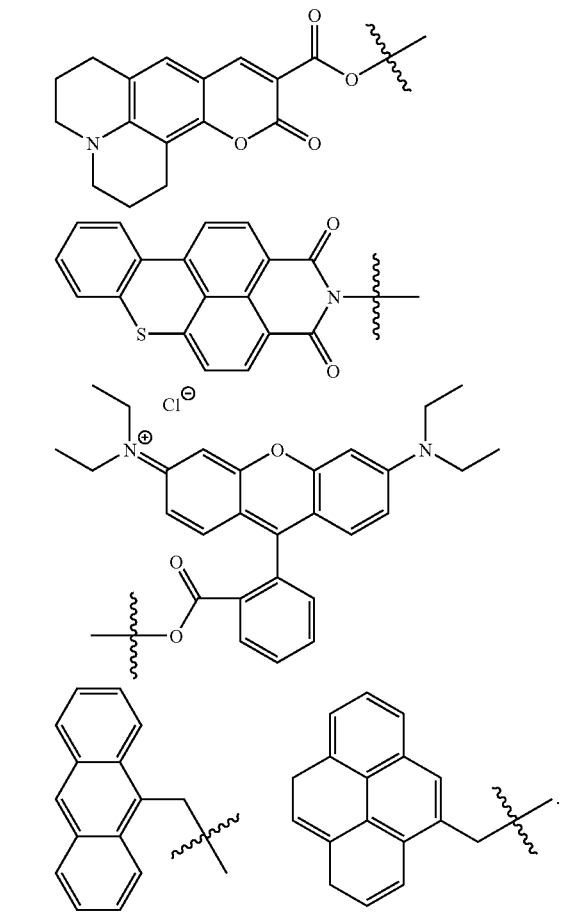

In certain embodiments, the $R^3$ moiety of the $R^1$ group of formula I is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula I having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula I to a macromolecule via Click chemistry. Yet another embodiment of the present invention provides a macromolecule conjugated to a compound of formula I via the $R^1$ group.

According to one embodiment, the $R^3$ moiety of the $R^1$ group of formula I is an azide-containing group. According to another embodiment, the $R^3$ moiety of the $R^1$ group of formula I is an alkyne-containing group. In certain embodiments, the $R^3$ moiety of the $R^1$ group of formula I has a terminal alkyne moiety. In other embodiments, $R^3$ moiety of the $R^1$ group of formula I is an alkyne moiety having an electron withdrawing group. Accordingly, in such embodiments, the $R^3$ moiety of the $R^1$ group of formula I is

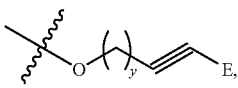

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula I is

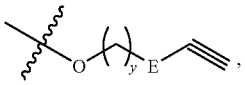

wherein E is an electron withdrawing group, such as a —C(O)O— group and y is 0-6.

As defined generally above, Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^x$ is an amino acid side-chain group and $R^y$ is a hydrophobic amino acid side-chain group. In other embodiments, $R^x$ is a crosslinkable amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. In other embodiments, $R^y$ is an ionic amino acid side-chain group. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, leucine/aspartic acid, phenylalanine/aspartic acid, and the like. According to another embodiment, $R^y$ is a hydrophobic amino acid side-chain group selected from phenylalanine, alanine, or leucine, and one or more of tyrosine, serine, or threonine.

In certain embodiments, $R^y$ forms a hydrophobic D,L-mixed poly(amino acid) block. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^x$ and $R^y$ are as described herein.

In other embodiments, $R^y$ consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include L-tyrosine and D-leucine, L-tyrosine and D-phenylalanine, L-serine and D-phenylalanine, L-aspartic acid and D-phenylalanine, L-glutamic acid and D-phenylalanine, L-tyrosine and D-benzyl glutamate, L-serine and D-benzyl glutamate, L-aspartic acid and D-benzyl glutamate, L-glutamic acid and D-benzyl glutamate, L-aspartic acid and D-leucine, and L-glutamic acid and D-leucine. Ratios (D-hydrophobic to L-hydrophilic) of such mixtures include any of 6:1, 5:1, 4:1, 3:1, 2:1, 1:1, 1:2, 1:3, 1:4; 1:5, and 1:6.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —$CH_2C(O)CH$, an aspartic acid side-chain, —$CH_2CH_2C(O)OH$, a cystein side-chain, —$CH_2SH$, a serine side-chain, —$CH_2OH$, an aldehyde containing side-chain, —$CH_2C(O)H$, a lysine side-chain, —$(CH_2)_4NH_2$, an arginine side-chain, —$(CH_2)_3NHC(=NH)NH_2$, a histidine side-chain, —$CH_2$-imidazol-4-yl.

As defined generally above, the $R^{2a}$ group of formula I is a mono-protected amine, a di-protected amine, —$NHR^4$, —$N(R^4)_2$, —$NHC(O)R^4$, —$NR^4C(O)R^4$, —$NHC(O)NHR^4$, —$NHC(O)N(R^4)_2$, —$NR^4C(O)NHR^4$, —$NR^4C(O)N(R^4)_2$, —$NHC(O)OR^4$, —$NR^4C(O)OR^4$, —$NHSO_2R^4$, or —$NR^4SO_2R^4$, wherein each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula I is —$NHC(O)R^4$, wherein $R^4$ is an optionally substituted aliphatic group. In other embodiments, the $R^{2a}$ group of formula I is —$NHC(O)Me$.

In certain embodiments, the $R^{2a}$ group of formula I is —$NHR^4$ or —$N(R^4)_2$ wherein each $R^4$ is hydrogen.

In certain embodiments, the $R^{2a}$ group of formula I is —$NHR^4$ or —$N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula I is —$NHR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^{2a}$ group of formula I is —$NHR^4$ wherein $R^4$ is an optionally substituted $C_{2-6}$ alkynyl group. Examples include —$CC\equiv CH$, —$CH_2C\equiv CH$, —$CH_2C\equiv CCH_3$, and —$CH_2CH_2C\equiv CH$.

In certain embodiments, the $R^{2a}$ group of formula I is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula I is —$NHR^4$ wherein $R^4$ is an optionally substituted phenyl ring. Suitable substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$(CH_2)_{0-4}SC(O)R^\circ$; —$(CH_2)_{0-4}C(O)NR^\circ_2$; —$C(S)NR^\circ_2$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; $SiR^\circ_3$; wherein each independent occurrence of $R^\circ$ is as defined herein supra. In other embodiments, the $R^{2a}$ group of formula I is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C\equiv CCH_3$, or —$CH_2C\equiv CH$.

In certain embodiments, the $R^{2a}$ group of formula I is —$NHR^4$ wherein $R^4$ is phenyl substituted with $N_3$, $N(R^\circ)_2$, $CO_2R^\circ$, or $C(O)R^\circ$ wherein each $R^\circ$ is independently as defined herein supra.

In certain embodiments, the $R^{2a}$ group of formula I is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula I is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula I is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In other embodiments, the present invention provides a micelle, having a beta-amlyoid (1-42) peptide, or a fragment thereof, encapsulated therein, comprising a multiblock copolymer of formula II:

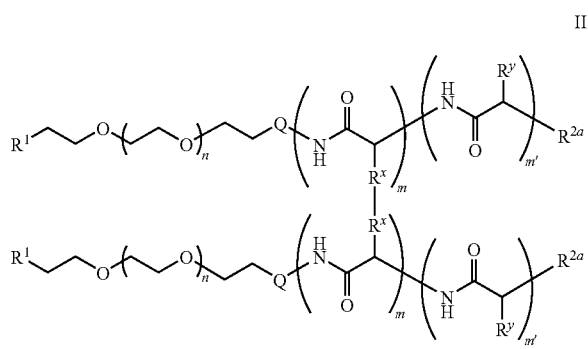

II wherein:
n is 10-2500;
m is 1 to 1000;
m' is 1 to 1000;
$R^x$ is a crosslinked natural or unnatural amino acid side-chain group;
$R^y$ is a hydrophobic or ionic, natural or unnatural, amino acid side-chain group;
$R^1$ is —Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the compound of formula II, as described above, has a polydispersity index ("PDI") of about 1.0 to about 1.2. According to another embodiment, the compound of formula II, as described above, has a polydispersity index ("PDI") of about 1.03 to about 1.15. According to yet another embodiment, the compound of formula II, as described above, has a polydispersity index ("PDI") of about 1.10 to about 1.20. According to other embodiments, the compound of formula II has a PDI of less than about 1.10.

As defined generally above, the n group of formula I is 10-2500. In certain embodiments, the present invention provides compounds of formula I, as described above, wherein n is about 225. In other embodiments, n is about 270. In other embodiments, n is about 350. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, 225±10, 275±10, 315±10, or 340±10

In certain embodiments, the m' group of formula II is about 5 to about 500. In certain embodiments, the m' group of formula II is about 10 to about 250. In other embodiments, m' is about 10 to about 50. In other embodiments, m' is about 20 to about 40. According to yet another embodiment, m' is about 50 to about 75. According to other embodiments, m and m' are independently about 10 to about 100. In certain embodiments, m' is 5-50. In other embodiments, m' is 5-10. In other embodiments, m' is 10-20. In certain embodiments, m and m' add up to about 30 to about 60. In still other embodiments, m is 1-20 repeat units and m' is 10-50 repeat units.

In certain embodiments, the $R^3$ moiety of the $R^1$ group of formula II is —N$_3$.

In certain embodiments, the $R^3$ moiety of the $R^1$ group of formula II is —$OCH_3$.

In other embodiments, the $R^3$ moiety of the $R^1$ group of formula II is —CN.

In still other embodiments, the $R^3$ moiety of the $R^1$ group of formula II is a mono-protected amine or a di-protected amine.

In certain embodiments, the $R^3$ moiety of the $R^1$ group of formula II is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula II is an optionally substituted aryl group. Examples include optionally substituted phenyl and optionally substituted pyridyl. When said $R^3$ moiety is a substituted aryl group, suitable substituents on $R^3$ include CN, $N_3$, $NO_2$, —$CH_3$, —$CH_2N_3$, —CH=$CH_2$, —C≡CH, Br, I, F, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the $R^3$ moiety is an aryl group substituted with a suitably protected amino group. According to another aspect, the $R^3$ moiety is phenyl substituted with a suitably protected amino group.

In other embodiments, the $R^3$ moiety of the $R^1$ group of formula II is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula II is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include di-benzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula II is a protected aldehyde group. In certain embodiments the protected aldehydro moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl)acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula II is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiment, the $R^3$ moiety of the $R^1$ group of formula II is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodiments, $R^3$ is —S—S-pyridin-2-yl, —S—SBn, —S—$SCH_3$, or —S—S(p-ethynylbenzyl). In other embodiments, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula II is a crown ether. Examples of such crown ethers include 12-crown-4, 15-crown-5, and 18-crown-6.

In still other embodiments, the $R^3$ moiety of the $R^1$ group of formula II is a detectable moiety. According to one aspect of the invention, the $R^3$ moiety of the $R^1$ group of formula II is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of formula II is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

In certain embodiments, the $R^3$ moiety of the $R^1$ group of formula II is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula II having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula II to a macromolecule via Click chemistry. Yet another embodiment of the present invention provides a macromolecule conjugated to a compound of formula II via the $R^1$ group.

According to one embodiment, the $R^3$ moiety of the $R^1$ group of formula II is an azide-containing group. According to another embodiment, the $R^3$ moiety of the $R^1$ group of formula II is an alkyne-containing group. In certain embodiments, the $R^3$ moiety of the $R^1$ group of formula II has a terminal alkyne moiety. In other embodiments, $R^3$ moiety of the $R^1$ group of formula II is an alkyne moiety having an electron withdrawing group. Accordingly, in such embodiments, the $R^3$ moiety of the $R^1$ group of formula II is

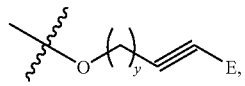

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula II is

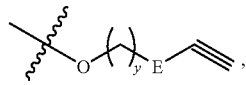

wherein E is an electron withdrawing group, such as a —C(O)O— group and y is 0-6.

As defined generally above, the Q group of formula II is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $R^x$ group of formula II is a crosslinked amino acid side-chain group and $R^y$ is a hydrophobic amino acid side-chain group. Such hydrophilic, or crosslinkable, amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, a suitably protected aspartic acid or glutamic acid side-chain, histidine or a suitably protected histidine side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^x$ and $R^y$ are as described herein.

In other embodiments, the $R^y$ group of formula II comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, leucine/aspartic acid, phenylalanine/aspartic acid, and the like. According to another embodiment, $R^y$ is a hydrophobic amino acid side-chain group selected from phenylalanine, alanine, or leucine, and one or more of tyrosine, serine, or threonine.

In certain embodiments, the $R^y$ group of formula II forms a hydrophobic D,L-mixed poly(amino acid) block. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^x$ and $R^y$ are as described herein.

In other embodiments, $R^y$ consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include L-tyrosine and D-leucine, L-tyrosine and D-phenylalanine, L-serine and D-phenylalanine, L-aspartic acid and D-phenylalanine, L-glutamic acid and D-phenylalanine, L-tyrosine and D-benzyl glutamate, L-serine and D-benzyl glutamate, L-aspartic acid and D-benzyl glutamate, L-glutamic acid and D-benzyl glutamate, L-aspartic acid and D-leucine, and L-glutamic acid and D-leucine. Ratios (D-hydrophobic to L-hydrophilic) of such mixtures include any of 6:1, 5:1, 4:1, 3:1, 2:1, 1:1, 1:2, 1:3, 1:4; 1:5, and 1:6.

As defined above, in certain embodiments, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH$_2$C(O)CH, an aspartic acid side-chain, —CH$_2$CH$_2$C(O)OH, a cystein side-chain, —CH$_2$SH, a serine side-chain, —CH$_2$OH, an aldehyde containing side-chain, —CH$_2$C(O)H, a lysine side-chain, —(CH$_2$)$_4$NH$_2$, an arginine side-chain, —(CH$_2$)$_3$NHC(=NH)NH$_2$, a histidine side-chain, —CH$_2$-imidazol-4-yl.

In other embodiments, $R^x$ comprises a mixture of hydrophilic amino acid side-chain groups. Such mixtures of amino acid side-chain groups include those having a carboxylic acid functionality, a hydroxyl functionality, a thiol functionality, and/or amine functionality. It will be appreciated that when $R^x$ comprises a mixture of hydrophilic amino acid side-chain functionalities, then multiple crosslinking can occur. For example, when $R^x$ comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of therapeutic drugs to the cytosol of diseased cells. When $R^x$ comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in drug release exclusively in the cytoplasm.

As defined generally above, the $R^{2a}$ group of formula II is a mono-protected amine, a di-protected amine, —NHR$^4$, —N(R$^4$)$_2$, —NHC(O)R$^4$, —NR$^4$C(O)R$^4$, —NHC(O)NHR$^4$, —NHC(O)N(R$^4$)$_2$, —NR$^4$C(O)NHR$^4$, —NR$^4$C(O)N(R$^4$)$_2$, —NHC(O)OR$^4$, —NR$^4$C(O)OR$^4$, —NHSO$_2$R$^4$, or —NR$^4$SO$_2$R$^4$, wherein each R$^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula II is —NHC(O)R$^4$, wherein R$^4$ is an optionally substituted aliphatic group. In other embodiments, the $R^{2a}$ group of formula II is —NHC(O)Me.

In certain embodiments, the $R^{2a}$ group of formula II is —NHR$^4$ or —N(R$^4$)$_2$ wherein each R$^4$ is hydrogen.

In certain embodiments, the $R^{2a}$ group of formula II is —NHR$^4$ or —N(R$^4$)$_2$ wherein each R$^4$ is an optionally substituted aliphatic group. One exemplary R$^4$ group is 5-norbornen-2-yl-methyl. According to yet another aspect of the present invention, the $R^{2a}$ group of formula II is —NHR$^4$ wherein R$^4$ is a C$_{1-6}$ aliphatic group substituted with N$_3$. Examples include —CH$_2$N$_3$. In some embodiments, R$^4$ is an optionally substituted C$_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^{2a}$ group of formula II is —$NHR^4$ wherein $R^4$ is an optionally substituted $C_{2-6}$ alkynyl group. Examples include —CC≡CH, —$CH_2$C≡CH, —$CH_2$C≡$CCH_3$, and —$CH_2CH_2$C≡CH.

In certain embodiments, the $R^{2a}$ group of formula II is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula II is —$NHR^4$ wherein $R^4$ is an optionally substituted phenyl ring. Suitable substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}$Ph, which may be substituted with $R^\circ$; —$(CH_2)_{0-4}O(CH_2)_{0-1}$Ph which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$(CH_2)_{0-4}SC(O)R^\circ$; —$(CH_2)_{0-4}C(O)NR^\circ_2$; —$C(S)NR^\circ_2$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; $SiR^\circ_3$; wherein each independent occurrence of $R^\circ$ is as defined herein supra. In other embodiments, the $R^{2a}$ group of formula II is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2$C≡$CCH_3$, or —$CH_2$C≡CH.

In certain embodiments, the $R^{2a}$ group of formula II is —$NHR^4$ wherein $R^4$ is phenyl substituted with $N_3$, $N(R^\circ)_2$, $CO_2R^\circ$, or $C(O)R^\circ$ wherein each $R^\circ$ is independently as defined herein supra.

In certain embodiments, the $R^{2a}$ group of formula II is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula II is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula II is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

Micelles of the present invention include exemplary compounds set forth in Tables 1 to 4, below. Table 1 sets forth exemplary compounds of the formula:

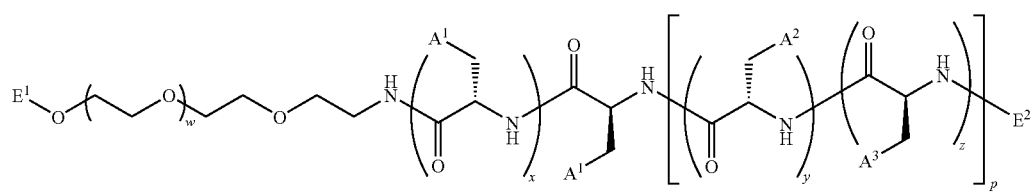

wherein each w is 25-1000, each x is 1-50, each y is 1-50, each z is 1-100, p is the sum of y and z, and each dotted bond represents the point of attachment to the rest of the molecule.

TABLE 1

| Compound | A¹ | A² | A³ | E¹ | E² |
|---|---|---|---|---|---|
| 1 | -C(=O)OH | phenyl | 4-hydroxyphenyl | -C≡CH | -C(=O)CH₃ |
| 2 | -C(=O)OH | phenyl | 4-hydroxyphenyl | N₃-CH₂CH₂- | -C(=O)CH₃ |
| 3 | -C(=O)OH | phenyl | 4-hydroxyphenyl | H₂N-CH₂CH₂- | -C(=O)CH₃ |
| 4 | -C(=O)OH | phenyl | 4-hydroxyphenyl | OHC-CH₂CH₂- | -C(=O)CH₃ |
| 5 | -C(=O)OH | phenyl | 4-hydroxyphenyl | -CH₃ | -C(=O)CH₃ |
| 6 | -C(=O)OH | phenyl | 4-hydroxyphenyl | N₃-CH₂CH₂- | -H |
| 7 | -C(=O)OH | phenyl | 4-hydroxyphenyl | H₂N-CH₂CH₂- | -H |
| 8 | -C(=O)OH | phenyl | 4-hydroxyphenyl | OHC-CH₂CH₂- | -H |
| 9 | -C(=O)OH | phenyl | 4-hydroxyphenyl | -C≡CH | -H |
| 10 | -C(=O)OH | phenyl | 4-hydroxyphenyl | -CH₃ | -H |
| 11 | -SH | phenyl | 4-hydroxyphenyl | -C≡CH | -C(=O)CH₃ |
| 12 | -SH | phenyl | 4-hydroxyphenyl | N₃-CH₂CH₂- | -C(=O)CH₃ |

TABLE 1-continued

| Compound | A¹ | A² | A³ | E¹ | E² |
|---|---|---|---|---|---|
| 13 | —SH | phenyl | 4-OH-phenyl | H₂N–CH₂CH₂– | –C(=O)CH₃ |
| 14 | —SH | phenyl | 4-OH-phenyl | OHC–CH₂CH₂– | –C(=O)CH₃ |
| 15 | —SH | phenyl | 4-OH-phenyl | H₃C– | –C(=O)CH₃ |
| 16 | —SH | phenyl | 4-OH-phenyl | N₃–CH₂CH₂– | –H |
| 17 | —SH | phenyl | 4-OH-phenyl | H₂N–CH₂CH₂– | –H |
| 18 | —SH | phenyl | 4-OH-phenyl | OHC–CH₂CH₂– | –H |
| 19 | —SH | phenyl | 4-OH-phenyl | HC≡C–CH₂– | –H |
| 20 | —SH | phenyl | 4-OH-phenyl | H₃C– | –H |
| 21 | –COOH | phenyl | –CH₂CH₂CH₂NH₂ | HC≡C–CH₂– | –C(=O)CH₃ |
| 22 | –COOH | phenyl | –CH₂CH₂CH₂NH₂ | N₃–CH₂CH₂– | –C(=O)CH₃ |
| 23 | –COOH | phenyl | –CH₂CH₂CH₂NH₂ | H₂N–CH₂CH₂– | –C(=O)CH₃ |
| 24 | –COOH | phenyl | –CH₂CH₂CH₂NH₂ | OHC–CH₂CH₂– | –C(=O)CH₃ |
| 25 | –COOH | phenyl | –CH₂CH₂CH₂NH₂ | H₃C– | –C(=O)CH₃ |

TABLE 1-continued

| Compound | A¹ | A² | A³ | E¹ | E² |
|---|---|---|---|---|---|
| 26 | -COOH | phenyl | -CH₂CH₂CH₂-NH₂ | N₃-CH₂CH₂- | -H |
| 27 | -COOH | phenyl | -CH₂CH₂CH₂-NH₂ | H₂N-CH₂CH₂- | -H |
| 28 | -COOH | phenyl | -CH₂CH₂CH₂-NH₂ | H(O=)C-CH₂CH₂- | -H |
| 29 | -COOH | phenyl | -CH₂CH₂CH₂-NH₂ | HC≡C-CH₂- | -H |
| 30 | -COOH | phenyl | -CH₂CH₂CH₂-NH₂ | H₃C- | -H |
| 31 | -SH | phenyl | -CH₂CH₂CH₂-NH₂ | HC≡C-CH₂- | -C(=O)CH₃ |
| 32 | -SH | phenyl | -CH₂CH₂CH₂-NH₂ | N₃-CH₂CH₂- | -C(=O)CH₃ |
| 33 | -SH | phenyl | -CH₂CH₂CH₂-NH₂ | H₂N-CH₂CH₂- | -C(=O)CH₃ |
| 34 | -SH | phenyl | -CH₂CH₂CH₂-NH₂ | H(O=)C-CH₂CH₂- | -C(=O)CH₃ |
| 35 | -SH | phenyl | -CH₂CH₂CH₂-NH₂ | H₃C- | -C(=O)CH₃ |
| 36 | -SH | phenyl | -CH₂CH₂CH₂-NH₂ | N₃-CH₂CH₂- | -H |
| 37 | -SH | phenyl | -CH₂CH₂CH₂-NH₂ | H₂N-CH₂CH₂- | -H |
| 38 | -SH | phenyl | -CH₂CH₂CH₂-NH₂ | H(O=)C-CH₂CH₂- | -H |
| 39 | -SH | phenyl | -CH₂CH₂CH₂-NH₂ | HC≡C-CH₂- | -H |

TABLE 1-continued

| Compound | A¹ | A² | A³ | E¹ | E² |
|---|---|---|---|---|---|
| 40 | —SH | phenyl | —CH₂CH₂CH₂NH₂ | H₃C— | —H |
| 41 | —CH₂C(=O)OH | phenyl | 4-hydroxyphenyl | HC≡C—CH₂— | —C(=O)CH₃ |
| 42 | —CH₂C(=O)OH | phenyl | 4-hydroxyphenyl | N₃CH₂CH₂— | —C(=O)CH₃ |
| 43 | —CH₂C(=O)OH | phenyl | 4-hydroxyphenyl | H₂NCH₂CH₂— | —C(=O)CH₃ |
| 44 | —CH₂C(=O)OH | phenyl | 4-hydroxyphenyl | OHC-CH₂CH₂— | —C(=O)CH₃ |
| 45 | —CH₂C(=O)OH | phenyl | 4-hydroxyphenyl | H₃C— | —C(=O)CH₃ |
| 46 | —CH₂C(=O)OH | phenyl | 4-hydroxyphenyl | N₃CH₂CH₂— | —H |
| 47 | —CH₂C(=O)OH | phenyl | 4-hydroxyphenyl | H₂NCH₂CH₂— | —H |
| 48 | —CH₂C(=O)OH | phenyl | 4-hydroxyphenyl | OHC-CH₂CH₂— | —H |
| 49 | —CH₂C(=O)OH | phenyl | 4-hydroxyphenyl | HC≡C—CH₂— | —H |
| 50 | —CH₂C(=O)OH | phenyl | 4-hydroxyphenyl | H₃C— | —H |
| 51 | —CH₂C(=O)OH | phenyl | —CH₂CH₂CH₂NH₂ | HC≡C—CH₂— | —C(=O)CH₃ |
| 52 | —CH₂C(=O)OH | phenyl | —CH₂CH₂CH₂NH₂ | N₃CH₂CH₂— | —C(=O)CH₃ |

TABLE 1-continued

| Compound | A¹ | A² | A³ | E¹ | E² |
|---|---|---|---|---|---|
| 53 | -CH₂-C(=O)-OH | phenyl | -(CH₂)₃-NH₂ | H₂N-CH₂CH₂- | -C(=O)-CH₃ |
| 54 | -CH₂-C(=O)-OH | phenyl | -(CH₂)₃-NH₂ | OHC-CH₂CH₂- | -C(=O)-CH₃ |
| 55 | -CH₂-C(=O)-OH | phenyl | -(CH₂)₃-NH₂ | H₃C- | -C(=O)-CH₃ |
| 56 | -CH₂-C(=O)-OH | phenyl | -(CH₂)₃-NH₂ | N₃-CH₂CH₂- | -H |
| 57 | -CH₂-C(=O)-OH | phenyl | -(CH₂)₃-NH₂ | H₂N-CH₂CH₂- | -H |
| 58 | -CH₂-C(=O)-OH | phenyl | -(CH₂)₃-NH₂ | OHC-CH₂CH₂- | -H |
| 59 | -CH₂-C(=O)-OH | phenyl | -(CH₂)₃-NH₂ | HC≡C-CH₂- | -H |
| 60 | -CH₂-C(=O)-OH | phenyl | -(CH₂)₃-NH₂ | H₃C- | -H |
| 61 | -C(=O)-OH | phenyl | -OH | HC≡C-CH₂- | -C(=O)-CH₃ |
| 62 | -C(=O)-OH | phenyl | -OH | N₃-CH₂CH₂- | -C(=O)-CH₃ |
| 63 | -C(=O)-OH | phenyl | -OH | H₂N-CH₂CH₂- | -C(=O)-CH₃ |
| 64 | -C(=O)-OH | phenyl | -OH | OHC-CH₂CH₂- | -C(=O)-CH₃ |
| 65 | -C(=O)-OH | phenyl | -OH | H₃C- | -C(=O)-CH₃ |
| 66 | -CH₂-C(=O)-OH | phenyl | -OH | HC≡C-CH₂- | -C(=O)-CH₃ |

TABLE 1-continued

| Compound | A¹ | A² | A³ | E¹ | E² |
|---|---|---|---|---|---|
| 67 | -CH₂-COOH | phenyl | -OH | N₃-CH₂CH₂- | -C(O)CH₃ |
| 68 | -CH₂-COOH | phenyl | -OH | H₂N-CH₂CH₂- | -C(O)CH₃ |
| 69 | -CH₂-COOH | phenyl | -OH | OHC-CH₂CH₂- | -C(O)CH₃ |
| 70 | -CH₂-COOH | phenyl | -OH | H₃C- | -C(O)CH₃ |
| 71 | -CH₂-COOH | phenyl | 1H-imidazol-4-yl | HC≡C-CH₂- | -C(O)CH₃ |
| 72 | -CH₂-COOH | phenyl | 1H-indol-2-yl | HC≡C-CH₂- | -C(O)CH₃ |
| 73 | -SH | phenyl | 1H-imidazol-4-yl | HC≡C-CH₂- | -C(O)CH₃ |
| 74 | -SH | phenyl | 1H-indol-2-yl | HC≡C-CH₂- | -C(O)CH₃ |
| 75 | -CH₂CH₂-NH₂ | phenyl | 4-hydroxyphenyl | HC≡C-CH₂- | -C(O)CH₃ |
| 76 | -CH₂CH₂-NH₂ | phenyl | 4-hydroxyphenyl | N₃-CH₂CH₂- | -C(O)CH₃ |
| 77 | -CH₂CH₂-NH₂ | phenyl | 4-hydroxyphenyl | H₂N-CH₂CH₂- | -C(O)CH₃ |
| 78 | -CH₂CH₂-NH₂ | phenyl | 4-hydroxyphenyl | OHC-CH₂CH₂- | -C(O)CH₃ |
| 79 | -CH₂CH₂-NH₂ | phenyl | 4-hydroxyphenyl | H₃C- | -C(O)CH₃ |

TABLE 1-continued

| Compound | A¹ | A² | A³ | E¹ | E² |
|---|---|---|---|---|---|
| 80 | propylamine | phenyl | 4-hydroxyphenyl | azidoethyl | H |
| 81 | propylamine | phenyl | 4-hydroxyphenyl | aminoethyl | H |
| 82 | propylamine | phenyl | 4-hydroxyphenyl | 3-oxopropyl | H |
| 83 | propylamine | phenyl | 4-hydroxyphenyl | propynyl | H |
| 84 | propylamine | phenyl | 4-hydroxyphenyl | methyl | H |
| 85 | 1H-imidazol-4-yl | phenyl | 4-hydroxyphenyl | propynyl | acetyl |
| 86 | 1H-imidazol-4-yl | phenyl | 4-hydroxyphenyl | azidoethyl | acetyl |
| 87 | 1H-imidazol-4-yl | phenyl | 4-hydroxyphenyl | aminoethyl | acetyl |
| 88 | 1H-imidazol-4-yl | phenyl | 4-hydroxyphenyl | 3-oxopropyl | acetyl |
| 89 | 1H-imidazol-4-yl | phenyl | 4-hydroxyphenyl | methyl | acetyl |
| 90 | 1H-imidazol-4-yl | phenyl | 4-hydroxyphenyl | azidoethyl | H |
| 91 | 1H-imidazol-4-yl | phenyl | 4-hydroxyphenyl | aminoethyl | H |
| 92 | 1H-imidazol-4-yl | phenyl | 4-hydroxyphenyl | 3-oxopropyl | H |

TABLE 1-continued

| Compound | A¹ | A² | A³ | E¹ | E² |
|---|---|---|---|---|---|
| 93 | imidazole | phenyl | 4-hydroxyphenyl | HC≡C–CH₂– | H |
| 94 | imidazole | phenyl | 4-hydroxyphenyl | H₃C– | H |
| 95 | –CH(COOH)– | phenyl | 4-hydroxyphenyl | HS–CH₂CH₂– | acetyl |
| 96 | –CH₂C(O)OH | phenyl | 4-hydroxyphenyl | HS–CH₂CH₂– | acetyl |
| 97 | imidazole | phenyl | 4-hydroxyphenyl | HS–CH₂CH₂– | acetyl |
| 98 | indole | phenyl | 4-hydroxyphenyl | HS–CH₂CH₂– | acetyl |

Table 2 sets forth exemplary compounds of the formula:

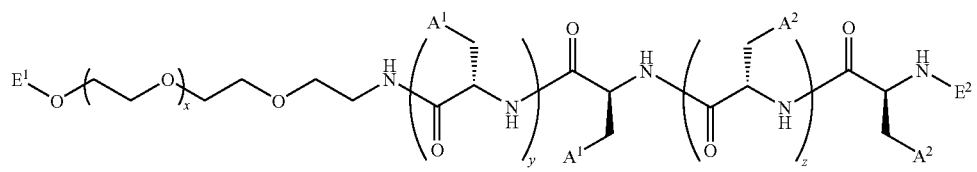

wherein each x is 100-500, each y is 4-20, each z is 5-50, and each dotted bond represents the point of attachment to the rest of the molecule.

TABLE 2

| Compound | A¹ | A² | E¹ | E² |
|---|---|---|---|---|
| 99 | –C(O)OH | phenyl | HC≡C–CH₂– | acetyl |
| 100 | –C(O)OH | –C(O)O–CH₂–phenyl | HC≡C–CH₂– | acetyl |

TABLE 2-continued

| Compound | A¹ | A² | E¹ | E² |
|---|---|---|---|---|
| 101 | -COOH | -CH₂C(O)O-CH₂-Ph | alkyne | acetyl |
| 102 | -COOH | -(CH₂)₃-NH₂ | alkyne | acetyl |
| 103 | -COOH | imidazole | alkyne | acetyl |
| 104 | -COOH | 1H-indol-2-yl | alkyne | acetyl |
| 105 | -CH₂C(O)OH | phenyl | alkyne | acetyl |
| 106 | -CH₂C(O)OH | -CH₂C(O)O-CH₂-Ph | alkyne | acetyl |
| 107 | -CH₂C(O)OH | -CH₂C(O)O-CH₂-Ph | alkyne | acetyl |
| 108 | -CH₂C(O)OH | -(CH₂)₃-NH₂ | alkyne | acetyl |
| 109 | -CH₂C(O)OH | imidazole | alkyne | acetyl |
| 110 | -CH₂C(O)OH | 1H-indol-2-yl | alkyne | acetyl |
| 111 | -SH | phenyl | alkyne | acetyl |
| 112 | -SH | -CH₂C(O)O-CH₂-Ph | alkyne | acetyl |

TABLE 2-continued

| Compound | A¹ | A² | E¹ | E² |
|---|---|---|---|---|
| 113 | –SH | –CH₂C(O)OCH₂-phenyl | –C≡CH | –C(O)CH₃ |
| 114 | –SH | –(CH₂)₃NH₂ | –C≡CH | –C(O)CH₃ |
| 115 | –SH | imidazol-4-yl | –C≡CH | –C(O)CH₃ |
| 116 | –SH | 1H-indol-2-yl | –C≡CH | –C(O)CH₃ |
| 117 | –C(O)OH | phenyl | H₂N–CH₂CH₂– | –C(O)CH₃ |
| 118 | –C(O)OH | –C(O)OCH₂-phenyl | H₂N–CH₂CH₂– | –C(O)CH₃ |
| 119 | –C(O)OH | –CH₂C(O)OCH₂-phenyl | H₂N–CH₂CH₂– | –C(O)CH₃ |
| 120 | –C(O)OH | –(CH₂)₃NH₂ | H₂N–CH₂CH₂– | –C(O)CH₃ |
| 121 | –C(O)OH | imidazol-4-yl | H₂N–CH₂CH₂– | –C(O)CH₃ |
| 122 | –C(O)OH | 1H-indol-2-yl | H₂N–CH₂CH₂– | –C(O)CH₃ |
| 123 | –CH₂C(O)OH | phenyl | H₂N–CH₂CH₂– | –C(O)CH₃ |
| 124 | –CH₂C(O)OH | –C(O)OCH₂-phenyl | H₂N–CH₂CH₂– | –C(O)CH₃ |

TABLE 2-continued

| Compound | A¹ | A² | E¹ | E² |
|---|---|---|---|---|
| 125 | -CH₂-COOH | -CH₂-C(O)O-CH₂-C₆H₅ | H₂N-CH₂CH₂- | -C(O)-CH₃ |
| 126 | -CH₂-COOH | -CH₂CH₂CH₂-NH₂ | H₂N-CH₂CH₂- | -C(O)-CH₃ |
| 127 | -CH₂-COOH | -CH₂-(1H-imidazol-4-yl) | H₂N-CH₂CH₂- | -C(O)-CH₃ |
| 128 | -CH₂-COOH | -(1H-indol-2-yl) | H₂N-CH₂CH₂- | -C(O)-CH₃ |
| 129 | -SH | -C₆H₅ | H₂N-CH₂CH₂- | -C(O)-CH₃ |
| 130 | -SH | -C(O)O-CH₂-C₆H₅ | H₂N-CH₂CH₂- | -C(O)-CH₃ |
| 131 | -SH | -CH₂-C(O)O-CH₂-C₆H₅ | H₂N-CH₂CH₂- | -C(O)-CH₃ |
| 132 | -SH | -CH₂CH₂CH₂-NH₂ | H₂N-CH₂CH₂- | -C(O)-CH₃ |
| 133 | -SH | -CH₂-(1H-imidazol-4-yl) | H₂N-CH₂CH₂- | -C(O)-CH₃ |
| 134 | -SH | -(1H-indol-2-yl) | H₂N-CH₂CH₂- | -C(O)-CH₃ |
| 135 | -COOH | -C₆H₅ | N₃-CH₂CH₂- | -C(O)-CH₃ |
| 136 | -COOH | -CH₂-C(O)O-CH₂-C₆H₅ | N₃-CH₂CH₂- | -C(O)-CH₃ |

TABLE 2-continued

| Compound | A¹ | A² | E¹ | E² |
|---|---|---|---|---|
| 137 | -COOH | -C(O)O-CH₂-C₆H₅ | N₃-CH₂CH₂CH₂- | -C(O)CH₃ |
| 138 | -COOH | -CH₂CH₂CH₂-NH₂ | N₃-CH₂CH₂CH₂- | -C(O)CH₃ |
| 139 | -COOH | -(1H-imidazol-4-yl) | N₃-CH₂CH₂CH₂- | -C(O)CH₃ |
| 140 | -COOH | -(1H-indol-2-yl) | N₃-CH₂CH₂CH₂- | -C(O)CH₃ |
| 141 | -CH₂-COOH | -C₆H₅ | N₃-CH₂CH₂CH₂- | -C(O)CH₃ |
| 142 | -CH₂-COOH | -C(O)O-CH₂-C₆H₅ | N₃-CH₂CH₂CH₂- | -C(O)CH₃ |
| 143 | -CH₂-COOH | -C(O)O-CH₂-C₆H₅ | N₃-CH₂CH₂CH₂- | -C(O)CH₃ |
| 144 | -CH₂-COOH | -CH₂CH₂CH₂-NH₂ | N₃-CH₂CH₂CH₂- | -C(O)CH₃ |
| 145 | -CH₂-COOH | -(1H-imidazol-4-yl) | N₃-CH₂CH₂CH₂- | -C(O)CH₃ |
| 146 | -CH₂-COOH | -(1H-indol-2-yl) | N₃-CH₂CH₂CH₂- | -C(O)CH₃ |
| 147 | -SH | -C₆H₅ | N₃-CH₂CH₂CH₂- | -C(O)CH₃ |
| 148 | -SH | -C(O)O-CH₂-C₆H₅ | N₃-CH₂CH₂CH₂- | -C(O)CH₃ |

TABLE 2-continued

| Compound | A¹ | A² | E¹ | E² |
|---|---|---|---|---|
| 149 | SH | benzyl ester -CH2C(O)OCH2-phenyl | N3-CH2CH2- | -C(O)CH3 |
| 150 | SH | -CH2CH2CH2NH2 | N3-CH2CH2- | -C(O)CH3 |
| 151 | SH | 1H-imidazol-4-yl | N3-CH2CH2- | -C(O)CH3 |
| 152 | SH | 1H-indol-2-yl | N3-CH2CH2- | -C(O)CH3 |
| 153 | 1H-imidazol-4-yl | phenyl | HC≡C-CH2- | -C(O)CH3 |
| 154 | 1H-imidazol-4-yl | benzyl ester -C(O)OCH2-phenyl | HC≡C-CH2- | -C(O)CH3 |
| 155 | 1H-imidazol-4-yl | benzyl ester -CH2C(O)OCH2-phenyl | HC≡C-CH2- | -C(O)CH3 |
| 156 | 1H-imidazol-4-yl | -CH2CH2CH2NH2 | HC≡C-CH2- | -C(O)CH3 |
| 157 | 1H-imidazol-4-yl | phenyl | N3-CH2CH2- | -C(O)CH3 |
| 158 | 1H-imidazol-4-yl | benzyl ester -C(O)OCH2-phenyl | N3-CH2CH2- | -C(O)CH3 |
| 159 | 1H-imidazol-4-yl | benzyl ester -CH2C(O)OCH2-phenyl | N3-CH2CH2- | -C(O)CH3 |
| 160 | 1H-imidazol-4-yl | -CH2CH2CH2NH2 | N3-CH2CH2- | -C(O)CH3 |

TABLE 2-continued

| Compound | A¹ | A² | E¹ | E² |
|---|---|---|---|---|
| 161 | -COOH | phenyl | HS-CH2CH2- | -C(O)CH3 |
| 162 | -COOH | -C(O)O-CH2-phenyl | HS-CH2CH2- | -C(O)CH3 |
| 163 | -COOH | -CH2-C(O)O-CH2-phenyl | HS-CH2CH2- | -C(O)CH3 |
| 164 | -COOH | -CH2CH2CH2-NH2 | HS-CH2CH2- | -C(O)CH3 |
| 165 | -COOH | 1H-imidazol-4-yl | HS-CH2CH2- | -C(O)CH3 |
| 166 | -COOH | 1H-indol-2-yl | HS-CH2CH2- | -C(O)CH3 |
| 167 | -CH2-COOH | phenyl | HS-CH2CH2- | -C(O)CH3 |
| 168 | -CH2-COOH | -C(O)O-CH2-phenyl | HS-CH2CH2- | -C(O)CH3 |
| 169 | -CH2-COOH | -CH2-C(O)O-CH2-phenyl | HS-CH2CH2- | -C(O)CH3 |
| 170 | -CH2-COOH | -CH2CH2CH2-NH2 | HS-CH2CH2- | -C(O)CH3 |
| 171 | -CH2-COOH | 1H-imidazol-4-yl | HS-CH2CH2- | -C(O)CH3 |
| 172 | -CH2-COOH | 1H-indol-2-yl | HS-CH2CH2- | -C(O)CH3 |

TABLE 2-continued

| Compound | A¹ | A² | E¹ | E² |
|---|---|---|---|---|
| 173 | ~NH₂ | phenyl | HS~ | C(=O)CH₃ |
| 174 | ~NH₂ | benzyl ester (–C(=O)O–CH₂–Ph) | HS~ | C(=O)CH₃ |
| 175 | ~NH₂ | –CH₂–C(=O)O–CH₂–Ph | HS~ | C(=O)CH₃ |
| 176 | ~NH₂ | 1H-imidazol-4-yl | HS~ | C(=O)CH₃ |
| 177 | ~NH₂ | 1H-indol-2-yl | HS~ | C(=O)CH₃ |
| 178 | ~NH₂ | phenyl | HC≡C~ | C(=O)CH₃ |
| 179 | ~NH₂ | benzyl ester (–C(=O)O–CH₂–Ph) | HC≡C~ | C(=O)CH₃ |
| 180 | ~NH₂ | –CH₂–C(=O)O–CH₂–Ph | HC≡C~ | C(=O)CH₃ |
| 181 | ~NH₂ | 1H-imidazol-4-yl | HC≡C~ | C(=O)CH₃ |
| 182 | ~NH₂ | 1H-indol-2-yl | HC≡C~ | C(=O)CH₃ |
| 183 | ~NH₂ | phenyl | N₃~ | C(=O)CH₃ |
| 184 | ~NH₂ | benzyl ester (–C(=O)O–CH₂–Ph) | N₃~ | C(=O)CH₃ |

TABLE 2-continued

| Compound | A¹ | A² | E¹ | E² |
|---|---|---|---|---|
| 185 | ~~~NH₂ | benzyl ester -CH₂C(O)OCH₂Ph | N₃~~~ | -C(O)CH₃ |
| 186 | ~~~NH₂ | 4-imidazolyl | N₃~~~ | -C(O)CH₃ |
| 187 | ~~~NH₂ | 2-indolyl | N₃~~~ | -C(O)CH₃ |
| 188 | ~~~NH₂ | phenyl | H-C(O)CH₂CH₂~~~ | -C(O)CH₃ |
| 189 | ~~~NH₂ | -CH₂OC(O)Ph (benzyloxycarbonyl) | H-C(O)CH₂CH₂~~~ | -C(O)CH₃ |
| 190 | ~~~NH₂ | -CH₂C(O)OCH₂Ph | H-C(O)CH₂CH₂~~~ | -C(O)CH₃ |
| 191 | ~~~NH₂ | 4-imidazolyl | H-C(O)CH₂CH₂~~~ | -C(O)CH₃ |
| 192 | ~~~NH₂ | 2-indolyl | H-C(O)CH₂CH₂~~~ | -C(O)CH₃ |

Table 3 sets forth exemplary compounds of the formula:

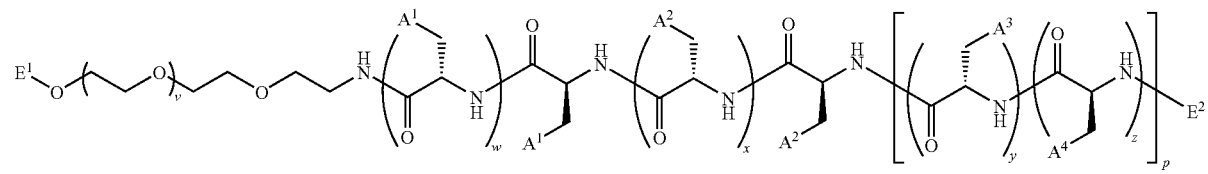

wherein each v is 100-500, each w is 4-20, x is 4-20, each y is 5-50, each z is 5-50, p is the sum of y and z, and each dotted bond represents the point of attachment to the rest of the molecule.

TABLE 3

| Compound | A¹ | A² | A³ | A⁴ | E¹ | E² |
|---|---|---|---|---|---|---|
| 193 | -COOH | -SH | -C₆H₅- | -C₆H₄-OH | HC≡C-CH₂- | -C(=O)- |
| 194 | -COOH | -SH | -C₆H₅- | -C₆H₄-OH | H₂N-CH₂-CH₂- | -C(=O)- |
| 195 | -COOH | -SH | -C₆H₅- | -C₆H₄-OH | N₃-CH₂-CH₂- | -C(=O)- |
| 196 | -COOH | -SH | -C₆H₅- | -C₆H₄-OH | H-C(=O)-CH₂-CH₂- | -C(=O)- |
| 197 | -COOH | -SH | -C₆H₅- | -C₆H₄-OH | H₃C- | -C(=O)- |
| 198 | -CH₂-COOH | -SH | -C₆H₅- | -C₆H₄-OH | HC≡C-CH₂- | -C(=O)- |
| 199 | -CH₂-COOH | -SH | -C₆H₅- | -C₆H₄-OH | H₂N-CH₂-CH₂- | -C(=O)- |
| 200 | -CH₂-COOH | -SH | -C₆H₅- | -C₆H₄-OH | N₃-CH₂-CH₂- | -C(=O)- |
| 201 | -CH₂-COOH | -SH | -C₆H₅- | -C₆H₄-OH | H-C(=O)-CH₂-CH₂- | -C(=O)- |
| 202 | -CH₂-COOH | -SH | -C₆H₅- | -C₆H₄-OH | H₃C- | -C(=O)- |
| 203 | -COOH | -SH | -C₆H₅- | -C₆H₄-OH | HC≡C-CH₂- | -H |
| 204 | -COOH | -SH | -C₆H₅- | -C₆H₄-OH | H₂N-CH₂-CH₂- | -H |
| 205 | -COOH | -SH | -C₆H₅- | -C₆H₄-OH | N₃-CH₂-CH₂- | -H |

TABLE 3-continued

| Compound | A¹ | A² | A³ | A⁴ | E¹ | E² |
|---|---|---|---|---|---|---|
| 206 | -C(=O)OH | -SH | phenyl | 4-hydroxyphenyl | -C(=O)CH₂CH₂- (with H) | -H |
| 207 | -C(=O)OH | -SH | phenyl | 4-hydroxyphenyl | H₃C- | -H |
| 208 | -CH₂C(=O)OH | -SH | phenyl | 4-hydroxyphenyl | HC≡C-CH₂- | -H |
| 209 | -CH₂C(=O)OH | -SH | phenyl | 4-hydroxyphenyl | H₂N-CH₂CH₂- | -H |
| 210 | -CH₂C(=O)OH | -SH | phenyl | 4-hydroxyphenyl | N₃-CH₂CH₂- | -H |
| 211 | -CH₂C(=O)OH | -SH | phenyl | 4-hydroxyphenyl | -C(=O)CH₂CH₂- (with H) | -H |
| 212 | -CH₂C(=O)OH | -SH | phenyl | 4-hydroxyphenyl | H₃C- | -H |

Table 4 sets forth exemplary compounds of the formula:

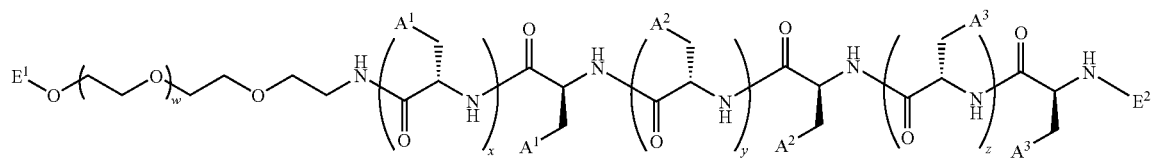

wherein each w is 25-1000, each x is 1-50, y is 1-50, each z is 1-100, and each dotted bond represents the point of attachment to the rest of the molecule.

TABLE 4

| Compound | A¹ | A² | A³ | E¹ | E² |
|---|---|---|---|---|---|
| 213 | -C(=O)OH | -SH | phenyl | HC≡C-CH₂- | -C(=O)CH₃ |
| 214 | -C(=O)OH | -SH | 4-hydroxyphenyl | HC≡C-CH₂- | -C(=O)CH₃ |

TABLE 4-continued

| Compound | A¹ | A² | A³ | E¹ | E² |
|---|---|---|---|---|---|
| 215 | COOH | SH | propyl-NH₂ | alkyne | ketone |
| 216 | COOH | SH | 1H-imidazol-4-yl | alkyne | ketone |
| 217 | COOH | SH | 1H-indol-2-yl | alkyne | ketone |
| 218 | COOH | SH | benzyl ester | alkyne | ketone |
| 219 | COOH | SH | benzyl ester (CH₂) | alkyne | ketone |
| 220 | CH₂COOH | SH | phenyl | alkyne | ketone |
| 221 | CH₂COOH | SH | 4-hydroxyphenyl | alkyne | ketone |
| 222 | CH₂COOH | SH | propyl-NH₂ | alkyne | ketone |
| 223 | CH₂COOH | SH | 1H-imidazol-4-yl | alkyne | ketone |
| 224 | CH₂COOH | SH | 1H-indol-2-yl | alkyne | ketone |
| 225 | CH₂COOH | SH | benzyl ester | alkyne | ketone |
| 226 | CH₂COOH | SH | benzyl ester (CH₂) | alkyne | ketone |

TABLE 4-continued

| Compound | A¹ | A² | A³ | E¹ | E² |
|---|---|---|---|---|---|
| 227 | -C(O)OH | -SH | phenyl | -C≡CH | -H |
| 228 | -C(O)OH | -SH | 4-hydroxyphenyl | -C≡CH | -H |
| 229 | -C(O)OH | -SH | -CH₂CH₂NH₂ | -C≡CH | -H |
| 230 | -C(O)OH | -SH | 1H-imidazol-2-yl | -C≡CH | -H |
| 231 | -C(O)OH | -SH | 1H-indol-2-yl | -C≡CH | -H |
| 232 | -C(O)OH | -SH | -C(O)OCH₂-phenyl | -C≡CH | -H |
| 233 | -C(O)OH | -SH | -CH₂C(O)OCH₂-phenyl | -C≡CH | -H |
| 234 | -CH₂C(O)OH | -SH | phenyl | -C≡CH | -H |
| 235 | -CH₂C(O)OH | -SH | 4-hydroxyphenyl | -C≡CH | -H |
| 236 | -CH₂C(O)OH | -SH | -CH₂CH₂NH₂ | -C≡CH | -H |
| 237 | -CH₂C(O)OH | -SH | 1H-imidazol-4-yl | -C≡CH | -H |
| 238 | -CH₂C(O)OH | -SH | 1H-indol-2-yl | -C≡CH | -H |

TABLE 4-continued

| Compound | A¹ | A² | A³ | E¹ | E² |
|---|---|---|---|---|---|
| 239 | -CH₂-COOH | -SH | -C(=O)-O-CH₂-C₆H₅ | -C≡CH | -H |
| 240 | -CH₂-COOH | -SH | -CH₂-C(=O)-O-CH₂-C₆H₅ | -C≡CH | -H |
| 241 | -COOH | -SH | -C₆H₅ | -CH₂-CH₂-N₃ | -C(=O)-CH₃ |
| 242 | -COOH | -SH | -C₆H₄-OH (para) | -CH₂-CH₂-N₃ | -C(=O)-CH₃ |
| 243 | -COOH | -SH | -CH₂-CH₂-CH₂-NH₂ | -CH₂-CH₂-N₃ | -C(=O)-CH₃ |
| 244 | -COOH | -SH | imidazole | -CH₂-CH₂-N₃ | -C(=O)-CH₃ |
| 245 | -COOH | -SH | indole (2-yl) | -CH₂-CH₂-N₃ | -C(=O)-CH₃ |
| 246 | -COOH | -SH | -C(=O)-O-CH₂-C₆H₅ | -CH₂-CH₂-N₃ | -C(=O)-CH₃ |
| 247 | -COOH | -SH | -CH₂-C(=O)-O-CH₂-C₆H₅ | -CH₂-CH₂-N₃ | -C(=O)-CH₃ |
| 248 | -CH₂-COOH | -SH | -C₆H₅ | -CH₂-CH₂-N₃ | -C(=O)-CH₃ |
| 249 | -CH₂-COOH | -SH | -C₆H₄-OH (para) | -CH₂-CH₂-N₃ | -C(=O)-CH₃ |
| 250 | -CH₂-COOH | -SH | -CH₂-CH₂-CH₂-NH₂ | -CH₂-CH₂-N₃ | -C(=O)-CH₃ |

TABLE 4-continued

| Compound | A¹ | A² | A³ | E¹ | E² |
|---|---|---|---|---|---|
| 251 | CH₂COOH | SH | imidazole | N₃-CH₂CH₂- | C(O)CH₃ |
| 252 | CH₂COOH | SH | indole (2-yl) | N₃-CH₂CH₂- | C(O)CH₃ |
| 254 | CH₂COOH | SH | -C(O)O-CH₂-Ph | N₃-CH₂CH₂- | C(O)CH₃ |
| 255 | CH₂COOH | SH | -CH₂C(O)O-CH₂-Ph | N₃-CH₂CH₂- | C(O)CH₃ |
| 256 | COOH | SH | Ph | N₃-CH₂CH₂- | H |
| 257 | COOH | SH | 4-hydroxyphenyl | N₃-CH₂CH₂- | H |
| 258 | COOH | SH | -CH₂CH₂CH₂NH₂ | N₃-CH₂CH₂- | H |
| 259 | COOH | SH | imidazole | N₃-CH₂CH₂- | H |
| 260 | COOH | SH | indole (2-yl) | N₃-CH₂CH₂- | H |
| 261 | COOH | SH | -C(O)O-CH₂-Ph | N₃-CH₂CH₂- | H |
| 262 | COOH | SH | -CH₂C(O)O-CH₂-Ph | N₃-CH₂CH₂- | H |
| 263 | CH₂COOH | SH | Ph | N₃-CH₂CH₂- | H |

TABLE 4-continued

| Compound | A¹ | A² | A³ | E¹ | E² |
|---|---|---|---|---|---|
| 264 | -C(=O)OH | -SH | 4-hydroxyphenyl | N₃-CH₂CH₂- | -H |
| 265 | -C(=O)OH | -SH | -CH₂CH₂NH₂ | N₃-CH₂CH₂- | -H |
| 266 | -C(=O)OH | -SH | 1H-imidazol-4-yl | N₃-CH₂CH₂- | -H |
| 267 | -C(=O)OH | -SH | 1H-indol-2-yl | N₃-CH₂CH₂- | -H |
| 268 | -C(=O)OH | -SH | -C(=O)O-CH₂-phenyl | N₃-CH₂CH₂- | -H |
| 269 | -C(=O)OH | -SH | -CH₂C(=O)O-CH₂-phenyl | N₃-CH₂CH₂- | -H |
| 270 | -C(=O)OH | -SH | phenyl | H-C(=O)-CH₂CH₂- | -C(=O)CH₃ |
| 271 | -C(=O)OH | -SH | 4-hydroxyphenyl | H-C(=O)-CH₂CH₂- | -C(=O)CH₃ |
| 272 | -C(=O)OH | -SH | -CH₂CH₂NH₂ | H-C(=O)-CH₂CH₂- | -C(=O)CH₃ |
| 273 | -C(=O)OH | -SH | 1H-imidazol-4-yl | H-C(=O)-CH₂CH₂- | -C(=O)CH₃ |
| 274 | -C(=O)OH | -SH | 1H-indol-2-yl | H-C(=O)-CH₂CH₂- | -C(=O)CH₃ |
| 275 | -C(=O)OH | -SH | -C(=O)O-CH₂-phenyl | H-C(=O)-CH₂CH₂- | -C(=O)CH₃ |

TABLE 4-continued

| Compound | A¹ | A² | A³ | E¹ | E² |
|---|---|---|---|---|---|
| 276 | COOH | SH | CH₂C(O)O-CH₂-phenyl | CH₂CH₂CHO | C(O)CH₃ |
| 277 | CH₂COOH | SH | phenyl | CH₂CH₂CHO | C(O)CH₃ |
| 278 | CH₂COOH | SH | 4-hydroxyphenyl | CH₂CH₂CHO | C(O)CH₃ |
| 279 | CH₂COOH | SH | CH₂CH₂NH₂ | CH₂CH₂CHO | C(O)CH₃ |
| 280 | CH₂COOH | SH | imidazol-4-yl | CH₂CH₂CHO | C(O)CH₃ |
| 281 | CH₂COOH | SH | 1H-indol-2-yl | CH₂CH₂CHO | C(O)CH₃ |
| 282 | CH₂COOH | SH | C(O)O-CH₂-phenyl | CH₂CH₂CHO | C(O)CH₃ |
| 283 | CH₂COOH | SH | CH₂C(O)O-CH₂-phenyl | CH₂CH₂CHO | C(O)CH₃ |
| 284 | COOH | SH | phenyl | CH₂CH₂CHO | H |
| 285 | COOH | SH | 4-hydroxyphenyl | CH₂CH₂CHO | H |
| 286 | COOH | SH | CH₂CH₂NH₂ | CH₂CH₂CHO | H |

TABLE 4-continued

| Compound | A¹ | A² | A³ | E¹ | E² |
|---|---|---|---|---|---|
| 287 | COOH | SH | imidazol-4-yl | CH₂CHO | H |
| 288 | COOH | SH | indol-2-yl | CH₂CHO | H |
| 289 | COOH | SH | C(O)OCH₂Ph | CH₂CHO | H |
| 290 | COOH | SH | CH₂C(O)OCH₂Ph | CH₂CHO | H |
| 291 | CH₂COOH | SH | phenyl | CH₂CHO | H |
| 292 | CH₂COOH | SH | 4-hydroxyphenyl | CH₂CHO | H |
| 293 | CH₂COOH | SH | CH₂CH₂CH₂NH₂ | CH₂CHO | H |
| 294 | CH₂COOH | SH | imidazol-4-yl | CH₂CHO | H |
| 295 | CH₂COOH | SH | indol-2-yl | CH₂CHO | H |
| 296 | CH₂COOH | SH | C(O)OCH₂Ph | CH₂CHO | H |

TABLE 4-continued
| Compound | A¹ | A² | A³ | E¹ | E² |
|---|---|---|---|---|---|
| 297 | ⋯⟨CH₂COOH⟩ | ⋯SH | ⋯⟨CH₂C(O)O-CH₂-C₆H₅⟩ | H-C(O)-CH₂CH₂-⋯ | ⋯H |
In some embodiments, a micelle in accordance with the present invention comprises a compound selected from any of the following:
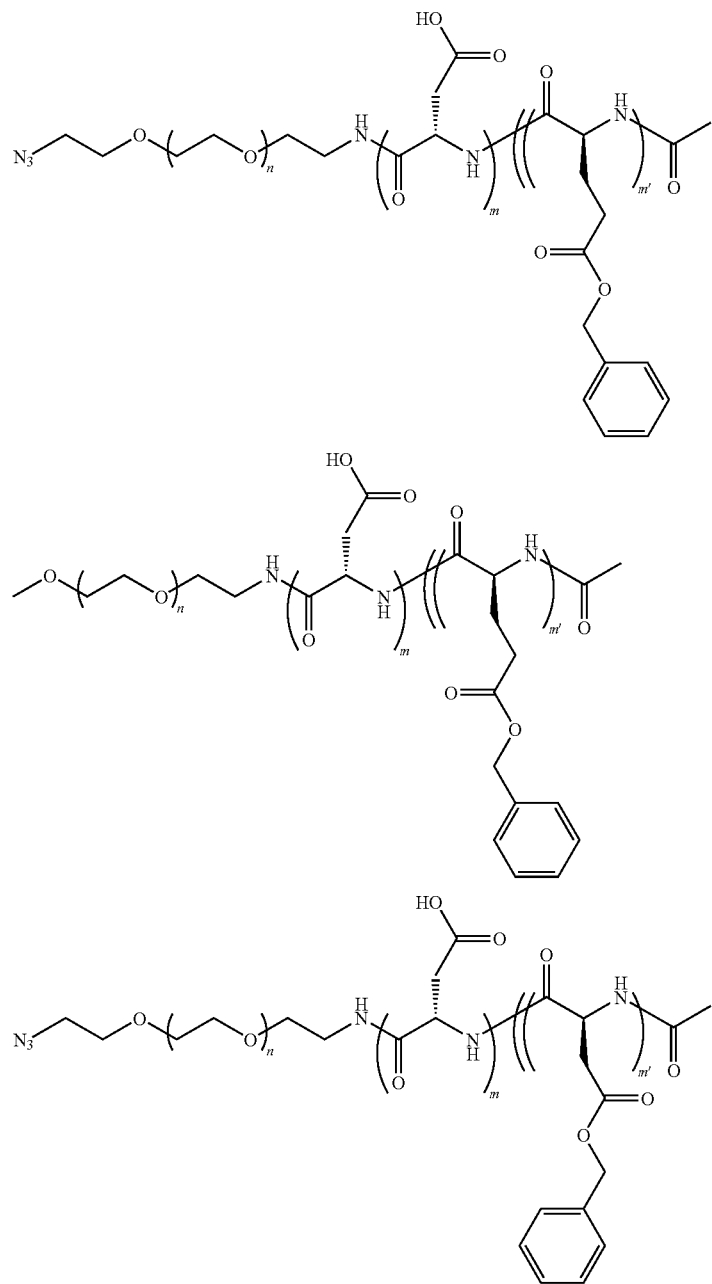

-continued
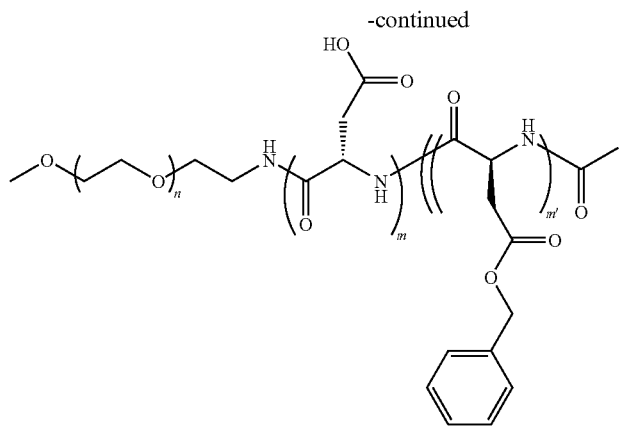
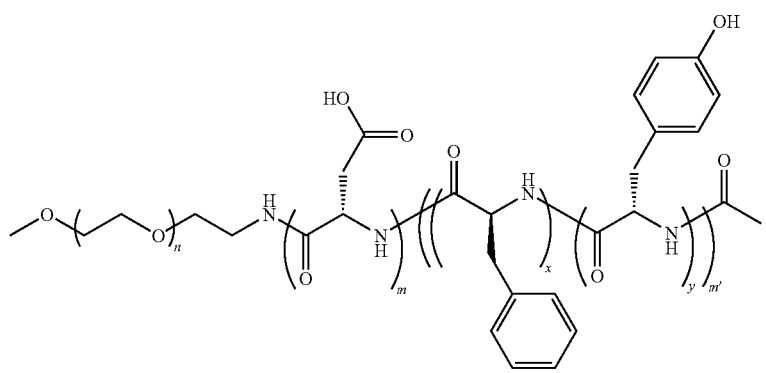
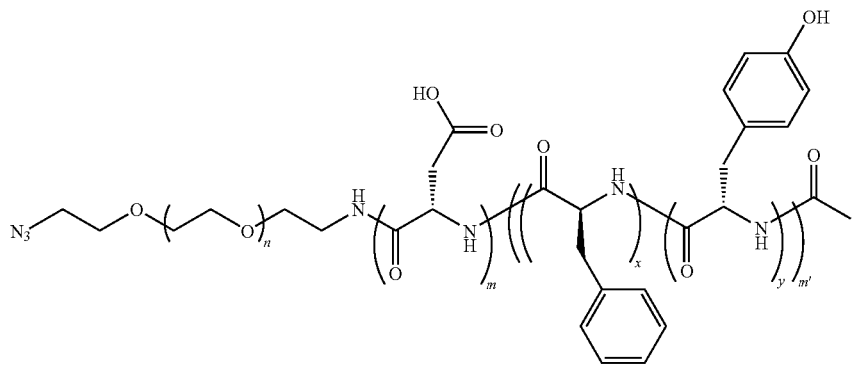
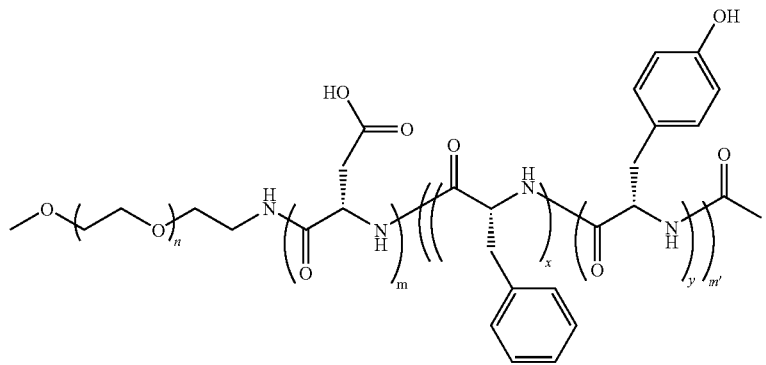

-continued
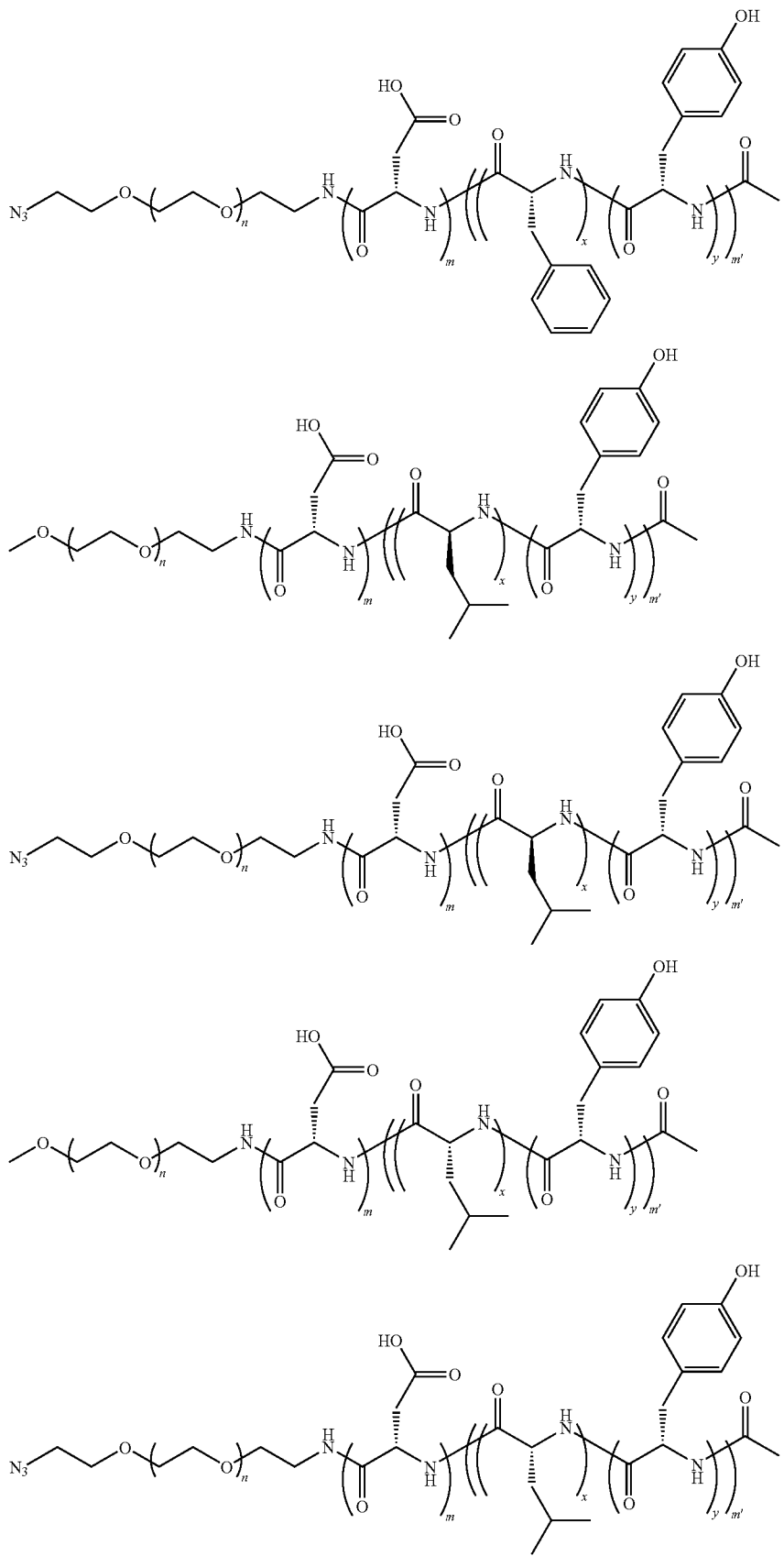

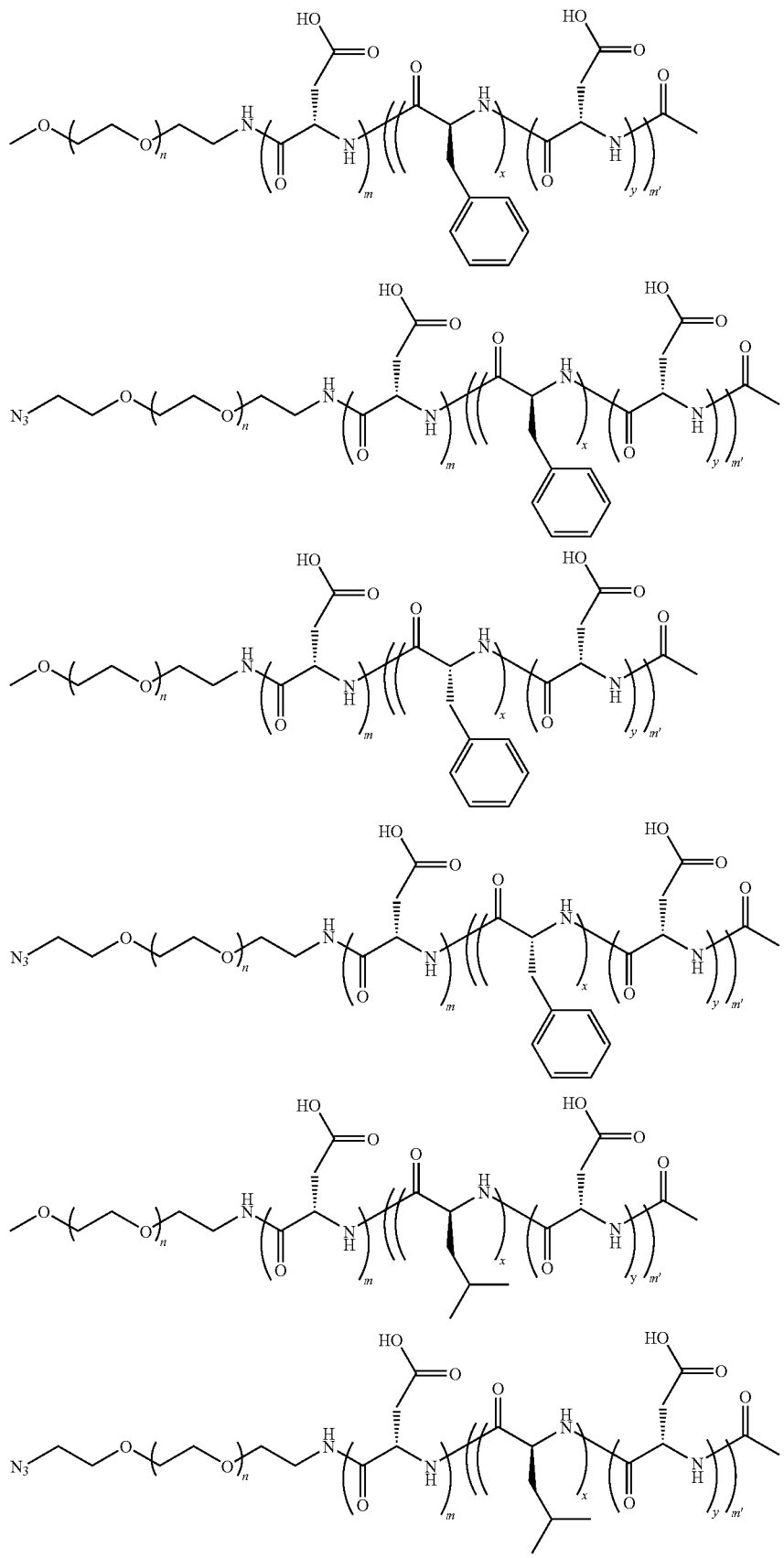

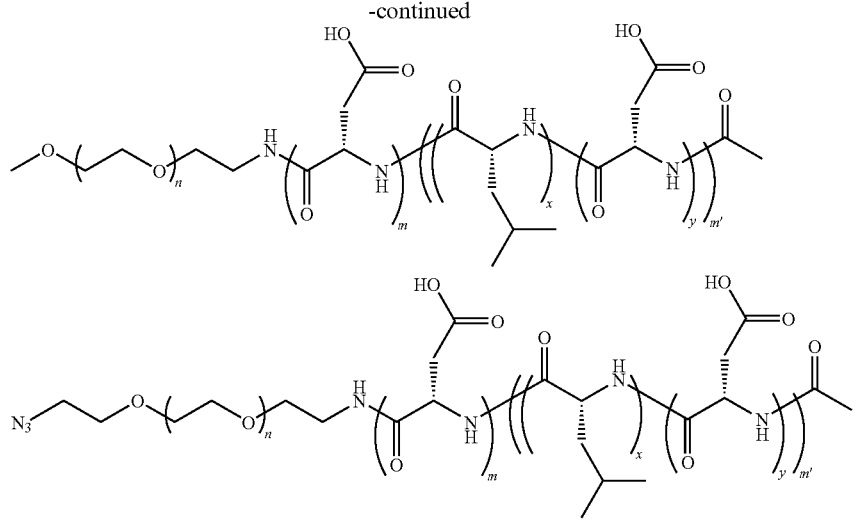

wherein each n, m, and m' is as described above and herein. In certain embodiments, each m is 5-15, each x is 1-100, each y is 1-100, and each m' is 20-100 such that x+y=m'. In certain embodiments, each n is 200-300, each x is 5-15 and each y is 15-25. In some embodiments, m is 10, x is 20, y is 20, and m' is 40. In other embodiments, m is 10, x is 25, y is 25, and m' is 50. In certain embodiments, m is 10 and m' is 30.

In certain embodiments, a micelle in accordance with the present invention comprises a compound selected from any of the following:

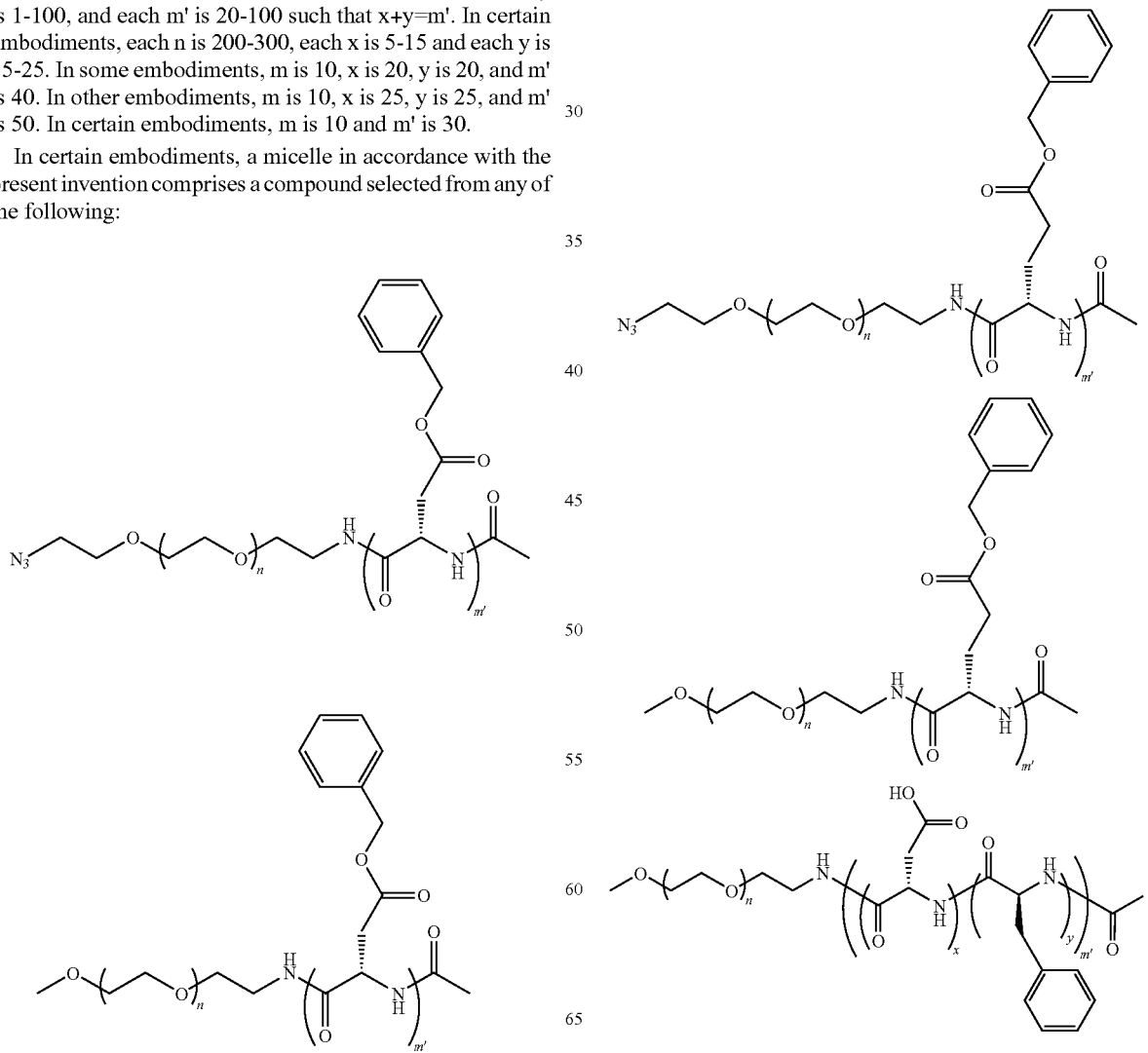

91
-continued
92
-continued
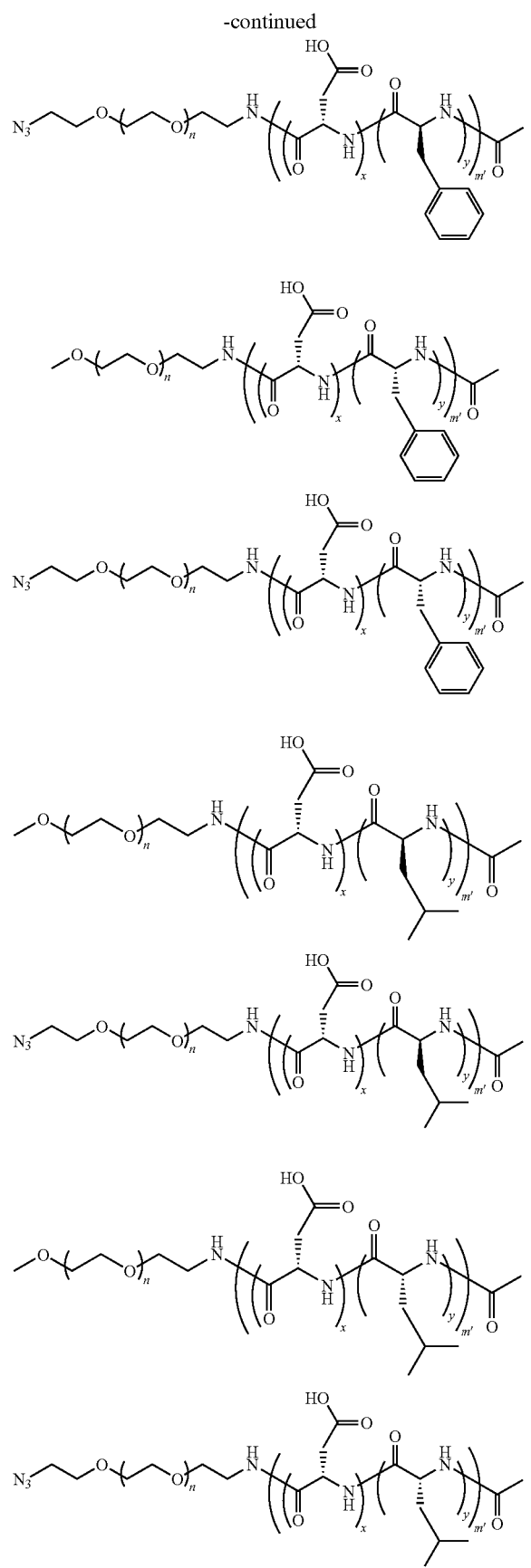
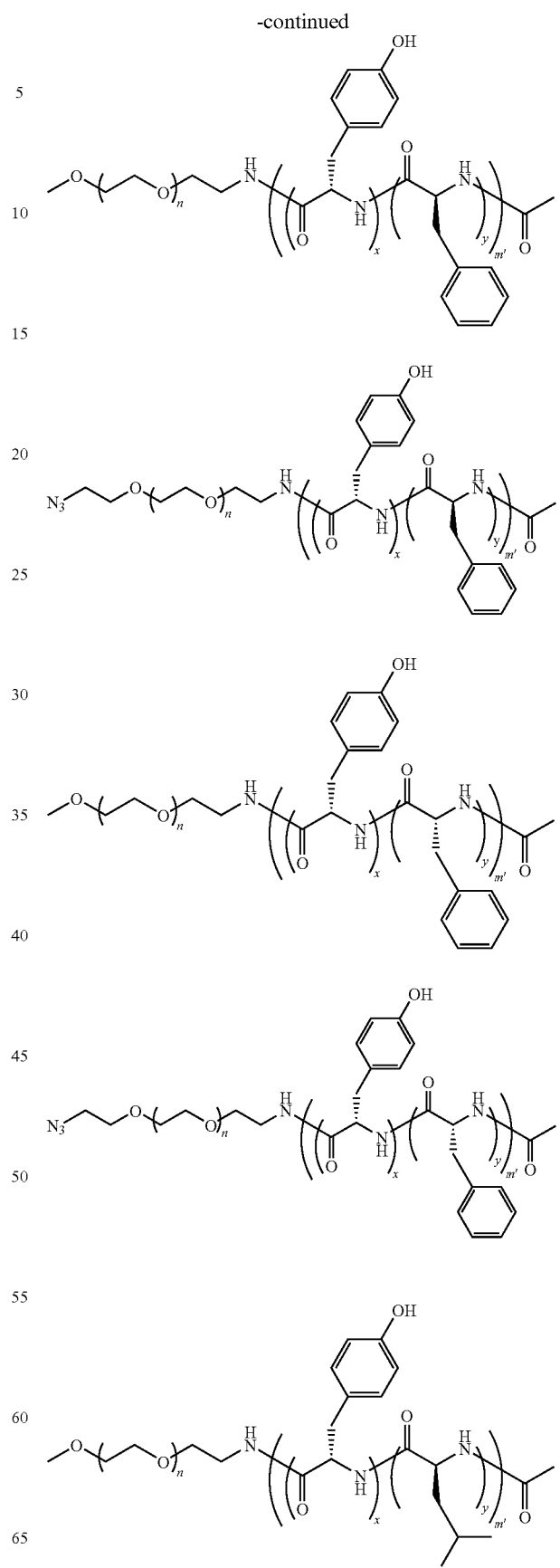

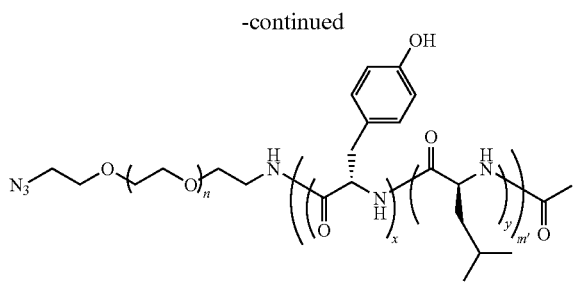

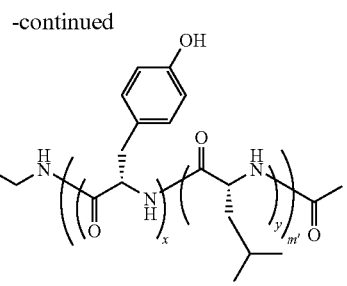

wherein each n, m, and m' is as described above and herein. In certain embodiments, each x is 1-100, each y is 1-100, and each m' is 20-100 such that x+y=m'. In certain embodiments, each n is 200-300, each x is 5-15 and each y is 15-25. In some embodiments, x is 20, y is 20, and m' is 40. In other embodiments, x is 25, y is 25, and m' is 50.

In certain embodiments, a micelle in accordance with the present invention comprises a compound selected from any of the following:

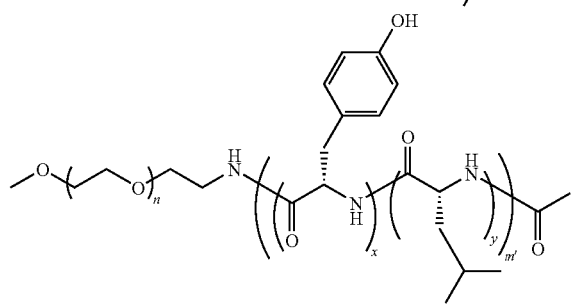

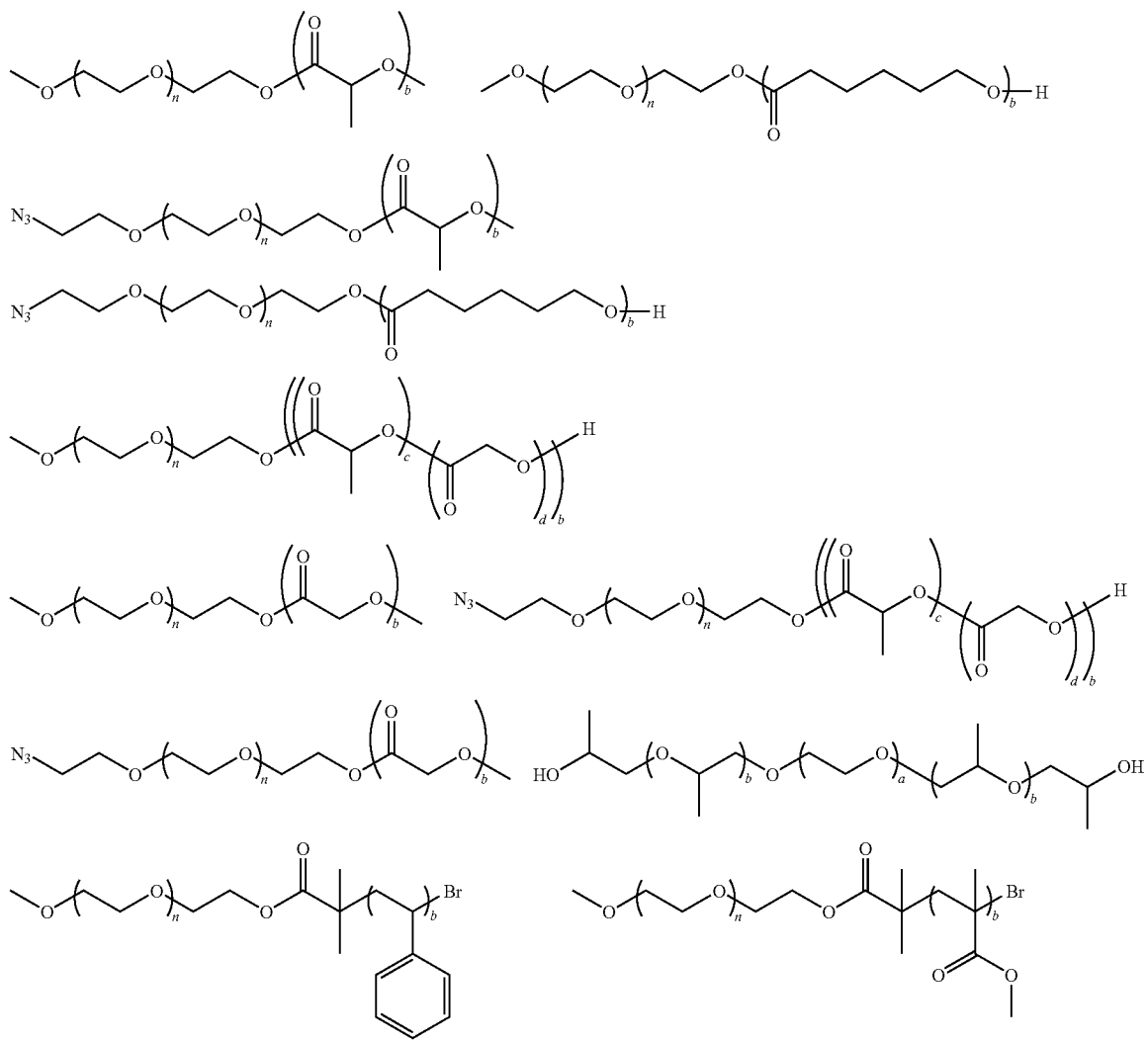

-continued

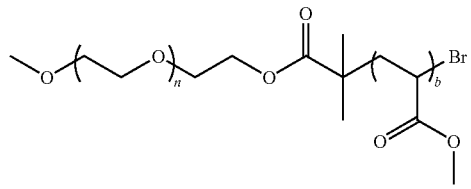
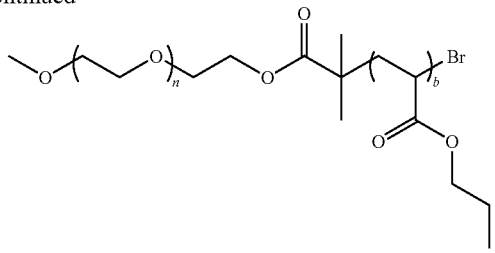

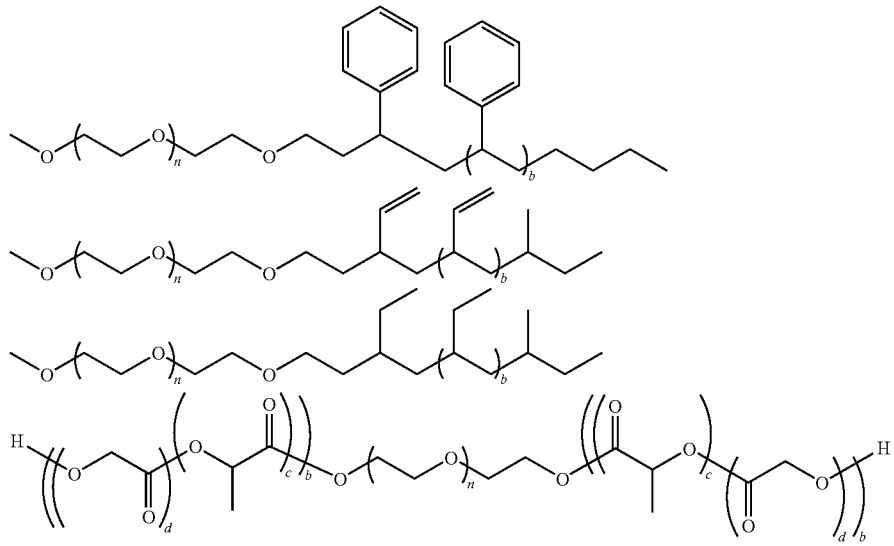

wherein each n is as described above and herein. In certain embodiments, each b is 1-100, each c is 1-100, and each d is 1-100 such that c+d=b. In certain embodiments, each n is 200-300, each c is 5-15 and each d is 15-25. In some embodiments, c is 20, d is 20, and b is 40. In other embodiments, c is 25, d is 25, and b is 50.

B. Crosslinking Chemistries

As described generally above, in certain embodiments, a micelle of the present invention, having an amyloid-beta (1-42) peptide, or a fragment thereof, encapsulated therein, optionally comprises a crosslinkable or crosslinked "outer core." The crosslinking of poly(amino acid) groups is known in the art and includes methods described in detail in WO2006/107903, the entirety of which is hereby incorporated herein by reference.

In certain embodiments, micelles of the present invention, having an amyloid-beta (1-42) peptide, or a fragment thereof, encapsulated therein, comprise a crosslinked multiblock polymer of formula III:

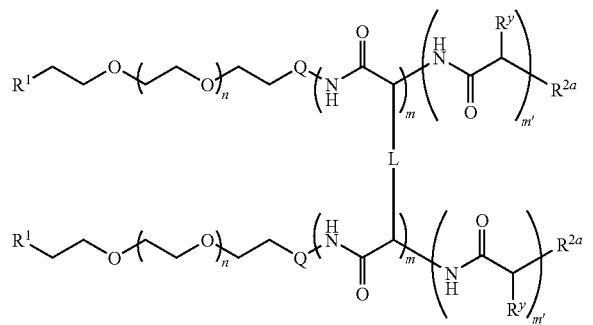

III wherein:
n is 10-2500;
m is 1 to 1000;
m' is 1 to 1000;
L is a bivalent, saturated or unsaturated, straight or branched $C_{1-12}$ alkylene chain, wherein 0-6 methylene units of L are independently replaced by -M-, -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-M- is a suitable bivalent metal;
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^y$ is a hydrophobic or ionic, natural or unnatural amino acid side-chain group;
$R^1$ is —Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N($R^4$)$_2$, —NR$^4$C(O)R$^4$, —NR$^4$C(O)N($R^4$)$_2$, —NR$^4$C(O)OR$^4$, or —NR$^4$SO$_2$R$^4$; and each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the compound of formula III, as described above, has a polydispersity index ("PDI") of about 1.0 to about 1.2. According to another embodiment, the compound of formula III, as described above, has a polydispersity index ("PDI") of about 1.03 to about 1.15. According to yet another embodiment, the compound of formula III, as described above, has a polydispersity index ("PDI") of about 1.10 to about 1.20. According to other embodiments, the compound of formula III has a PDI of less than about 1.10.

As defined generally above, the n group of formula I is 10-2500. In certain embodiments, the present invention provides compounds of formula I, as described above, wherein n is about 225. In other embodiments, n is about 270. In other embodiments, n is about 350. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, 225±10, 275±10, 315±10, or 340±10

In certain embodiments, the m' group of formula III is about 5 to about 500. In certain embodiments, the m' group of formula III is about 10 to about 250. In other embodiments, m' is about 10 to about 50. In other embodiments, m' is about 20 to about 40. According to yet another embodiment, m' is about 50 to about 75. According to other embodiments, m and m' are independently about 10 to about 100. In certain embodiments, m is 5-50. In other embodiments, m is 5-10. In other embodiments, m is 10-20. In certain embodiments, m and m' add up to about 30 to about 60. In still other embodiments, m is 1-20 repeat units and m' is 10-50 repeat units.

As defined generally above, the L group of formula III is a bivalent, saturated or unsaturated, straight or branched $C_{1-12}$ alkylene chain, wherein 0-6 methylene units of L are independently replaced by -M-, Cy, —O—, NH—, —S—, —C(O)—, —SO—, —SO2-, NHC(O)—, C(O)NH—, OC(O)NH—, or —NHC(O)O—, wherein -M- is a suitable bivalent metal, and -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. It will be appreciated that the L group of formula III represents crosslinked amino acid side-chain groups. In certain embodiments, the crosslinked amino acid side-chain groups correspond to the $R^x$ moiety of compounds of formulae I and II as described herein. In certain embodiments, the L group of formula III represents a metal crosslinked amino acid side-chain group, a hydrazone crosslinked amino acid side-chain group, an ester crosslinked amino acid side-chain group, an amide crosslinked side-chain group, an imine (e.g. Schiff base) crosslinked side-chain group, or a disulfide crosslinked side-chain group.

In certain embodiments, the L group of formula III comprises -M-. In other embodiments, -M- is zinc, calcium, iron or aluminum. In yet other embodiments, -M- is strontium, manganese, palladium, silver, gold, cadmium, chromium, indium, or lead.

In other embodiments, the L group of formula III is a bivalent, saturated or unsaturated, straight or branched $C_{1-12}$ alkylene chain wherein 2 methylene units of L are independently replaced by —C(O)—, —C(O)NH—, —NHC(O)—, —S—, —C(O)O—, —OC(O)—, —C(O)NHN—, —NNHC(O)—, —=N—, —N=—, -M-OC(O)—, or —C(O)O-M-. According to another embodiment, the L group of formula III is a bivalent, saturated or unsaturated, straight or branched $C_{1-6}$ alkylene chain, wherein two methylene units of L are replaced by —C(O)— or —C(O)NH—. In other embodiments, the L group of formula III is a bivalent, saturated or unsaturated, straight or branched $C_{1-12}$ alkylene chain having at least 2 units of unsaturation. According to yet another embodiment, the L group of formula III is a bivalent, saturated or unsaturated, straight or branched $C_{1-12}$ alkylene chain wherein two methylene units of L are replaced by —NH—. According to yet another embodiment, the L group of formula III is a bivalent, saturated or unsaturated, straight or branched $C_{1-12}$ alkylene chain wherein two methylene units of L are replaced by —C(O)NHN.

In certain embodiments, the -M- moiety of the L group of formula III is zinc. In other embodiments, L forms a zinc-dicarboxylate crosslinking moiety. In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

Scheme 1

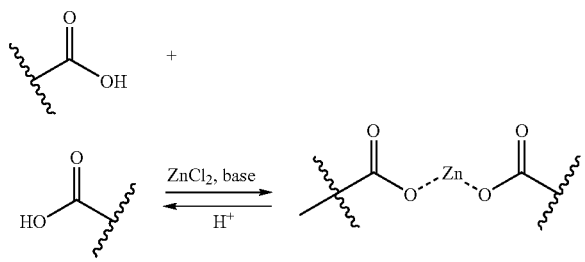

Scheme 1 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 4.0-6.8 to reform $ZnX_2$, where X is the conjugate base. One of ordinary skill in the art will recognize that a variety of natural and unnatural amino acid side-chains have a carboxylic acid moeity that can be crosslinked by zinc or another suitable metal.

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

The ultimate goal of metal-mediated crosslinking is to ensure micelle stability when diluted in the blood (pH 7.4) followed by rapid dissolution and drug release in response to a finite pH change such as those found in cancer cells. Previous reports suggest a widely variable and tunable dissociation pH for zinc-acid bonds (from approximately 2.0 to 7.0) depending on the carboxylic acid used and number of bonds formed. See Cannan, R. K.; Kibrick, A. *J. Am. Chem. Soc.* 1938, 60, 2314-2320. Without wishing to be bound by theory, it is believed that the concentration of zinc chloride and the number of aspartic acid, or other carboxylic acid-containing amino acid, repeat units in the crosslinking block will ultimately control the pH at which complete micelle disassembly occurs. The synthetic versatility of the block copolymer design is advantageous since one or more variables are tuned to achieve the desired pH reversibility. By simple adjustment of zinc chloride/polymer stoichiometry, pH-reversible crosslinking is finely tuned across the pH range of interest. For example, higher zinc concentrations yield more zinc crosslinks which require higher acid concentrations (i.e. lower pH) to dissociate. Adjustments in zinc/polymer stoichiometry will yield the desired pH reversibility, however other variables such as increasing the poly(aspartic acid) block length (i.e. 15-25 repeat units) further tune the reversible crosslinking reaction if necessary.

In other embodiments, L comprises a mixture of crosslinked hydrophilic amino acid side-chain groups. Such mixtures of amino acid side-chain groups include those having a carboxylic acid functionality, a hydroxyl functionality, a thiol functionality, and/or amine functionality. It will be appreciated that when L comprises a mixture of crosslinked hydrophilic amino acid side-chain functionalities, then multiple crosslinking can occur. For example, when L comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of therapeutic drugs to the cytosol of diseased cells because a second stimuli must be present to allow for drug release. For example, micelles possessing both carboxylic acid-zinc crosslinking and cysteine dithiol crosslinking would be required to enter an acidic environment (e.g. a tumor) and enter an environment with a high concentration of glutathione (e.g. in the cell cytoplasm). When L comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in drug release exclusively in the cytoplasm.

In certain embodiments, the $R^3$ moiety of the $R^1$ group of formula III is —$N_3$.

In certain embodiments, the $R^3$ moiety of the $R^1$ group of formula III is —$OCH_3$ In other embodiments, the $R^3$ moiety of the $R^1$ group of formula III is —CN.

In still other embodiments, the $R^3$ moiety of the $R^1$ group of formula III is a mono-protected amine or a di-protected amine.

In certain embodiments, the R moiety of the $R^1$ group of formula III is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula III is an optionally substituted aryl group. Examples include optionally substituted phenyl and optionally substituted pyridyl. When said $R^3$ moiety is a substituted aryl group, suitable substituents on $R^3$ include CN, $N_3$, $NO_2$, —$CH_3$, —$CH_2N_3$, —CH=$CH_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5- ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the $R^3$ moiety is an aryl group substituted with a suitably protected amino group. According to another aspect, the $R^3$ moiety is phenyl substituted with a suitably protected amino group.

In other embodiments, the $R^3$ moiety of the $R^1$ group of formula III is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula III is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula I is a protected aldehyde group. In certain embodiments the protected aldehydro moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl)acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula III is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiments, the $R^3$ moiety of the $R^1$ group of formula III is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodiments, $R^3$ is —S—S-pyridin-2-yl, —S—SBn, —S—SCH$_3$, or —S—S(p-ethynylbenzyl). In other embodiments, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula III is a crown ether. Examples of such crown ethers include 12-crown-4, 15-crown-5, and 18-crown-6.

In still other embodiments, the $R^3$ moiety of the $R^1$ group of formula III is a detectable moiety. According to one aspect of the invention, the $R^3$ moiety of the $R^1$ group of formula III is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of formula III is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

In certain embodiments, the $R^3$ moiety of the $R^1$ group of formula III is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula III to a macromolecule via Click chemistry. Yet another embodiment of the present invention provides a macromolecule conjugated to a compound of formula III via the $R^1$ group.

According to one embodiment, the $R^3$ moiety of the $R^1$ group of formula III is an azide-containing group. According to another embodiment, the $R^3$ moiety of the $R^1$ group of formula III is an alkyne-containing group. In certain embodiments, the $R^3$ moiety of the $R^1$ group of formula III has a terminal alkyne moiety. In other embodiments, $R^3$ moiety of the $R^1$ group of formula III is an alkyne moiety having an electron withdrawing group. Accordingly, in such embodiments, the $R^3$ moiety of the $R^1$ group of formula III is

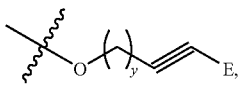

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula III is

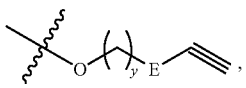

wherein E is an electron withdrawing group, such as a —C(O)O— group and y is 0-6.

As defined generally above, Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^y$ is a hydrophobic amino acid side-chain group. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol functional groups of $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, leucine/aspartic acid, phenylalanine/aspartic acid, and the like. According to another embodiment, $R^y$ is a hydrophobic amino acid side-chain group selected from phenylalanine, alanine, or leucine, and one or more of tyrosine, serine, or threonine.

As defined generally above, the $R^{2a}$ group of formula III is a mono-protected amine, a di-protected amine, —NHR$^4$, —N(R$^4$)$_2$, —NHC(O)R$^4$, —NR$^4$C(O)R$^4$, —NHC(O)NHR$^4$, —NHC(O)N(R$^4$)$_2$, —NR$^4$C(O)NHR$^4$, —NR$^4$C(O)N(R$^4$)$_2$, —NHC(O)OR$^4$, —NR$^4$C(O)OR$^4$, —NHSO$_2$R$^4$, or —NR$^4$SO$_2$R$^4$, wherein each R$^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula III is —NHC(O)$R^4$, wherein $R^4$ is an optionally substituted aliphatic group. In other embodiments, the $R^{2a}$ group of formula III is —NHC(O)Me.

In certain embodiments, the $R^{2a}$ group of formula III is —NH$R^4$ or —N($R^4$)$_2$ wherein each $R^4$ is hydrogen.

In certain embodiments, the $R^{2a}$ group of formula III is —NH$R^4$ or —N($R^4$)$_2$ wherein each $R^4$ is an optionally substituted aliphatic group. One exemplary $R^4$ group is 5-norbornen-2-yl-methyl. According to yet another aspect of the present invention, the $R^{2a}$ group of formula III is —NH$R^4$ wherein $R^4$ is a $C_{1-6}$ aliphatic group substituted with $N_3$. Examples include —CH$_2$N$_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —CH$_2$CN, —CH$_2$CH$_2$CN, —CH$_2$CH(OCH$_3$)$_2$, 4-(bisbenzyloxymethyl)phenylmethyl, and the like.

According to another aspect of the present invention, the $R^{2a}$ group of formula III is —NH$R^4$ wherein $R^4$ is an optionally substituted $C_{2-6}$ alkynyl group. Examples include —CC≡CH, —CH$_2$C≡CH, —CH$_2$C≡CCH$_3$, and —CH$_2$CH$_2$C≡CH.

In certain embodiments, the $R^{2a}$ group of formula III is —NH$R^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula III is —NH$R^4$ wherein $R^4$ is an optionally substituted phenyl ring. Suitable substituents on the $R^4$ phenyl ring include halogen; —(CH$_2$)$_{0-4}$R°; —(CH$_2$)$_{0-4}$OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —(CH$_2$)$_{0-4}$SC(O)R°; —(CH$_2$)$_{0-4}$C(O)NR°$_2$; —C(S)NR°$_2$; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-40}$S(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; SiR°$_3$; wherein each independent occurrence of R° is as defined herein supra. In other embodiments, the $R^{2a}$ group of formula III is —NH$R^4$ wherein $R^4$ is phenyl substituted with one or more optionally substituted $C_{1-6}$ aliphatic groups. In still other embodiments, $R^4$ is phenyl substituted with vinyl, allyl, acetylenyl, —CH$_2$N$_3$, —CH$_2$CH$_2$N$_3$, —CH$_2$C≡CCH$_3$, or —CH$_2$C≡CH.

In certain embodiments, the $R^{2a}$ group of formula III is —NH$R^4$ wherein $R^4$ is phenyl substituted with N$_3$, N(R°)$_2$, CO$_2$R°, or C(O)R° wherein each R° is independently as defined herein supra.

In certain embodiments, the $R^{2a}$ group of formula III is —N($R^4$)$_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula III is —N($R^4$)$_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula III is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

Exemplary $R^1$ groups of any of formulae I, II, and III are set forth in Table 5, below.

TABLE 5

Representative $R^1$ Groups

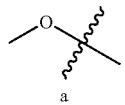

a

TABLE 5-continued
Representative R¹ Groups
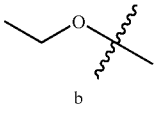
b
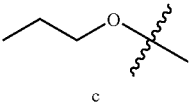
c
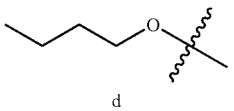
d
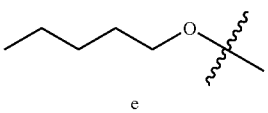
e
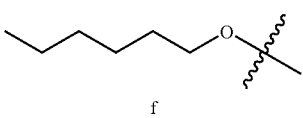
f
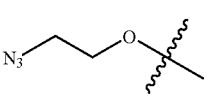
g
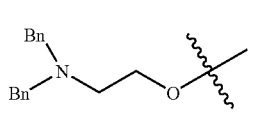
h
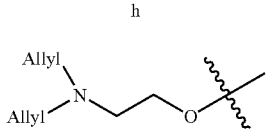
i
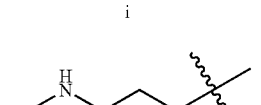
j
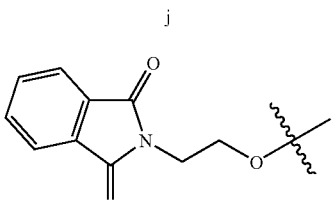
k
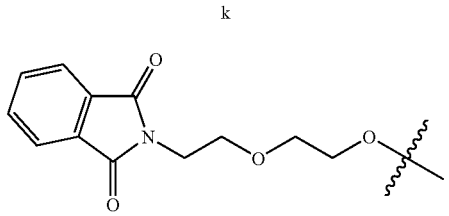
l
TABLE 5-continued
Representative R¹ Groups
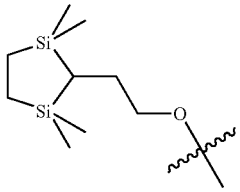
m
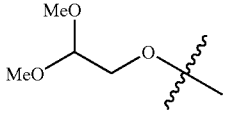
n
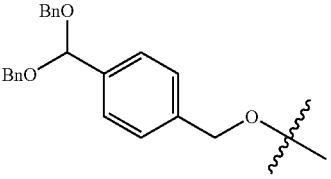
o
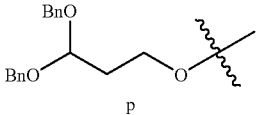
p
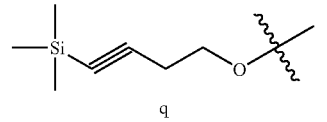
q
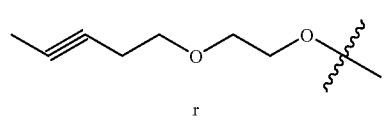
r
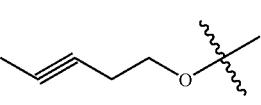
s
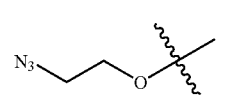
t
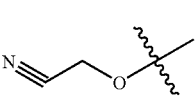
u
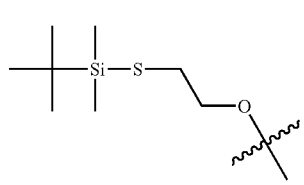
v TABLE 5-continued Representative R¹ Groups w, x, y, z, aa, bb, cc, dd, ee, ff, gg, hh, ii, jj, kk, ll, mm TABLE 5-continued
Representative R¹ Groups
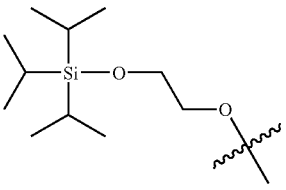
nn
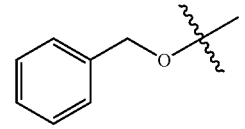
oo
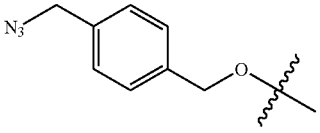
pp
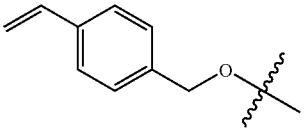
qq
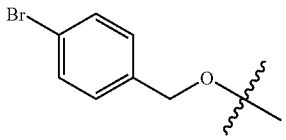
rr
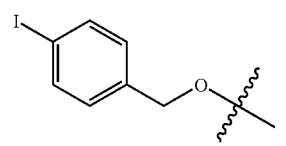
ss
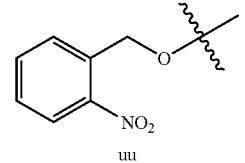
tt
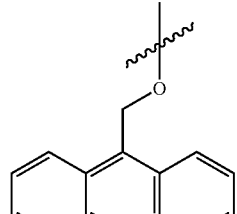
uu
TABLE 5-continued
Representative R¹ Groups
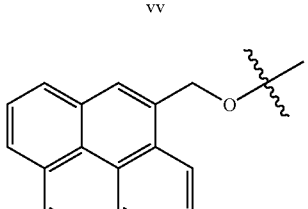
vv
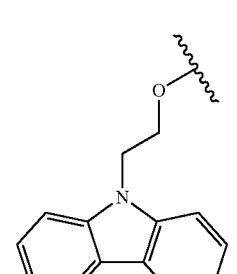
ww
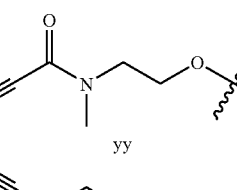
xx
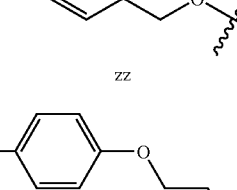
yy
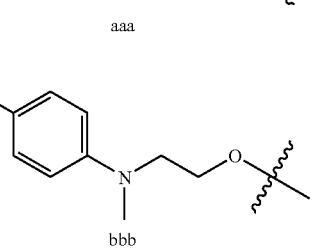
zz
aaa
bbb TABLE 5-continued
Representative R¹ Groups
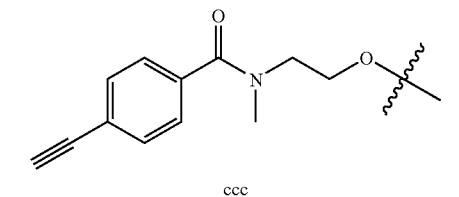
ccc
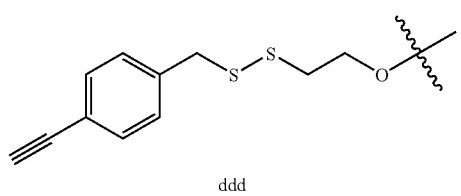
ddd
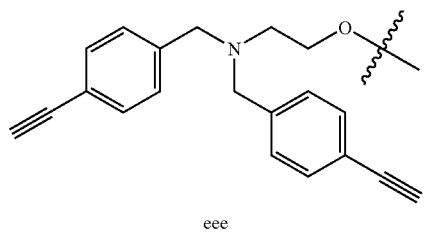
eee
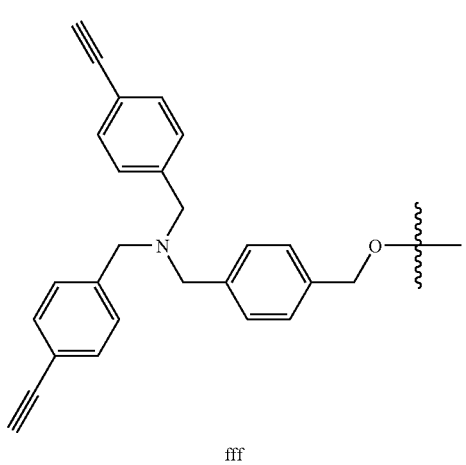
fff
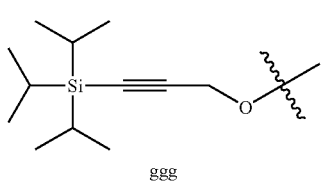
ggg
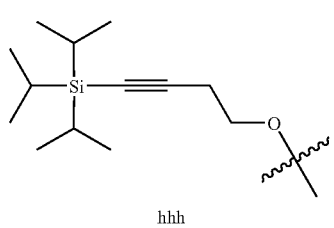
hhh
TABLE 5-continued
Representative R¹ Groups
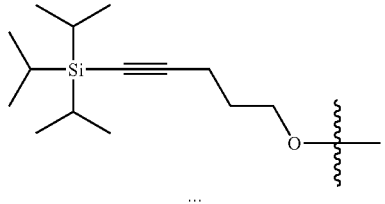
iii
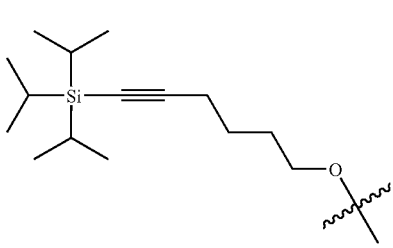
jjj
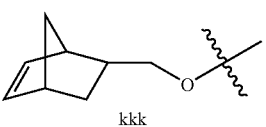
kkk
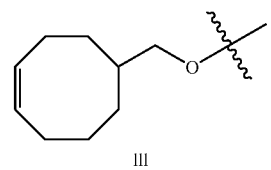
lll
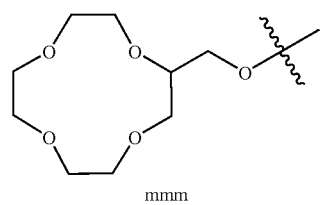
mmm
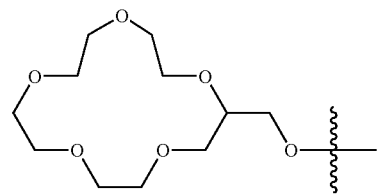
nnn
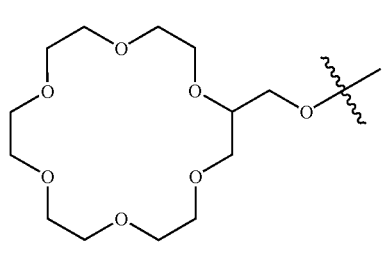
ooo TABLE 5-continued Representative R¹ Groups

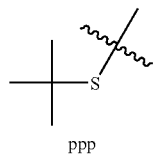
ppp

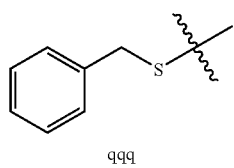
qqq

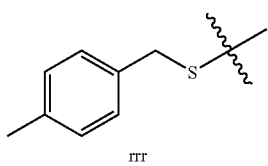
rrr

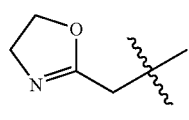
sss

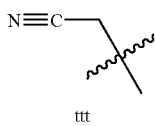
ttt

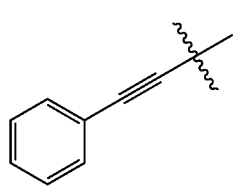
uuu

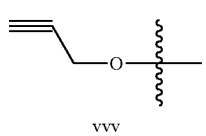
vvv

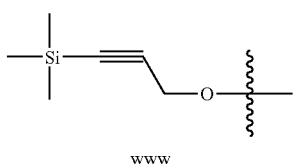
www

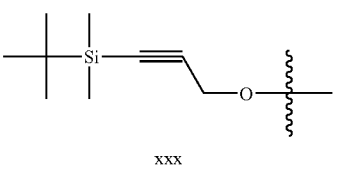
xxx

TABLE 5-continued

Representative R¹ Groups

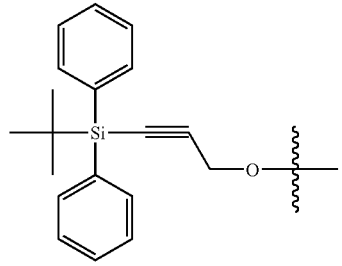
yyy

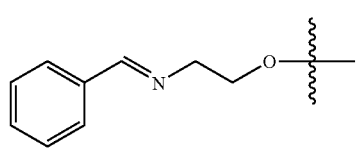
zzz

One of ordinary skill in the art would recognize that certain R¹ groups depicted in Table 5 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 5 are also contemplated. According to another embodiment, the R¹ group of any of formulae I, II, and III is selected from a deprotected group of Table 5.

Additional exemplary R¹ groups of any of formulae I, II, and III are set forth in Table 5a, below.

TABLE 5a

Representative R¹ Groups

a

b

c

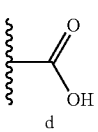
d

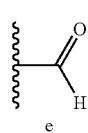
e

TABLE 5a-continued
Representative R¹ Groups
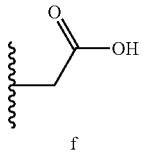
f
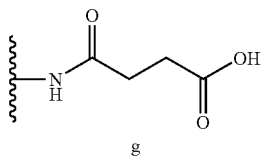
g
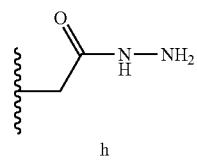
h
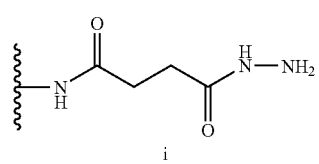
i
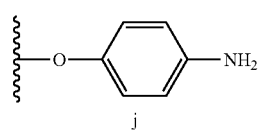
j
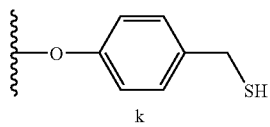
k
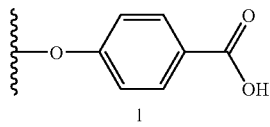
l
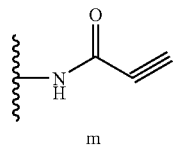
m
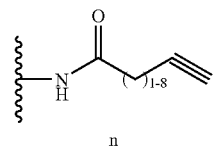
n
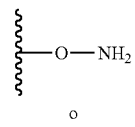
o
TABLE 5a-continued
Representative R¹ Groups
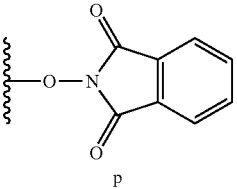
p
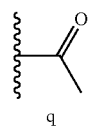
q
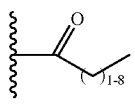
r
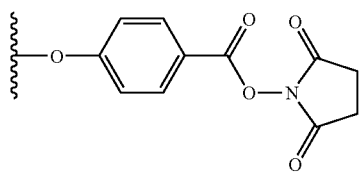
s
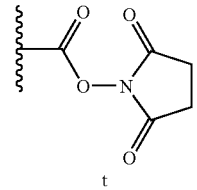
t
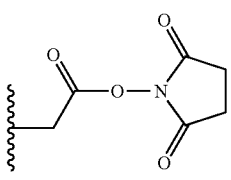
u
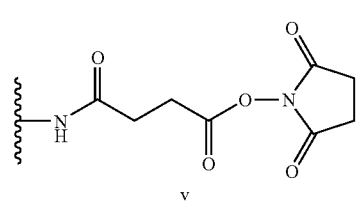
v
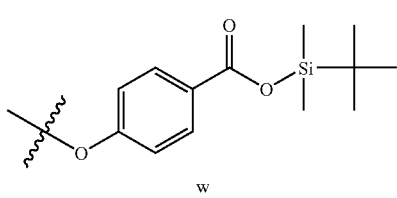
w TABLE 5a-continued
Representative R¹ Groups
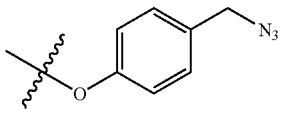
x
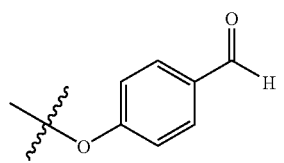
y
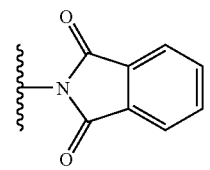
z
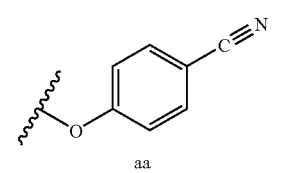
aa
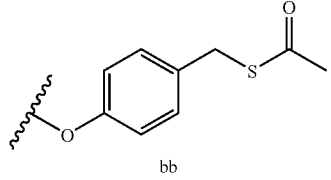
bb
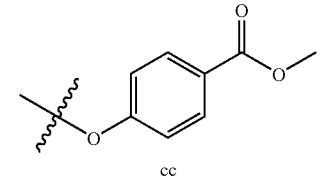
cc
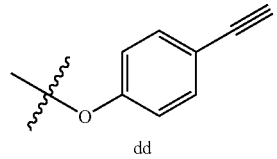
dd
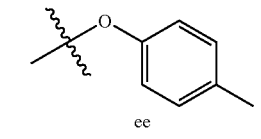
ee
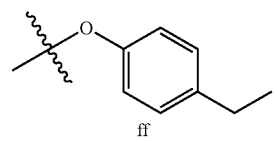
ff
TABLE 5a-continued
Representative R¹ Groups
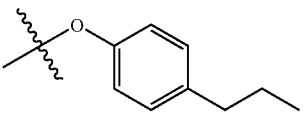
gg
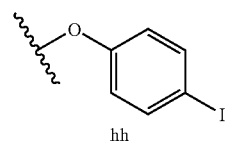
hh
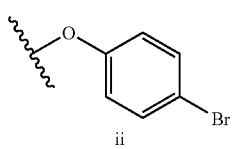
ii
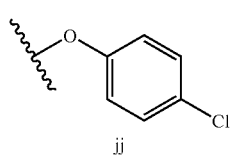
jj
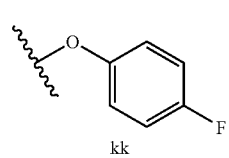
kk
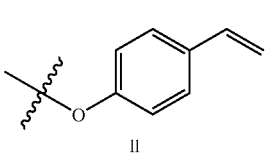
ll
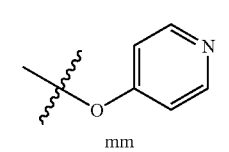
mm
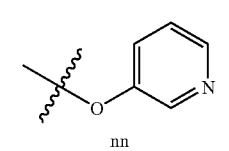
nn
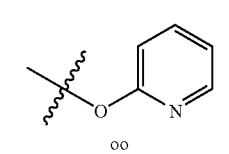
oo
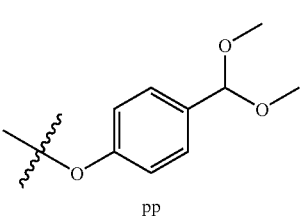
pp TABLE 5a-continued
Representative R[1] Groups
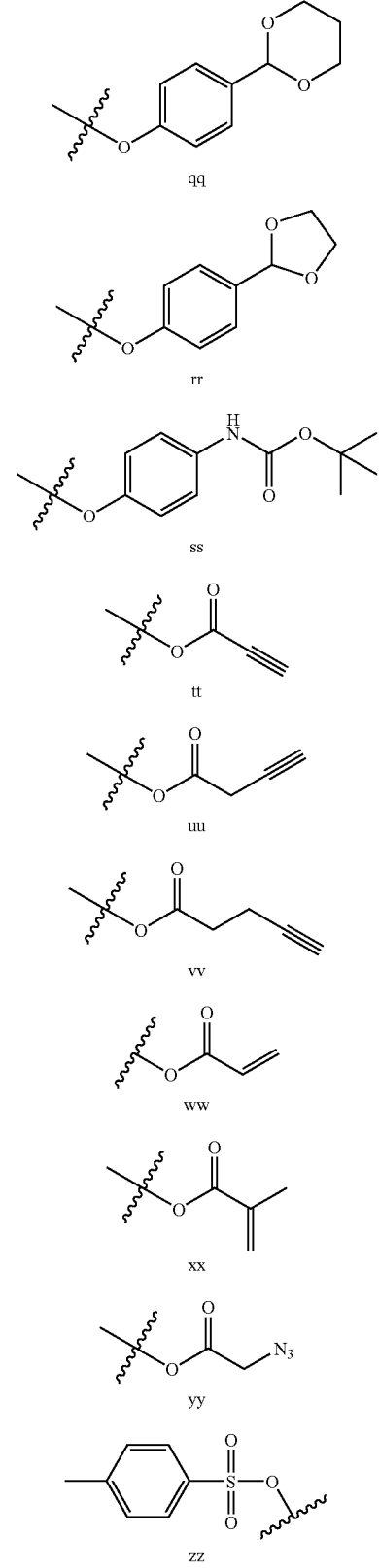
qq, rr, ss, tt, uu, vv, ww, xx, yy, zz
TABLE 5a-continued
Representative R[1] Groups
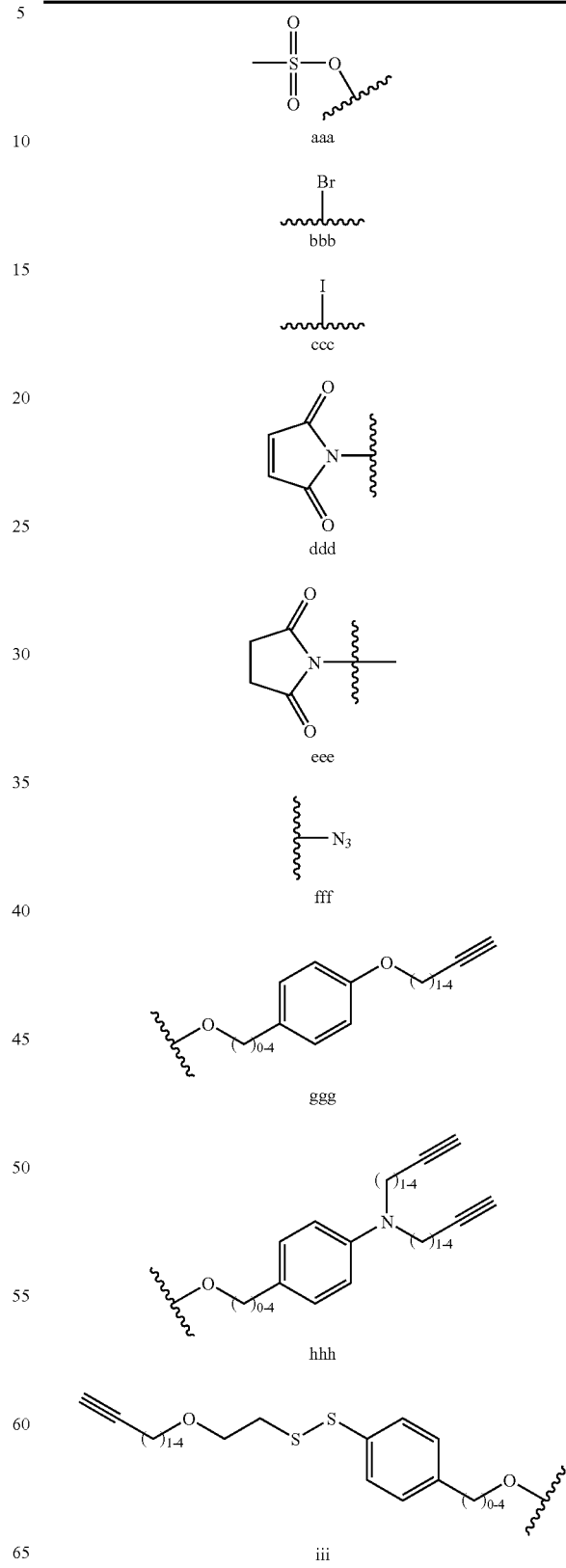
aaa, bbb, ccc, ddd, eee, fff, ggg, hhh, iii

TABLE 5a-continued

Representative R¹ Groups

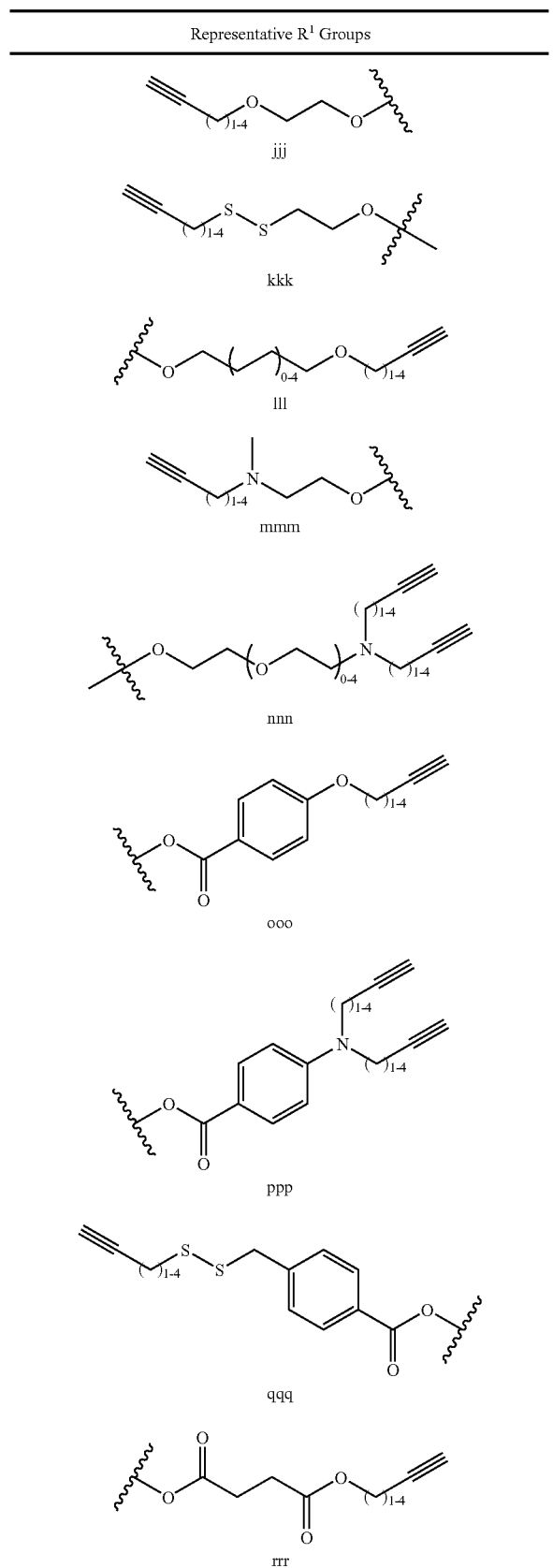

In certain embodiments, the R¹ group of any of formulae I, II, and III is selected from any of those R¹ groups depicted in Table 5, supra. In other embodiments, the R¹ group of any of formulae I, II, and III is group k or l. In yet other embodiments, the R¹ group of any of formulae I, II, and III is n, o, cc, dd, ee, ff hh, h, ii, jj, ll, or uu. In still other embodiments, the R¹ group of any of formulae I, II, and III is h, aa, yy, zz, or aaa.

According to another aspect of the present invention, the R¹ group of any of formulae I, II, and III is q, r, s, t, www, xxx, or yyy.

In other embodiments, the R¹ group of any of formulae I, II, and III is selected from any of those R¹ groups depicted in Tables 1-4, supra.

Exemplary $R^{2a}$ groups of any of formulae I, II, and III are set forth in Table 6, below.

TABLE 6

Representative $R^{2a}$ Groups

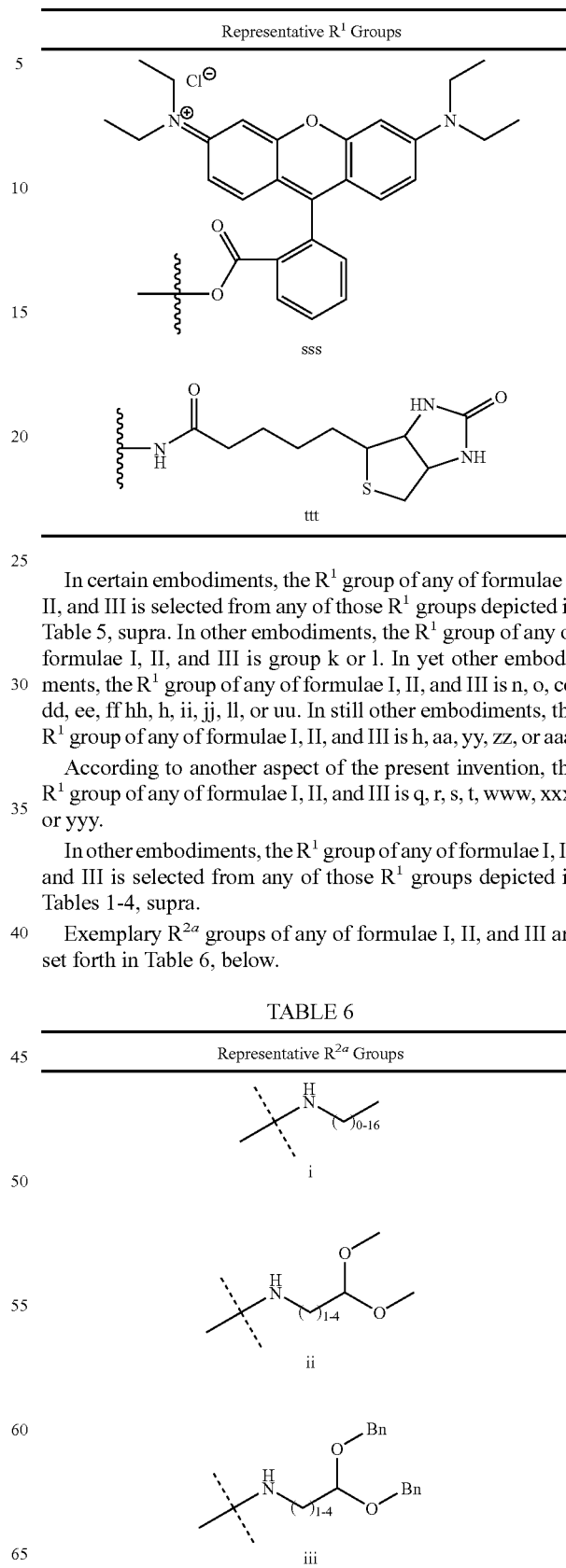

TABLE 6-continued
Representative R²ᵃ Groups
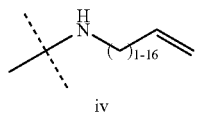
iv
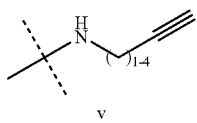
v
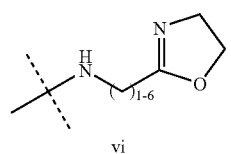
vi
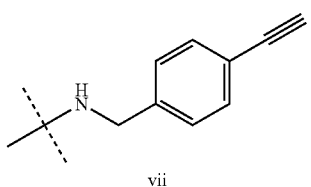
vii
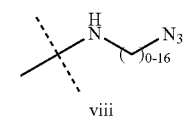
viii
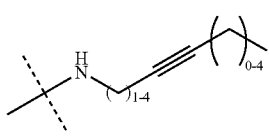
ix
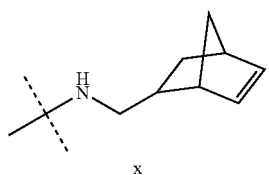
x
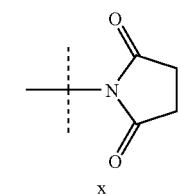
x
xi
TABLE 6-continued
Representative R²ᵃ Groups
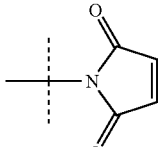
xii
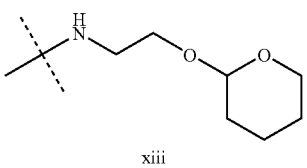
xiii
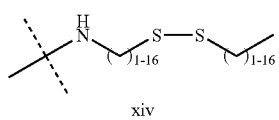
xiv
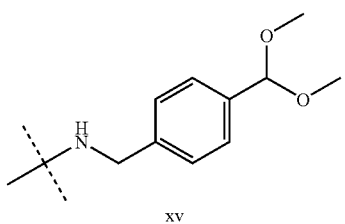
xv
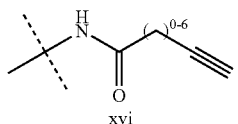
xvi
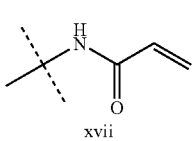
xvii
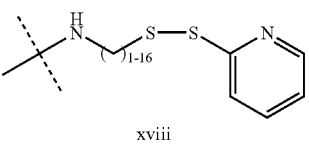
xviii
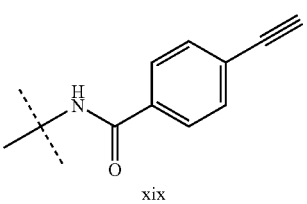
xix
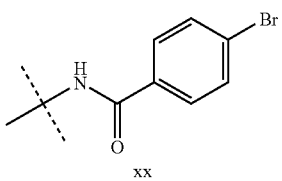
xx TABLE 6-continued
Representative R²ᵃ Groups
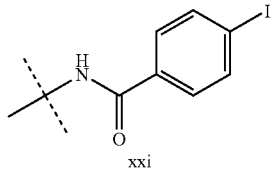
xxi
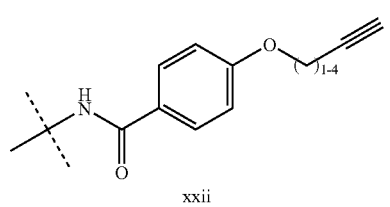
xxii
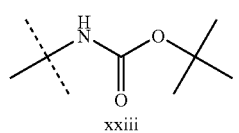
xxiii
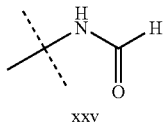
xxiv
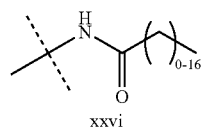
xxv
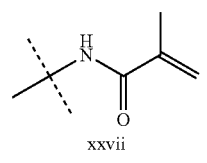
xxvi
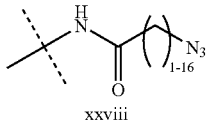
xxvii
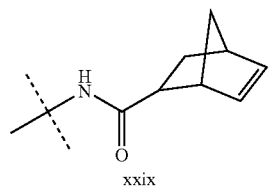
xxviii
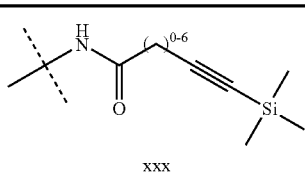
xxix
TABLE 6-continued
Representative R²ᵃ Groups
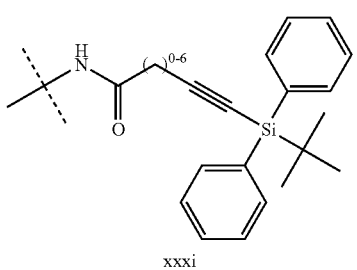
xxx
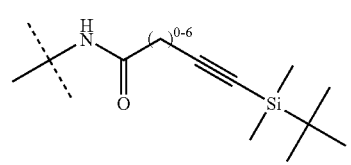
xxxi
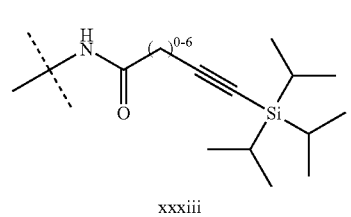
xxxii
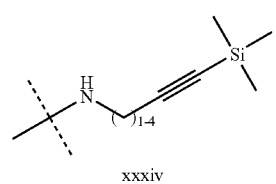
xxxiii
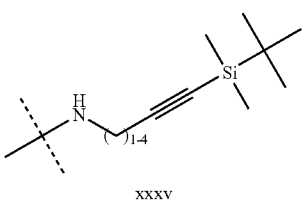
xxxiv
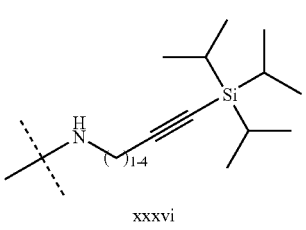
xxxv
xxxvi TABLE 6-continued Representative R²ᵃ Groups

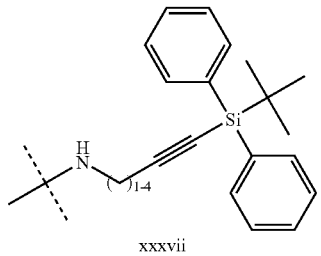

xxxvii

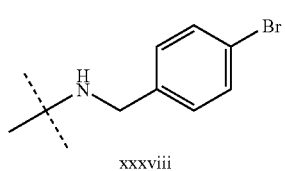

xxxviii

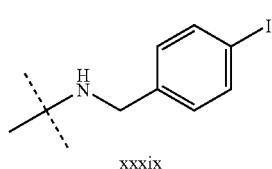

xxxix

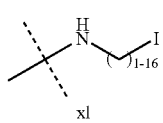

xl

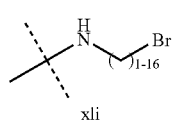

xli

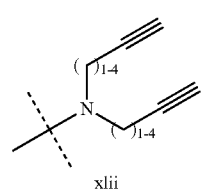

xlii

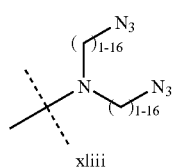

xliii

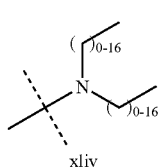

xliv

TABLE 6-continued

Representative R²ᵃ Groups

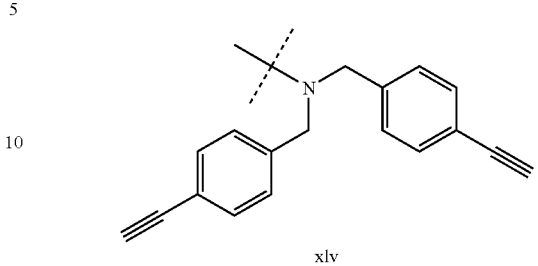

xlv

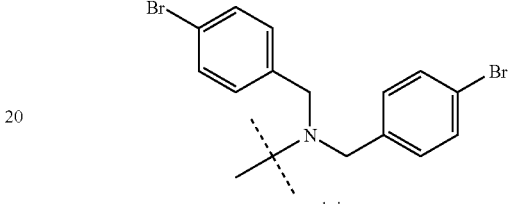

xlvi

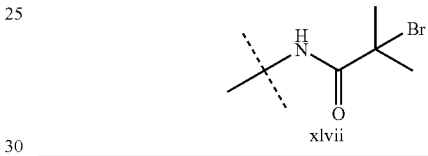

xlvii

In certain embodiments, the R²ᵃ group of any of formulae I, II, and III is selected from any of those R² groups depicted in Table 6, supra. In other embodiments, the R²ᵃ group of any of formulae I, II, and III is group v, viii, xvi, xix, xxii, xxx, xxxi, xxxii, xxxiii, xxxiv, xxxv, xxxvi, xxxvii, or xlii. In yet other embodiments, the R²ᵃ group of any of formulae I, II, and III is xv, xviii, xx, xxi, xxxviii, or xxxix. In certain embodiments, the R²ᵃ group of any of formulae I, II, and III is xxxiv.

According to another embodiment, the R²ᵃ group of any of formulae I, II, and III is selected from any of those R²ᵃ groups depicted in Tables 1-4, supra.

One of ordinary skill in the art would recognize that certain R²ᵃ groups depicted in Table 6 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 6 are also contemplated. According to another embodiment, the R²ᵃ group of any of formulae I, II, and III is selected from a deprotected group of Table 6.

C. Peptide Encapsulation

As described generally above, the present invention provides a micelle having an amyloid-beta (1-42) peptide, or a fragment thereof, encapsulated therein, comprising a multiblock copolymer which comprises a polymeric hydrophilic block and a polymeric hydrophobic block.

In certain embodiments, the present invention provides a micelle, having an amyloid-beta (1-42) peptide, or a fragment thereof, encapsulated therein, comprising a multiblock copolymer which comprises a polymeric hydrophilic block, optionally a poly(amino acid block) that is optionally crosslinkable or crosslinked, and another poly(amino acid) block, characterized in that said micelle has an inner core, optionally a crosslinkable or crosslinked outer core, and a hydrophilic shell. As described herein, micelles of the present invention can be loaded with any such beta-amyloid (1-42) peptide, or fragment thereof.

In certain embodiments, the present invention provide a micelle having an amyloid-beta (1-42) peptide, or a fragment thereof, encapsulated therein, comprising a multiblock copolymer which comprises a polymeric hydrophilic block, optionally a poly(amino acid block) that is optionally crosslinkable or crosslinked, and another poly(amino acid) block, characterized in that said micelle has an inner core, optionally a crosslinkable or crosslinked outer core, and a hydrophilic shell.

In other embodiments, the present invention provide a micelle having an amyloid-beta (1-42) peptide fragment encapsulated therein, comprising a multiblock copolymer which comprises a polymeric hydrophilic block, optionally a poly(amino acid) block) that is optionally crosslinkable or crosslinked, and another poly(amino acid) block, characterized in that said micelle has an inner core, optionally a crosslinkable or crosslinked outer core, and a hydrophilic shell.

As used herein, the phrase "amyloid-beta (1-42) peptide" means a wild-type or mutant amyloid-beta (1-42) peptide. Such mutant amyloid-beta (1-42) peptides are well known in the art. In certain embodiments, mutant amyloid-beta (1-42) peptides include Flemish type and Dutch type mutations and mixtures thereof. However, other mutant amyloid-beta (1-42) peptides are possible and are therefore contemplated for encapsulation in accordance with the present invention. Such peptides are well known to one of ordinary skill in the art and include those described in, e.g., U.S. Pat. No. 7,175,828.

The phrase "amyloid-beta (1-42) peptide fragment," as used herein, refers to fragments of amyloid-beta peptide, residues 1 to 42. Such fragments are known to one of ordinary skill in the art and include wild-type and mutant amyloid-beta fragments. In certain embodiments, an amyloid-beta (1-42) peptide fragment for encapsulating in micelles of the present invention is selected from any one or more of amyloid-beta (1-28), (1-38), (1-39), (29-42), and (1-37). In other embodiments, the amyloid-beta (1-42) peptide fragment is amyloid-beta (21-30) or (12-28). It has been reported that in patients with Alzheimer's disease, extracellular amyloid plaque core is primarily composed of beta (1-42), whereas cerebrovascular amyloid contains the more soluble beta (1-39). It has been suggested that the fragment beta(29-42) directs the folding of the complete beta (1-42) peptide to produce the beta-pleated sheet found in amyloid plaques.

In other embodiments, an amyloid-beta (1-42) peptide fragment for encapsulating in micelles of the present invention is selected from any one or more of amyloid-beta (1-12), (1-20), (1-40), (10-20), (12-28), (17-28), (17-40), (22-35), (25-35), (32-35), (34-42), and (10-35). Such fragments are commercially available from, e.g., Sigma Aldrich.

In certain embodiments, an amyloid-beta (1-42) peptide fragment for encapsulating in a micelle of the present invention is any one or more of amyloid-beta (1-16), (1-25), (1-35), (33-40), and (33-42).

Specific amyloid-beta peptide sequences for use in the present invention include:

```
Aβ 1-42 peptide (wild-type)
DAEFRHDSGYEVHHQKLVFFAEDVGSNKGAIIGLMVGGVVIA.            (SEQ ID NO: 1)

Fragments
Aβ 1-35 peptide (wild-type)
DAEFRHDSGYEVHHQKLVFFAEDVGSNKGAIIGLM.                   (SEQ ID NO: 2)

Aβ 1-25 peptide (wild-type)
DAEFRHDSGYEVHHQKLVFFAEDVG.                             (SEQ ID NO: 3)

Aβ 1-16 peptide (wild-type)
DAEFRHDSGYEVHHQK.                                      (SEQ ID NO: 4)

Aβ 33-40 peptide (wild-type)
GLMVGGVV.                                              (SEQ ID NO: 5)

Aβ 33-42 peptide (wild-type)
GLMVGGVVIA.                                            (SEQ ID NO: 6)

Fluorescein-labeled Aβ 1-40 peptide (wild-type)
Fluorescein-NH-DAEFRHDSGYEVHHQKLVFFAEDVGSNKGAIIGLMVGGVV-COOH.  (SEQ ID NO: 7)

Mutants
P24M 1-42 (Aβ 1-42 peptide with mutation at AA 24)
DAEFRHDSGYEVHHQKLVFFAWDMGSNKGAIIGLMVGGVVIA.            (SEQ ID NO: 8)

P24M 1-35 (Aβ 1-35 peptide with mutation at AA 24)
DAEFRHDSGYEVHHQKLVFFAWDMGSNKGAIIGLM.                   (SEQ ID NO: 9)

P24M 1-25 (Aβ 1-25 peptide with mutation at AA 24)
DAEFRHDSGYEVHHQKLVFFAWDMG.                             (SEQ ID NO: 10)

P22W 1-42 (Aβ 1-42 peptide with mutation at AA 22)
DAEFRHDSGYEVHHQKLVFFAWDVGSNKGAIIGLMVGGVVIA.            (SEQ ID NO: 11)

P22W 1-35 (Aβ 1-35 peptide with mutation at AA 22)
DAEFRHDSGYEVHHQKLVFFAWDVGSNKGAIIGLM.                   (SEQ ID NO: 12)

P22W 1-25 (Aβ 1-25 peptide with mutation at AA 22)
DAEFRHDSGYEVHHQKLVFFAWDVG.                             (SEQ ID NO: 13)
```

-continued

PDM 1-42 (Aβ 1-42 peptide with Dutch mutation at AA 22)
DAEFRHDSGYEVHHQKLVFFAQDVGSNKGAIIGLMVGGVVIA. (SEQ ID NO: 14)

PDM 1-35 (Aβ 1-35 peptide with Dutch mutation at AA 22)
DAEFRHDSGYEVHHQKLVFFAQDVGSNKGAIIGLM. (SEQ ID NO: 15)

PDM 1-25 (Aβ 1-25 peptide with Dutch mutation at AA 22)
DAEFRHDSGYEVHHQKLVFFAQDVG. (SEQ ID NO: 16)

PFDM 1-42 (Aβ 1-42 peptide with Flemish (AA 21) and Dutch mutation (AA 22))
DAEFRHDSGYEVHHQKLVFFGQDVGSNKGAIIGLMVGGVVIA. (SEQ ID NO: 17)

PFDM 1-35 (Aβ 1-35 peptide with Flemish (AA 21) and Dutch mutation (AA 22))
DAEFRHDSGYEVHHQKLVFFGQDVGSNKGAIIGLM. (SEQ ID NO: 18)

PFDM 1-25 (Aβ 1-25 peptide with Flemish (AA 21) and Dutch mutation (AA 22)
DAEFRHDSGYEVHHQKLVFFGQDVG. (SEQ ID NO: 19)

3X2F5 (Aβ 1-7 peptide with 5 copies (35 AA peptide))
DAEFRHDDAEFRHDDAEFRHDDAEFRHDDAEFRHD. (SEQ ID NO: 20)

According to another embodiment, the present invention provides a micelle, as described herein, further comprising an additional therapeutic agent useful for treating disorders associated with amyloid-beta (1-42) peptide, or fragment thereof. In certain embodiments, the present invention provides a micelle, as described herein, further comprising an additional therapeutic agent useful for treating Alzheimer's disease such as memantine, Aricept® or Excelon®. It will also be appreciated that micelles of the present invention can be employed in combination therapies, that is, a micelle of the present invention can be administered concurrently with, prior to, or subsequent to, one or more other desired therapeutics or medical procedures. Alternatively or additionally, the present invention provides a micelle, as described herein, wherein said micelle is administered concurrently with, prior to, or subsequent to, one or more therapeutic agent useful for treating Alzheimer's disease. Such additional therapeutic agents include memantine, Aricept® and Excelon®, to name a but a few.

D. Polymer Conjugation

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. Chem. Commun. 2003, 2400-2401; Gabizon, A.; Shmeeda, H.; Horowitz, A. T.; Zalipsky, S. Adv. Drug Deliv. Rev. 2004, 56, 1177-1202; Reynolds, P. N.; Dmitriev, I.; Curiel, D. T. Vector. Gene Ther. 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T J. Nat. Cancer Inst. 2004, 96, 1620-30; Nasongkla, N.; Shuai, X.; Ai, H.,; Weinberg, B. D. P., J.; Boothman, D. A.; Gao, J. Angew. Chem. Int. Ed. 2004, 43, 6323-6327; Jule, E.; Nagasaki, Y.; Kataoka, K. Bioconj. Chem. 2003, 14, 177-186; Stubenrauch, K.; Gleiter, S.; Brinkmann, U.; Rudolph, R.; Lilie, H. Biochem. J. 2001, 356, 867-873; Kurschus, F. C.; Kleinschmidt, M.; Fellows, E.; Dornmair, K.; Rudolph, R.; Lilie, H.; Jenne, D. E. FEBS Lett. 2004, 562, 87-92; and Jones, S. D.; Marasco, W. A. Adv. Drug Del. Rev. 1998, 31, 153-170.

Compounds of any of formulae I, II, and III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of any of formulae I, II, and III to a macromolecule via Click chemistry. Yet another embodiment of the present invention provides a macromolecule conjugated to a compound of any of formulae I, II, and III via the $R^1$ group.

After incorporating the poly(amino acid) block portions into the multi-block copolymer of the present invention resulting in a diblock or triblock copolymer of formula I, II, or III, the other end-group functionality, corresponding to the $R^1$ moiety of any of formulae I, II, and III, can be used to attach targeting groups for cell specific delivery including, but not limited to, attach targeting groups for cell specific delivery including, but not limited to, proteins, oligopeptides, antibodies, monosaccharides, oligosaccharides, vitamins, or other small biomolecules. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopeptides), and vitamins (e.g. folate). Alternatively, the $R^1$ moiety of any of formulae I, II, and III is bonded to a biomolecule, drug, cell, or other suitable substrate.

In other embodiments, the $R^1$ moiety of any of formulae I, II, and III is bonded to biomolecules which promote cell entry and/or endosomal escape. Such biomolecules include, but are not limited to, oligopeptides containing protein transduction domains such as the HIV Tat peptide sequence (GRKKRRQRRR) (SEQ ID NO: 21) or oligoarginine (RRRRRRRRR) (SEQ ID NO: 22). Oligopeptides which undergo conformational changes in varying pH environments such oligohistidine (HHHHH) (SEQ ID NO: 23) also promote cell entry and endosomal escape.

In other embodiments, the $R^1$ moiety of any of formulae I, II, and III is bonded to detectable moieties, such as fluorescent dyes or labels for positron emission tomography including molecules containing radioisotopes (e.g. $^{18}F$) or ligands with bound radioactive metals (e.g. $^{62}Cu$). In other embodiments, the $R^1$ moiety of any of formulae I, II, and III is bonded to a contrast agents for magnetic resonance imaging such as gadolinium, gadolinium chelates, or iron oxide (e.g $Fe_3O_4$ and $Fe_2O_3$) particles. In other embodiments, the $R^1$ moiety of any of formulae I, II, and III is bonded to a semiconducting nanoparticle such as cadmium selenide, cadmium sulfide, or cadmium telluride or bonded to other metal nanoparticles such as colloidal gold. In other embodiments, the $R^1$ moiety of any of formulae I, II, and III is bonded to natural or synthetic surfaces, cells, viruses, dyes, drugs, chelating agents, or used for incorporation into hydrogels or other tissue scaffolds.

In one embodiment, the $R^1$ moiety of any of formulae I, II, and III is an acetylene or an acetylene derivative which is capable of undergoing [3+2] cycloaddition reactions with complementary azide-bearing molecules and biomolecules. In another embodiment, the $R^1$ moiety of any of formulae I, II, and III is an azide or an azide derivative which is capable of undergoing [3+2] cycloaddition reactions with complementary alkyne-bearing molecules and biomolecules (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125, 11782-11783.

In another embodiment, the [3+2] cycloaddition reaction of azide or acetylene-bearing nanovectors and complimentary azide or acetylene-bearing biomolecules are transition metal catalyzed. Copper-containing molecules which catalyze the "click" reaction include, but are not limited to, copper bromide (CuBr), copper chloride (CuCl), copper sulfate ($CuSO_4$), copper iodide (CuI), $[Cu(MeCN)_4](OTf)$, and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In another embodiment, the $R^1$ moiety of any of formulae I, II, and III is an hydrazine or hydrazide derivative which is capable of undergoing reaction with biomolecules containing aldehydes or ketones to form hydrazone linkages. In another embodiment, the $R^1$ moiety of any of formulae I, II, and III is an aldehyde or ketone derivative which is capable of undergoing reaction with biomolecules containing a hydrazine or hydrazide derivative to form hydrazone linkages.

In another embodiment, the $R^1$ moiety of any of formulae I, II, and III is a hydroxylamine derivative which is capable of undergoing reaction with biomolecules containing aldehydes or ketones. In another embodiment, the $R^1$ moiety of any of formulae I, II, and III is an aldehyde or ketone which is capable of undergoing reaction with biomolecules containing a hydroxylamine, or a hydroxylamine derivative.

In yet another embodiment, the $R^1$ moiety of any of formulae I, II, and III is an aldehyde or ketone derivative which is capable of undergoing reaction with biomolecules containing primary or secondary amines to form imine linkages. In another embodiment, the $R^1$ moiety of any of formulae I, II, and III is a primary or secondary amine which is capable of undergoing reaction with biomolecules containing an aldehyde or ketone functionality to form imine linkages. It will be appreciated that imine linkages can be further converted to stable amine linkages by treatment with a suitable reducing agent (e.g. lithium aluminum hydride, sodium borohydride, sodium cyanoborohydride, etc.)

In yet another embodiment, the $R^1$ moiety of any of formulae I, II, and III is an amine (primary or secondary) or alcohol which is capable of undergoing reaction with biomolecules containing activated esters (e.g. 4-nitrophenol ester, N-hydroxysuccinimide, pentafluorophenyl ester, ortho-pyridylthioester), to form amide or ester linkages. In still other embodiments, the $R^1$ moiety of any of formulae I, II, and III is an activated ester which is capable of undergoing reaction with biomolecules possessing amine (primary or secondary) or alcohols to form amide or ester linkages.

In still other embodiments, the $R^1$ moiety of any of formulae I, II, and III is an amine or alcohol which is bound to biomolecules with carboxylic acid functionality using a suitable coupling agent. In still other embodiments, the $R^1$ moiety of any of formulae I, II, and III is a carboxylic acid functionality which is bound to biomolecules containing amine or alcohol functionality using a suitable coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, the $R^1$ moiety of any of formulae I, II, and III is an electrophile such as maleimide, a maleimide derivative, or a bromoacetamide derivative, which is capable of reaction with biomolecules containing thiols or amines. In another embodiment, the $R^1$ moiety of any of formulae I, II, and III is a nucleophile such as an amine or thiol which is capable or reaction with biomolecules containing electrophilic functionality such as maleimide, a maleimide derivative, or a bromoacetamide derivative.

In still other embodiments, the $R^1$ moiety of any of formulae I, II, and III is a ortho-pyridyl disulfide moiety which undergoes disulfide exchange with biomolecules containing thiol functionality. In still other embodiments, the $R^1$ moiety of any of formulae I, II, and III is a thiol or thiol derivative which undergoes disulfide exchange with biomolecules containing ortho-pyridyl disulfide functionality. It will be appreciated that such exchange reactions result in a disulfide linkage which is reversible in the presence of a suitable reducing agent (e.g. glutathione, dithiothreitol (DTT), etc.).

In certain embodiments, micelles of the present invention are mixed micelles comprising one or more compounds of formula I, II, or III. It will be appreciated that mixed micelles having different $R^1$ groups, as described herein, can be conjugated to multiple other compounds and/or macromolecules. For example, a mixed micelle of the present invention can have one $R^1$ group suitable for Click chemistry and another $R^1$ group suitable for covalent attachment via a variety of coupling reactions. Such a mixed micelle can be conjugated to different compounds and/or macromolecules via these different $R^1$ groups. Such conjugation reactions are well known to one of ordinary skill in the art and include those described herein.

In certain embodiments, micelles of the present invention are functionalized with immunostimulatory molecules by means of a bioconjugation reaction with functionality present on the micelle surface. Such immunostimulatory molecules may act to enhance the immunogenicity of encapsulated amyloid beta peptides or stimulate antibody production in response to amyloid beta peptides. For example, a micelle of the present invention can have one $R^1$ group suitable for Click chemistry (i.e. azide or alkyne) which can undergo [3+2] cycloaddition with a complimentary (i.e. azide or alkyne) functionalized adjuvant. Immunostimulatory molecules, or adjuvants, are well known in the art and include, but are not limited to, squalene, aluminum salts, QS21, MF59, and sugars and saccharides.

4. General Methods for Providing Micelles of the Present Invention

Multiblock copolymers of the present invention are prepared by methods known to one of ordinary skill in the art and those described in detail in U.S. patent application Ser. No. 11/325,020 filed Jan. 4, 2006, the entirety of which is hereby incorporated herein by reference.

Methods of preparing micelles are known to one of ordinary skill in the art. Micelles can be prepared by a number of different dissolution methods. In the direct dissolution method, the block copolymer is added directly to an aqueous medium with or without heating and micelles are spontaneously formed upon dissolution. The dialysis method is often used when micelles are formed from poorly aqueous soluble copolymers. The copolymer and amyloid-beta (1-42) peptide, or fragment thereof, are dissolved in a water miscible organic solvent such as N-methyl pyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. The peptide-loaded micelles can then be isolated by filtration or lyophilization. Alternatively, the block copolymer and amyloid-beta (1-42) peptide, or fragment thereof, are dissolved in water miscible organic solvent such as N-methyl pyrollidinone, dimethylformamide, dimethylsulfoxide, tetrahydrofuran, or dimethylacetamide and added dropwise to water or another aqueous medium. The micelles can then be isolated by filtration or lyophilization.

In one embodiment, micelles, having an amyloid-beta (1-42) peptide, or fragment thereof, encapsulated therein, possessing carboxylic acid functionality in the outer core are optionally crosslinked by addition of zinc chloride to the micelle solution along with a small amount of sodium bicarbonate to neutralize any hydrochloric acid by-product. In this basic pH environment, the reaction of zinc chloride with the poly(aspartic acid) crosslinking block is rapid and irreversible.

In another embodiment, micelles, having an amyloid-beta (1-42) peptide, or fragment thereof, encapsulated therein, possessing amine functionality in the outer core are optionally crosslinked by the addition of a bifunctional, or multifunctional aldehyde-containing molecule which forms pH-reversible imine crosslinks. In another embodiment, micelles, having an amyloid-beta (1-42) peptide, or fragment thereof, encapsulated therein, possessing aldehyde functionality in the outer core are optionally crosslinked by the addition of a bifunctional, or multi-functional amine-containing molecule which forms pH-reversible imine crosslinks.

In another embodiment, micelles, having an amyloid-beta (1-42) peptide, or fragment thereof, encapsulated therein, possessing alcohol or amine functionality in the outer core are optionally crosslinked by the addition of a bifunctional, or multi-functional carboxylic acid-containing molecules and a coupling agent to form amide or ester crosslinks. In yet another embodiment, micelles, having an amyloid-beta (1-42) peptide, or fragment thereof, encapsulated therein, possessing carboxylic acid functionality in the outer core are optionally crosslinked by the addition of a bifunctional, or multi-functional amine or alcohol-containing molecules and a coupling agent to form amide or ester crosslinks. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, micelles, having an amyloid-beta (1-42) peptide, or fragment thereof, encapsulated therein, possessing aldehyde or ketone functionality in the outer core are optionally crosslinked by the addition of a bifunctional, or multifunctional hydrazine or hydrazide-containing molecule to form pH-reversible hydrazone crosslinks. In still other embodiments, micelles, having an amyloid-beta (1-42) peptide, or fragment thereof, encapsulated therein, hydrazine or hydrazide-functionality in the outer core are optionally crosslinked by the addition of a bifunctional, or multifunctional aldehyde or ketone-containing molecule to form pH-reversible hydrazone crosslinks.

In another embodiment, micelles, having an amyloid-beta (1-42) peptide, or fragment thereof, encapsulated therein, possessing thiol functionality in the outer core are optionally crosslinked by the addition of an oxidizing agent (e.g. metal oxides, halogens, oxygen, peroxides, ozone, peroxyacids, etc.) to form disulfide crosslinks. It will be appreciated that disulfide crosslinks are reversible in the presence of a suitable reducing agent (e.g. glutathione, dithiothreitol (DTT), etc.).

In yet another embodiment, micelles, having an amyloid-beta (1-42) peptide, or fragment thereof, encapsulated therein, possessing both carboxylic acid and thiol functionality in the outer core can be dual crosslinked by the addition of an oxidizing agent (e.g. metal oxides, halogens, oxygen, peroxides, ozone, peroxyacids, etc.) to form disulfide crosslinks followed by the addition of zinc chloride to the micelle solution along with a small amount of sodium bicarbonate to neutralize any hydrochloric acid by-product. It will be appreciated that such a dual-crosslinked micelle is reversible only in the presence of acid and a reducing agent (e.g. glutathione, dithiothreitol (DTT), etc.).

According to another aspect, the present invention provides a method for preparing a micelle, having an amyloid-beta (1-42) peptide, or fragment thereof, encapsulated therein, comprising a multiblock copolymer which comprises a polymeric hydrophilic block, a poly(amino acid block) that is optionally crosslinkable or crosslinked, and another poly (amino acid) block, characterized in that said micelle has an inner core, optionally a crosslinkable or crosslinked outer core, and a hydrophilic shell, said method comprising the steps of:

(a) providing a multiblock copolymer of formula I:

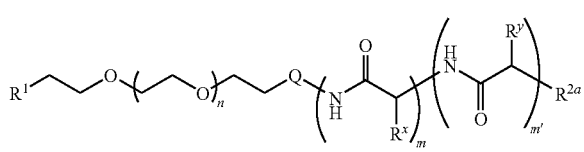

wherein:
n is 10-2500;
m is 0 to 1000;
m' is 1 to 1000;
$R^x$ is a natural or unnatural amino acid side-chain group;
$R^y$ is a hydrophobic or ionic, natural or unnatural amino acid side-chain group;
$R^1$ is $-Z(CH_2CH_2Y)_p(CH_2)_tR^3$, wherein:
  Z is $-O-$, $-S-$, $-C\equiv C-$, or $-CH_2-$;
  each Y is independently $-O-$ or $-S-$;
  p is 0-10;
  t is 0-10; and
  $R^3$ is $-N_3$, $-CN$, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ hydrocarbon chain, wherein 0-6 methylene units of Q are independently replaced by -Cy-, $-O-$, $-NH-$, $-S-$, $-OC(O)-$, $-C(O)O-$, $-C(O)-$, $-SO-$, $-SO_2-$, $-NHSO_2-$, $-SO_2NH-$, $-NHC(O)-$, $-C(O)NH-$, $-OC(O)NH-$, or $-NHC(O)O-$, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, $-N(R^4)_2$, $-NR^4C(O)R^4$, $-NR^4C(O)N(R^4)_2$, $-NR^4C(O)OR^4$, or $-NR^4SO_2R^4$; and
each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, (b) combining said compound of formula I with an amyloid-beta (1-42) peptide, or fragment thereof, and
(c) optionally treating the resulting micelle with a crosslinking reagent to crosslink $R^x$.

In one embodiment, an amyloid-beta (1-42) peptide, or fragment thereof, is loaded into the micelle inner core by adding an aliquot of a copolymer solution in water to the peptide to be incorporated. For example, a stock solution of the peptide in a polar organic solvent is made and allowed to evaporate, and then the copolymer/water solution is added. In another embodiment, the peptide is incorporated using an oil in water emulsion technique. In this case, the peptide is dissolved in an organic solvent and added dropwise to the micelle solution in water, and the peptide is incorporated into the micelle during solvent evaporation. In another embodiment, the peptide is dissolved with the copolymer in a common polar organic solvent and dialyzed against water or another aqueous medium. See Allen, C.; Maysinger, D.; Eisenberg A. *Colloid Surface B* 1999, 16, 3-27.

5. Uses, Methods, and Compositions

Amyloid-beta peptides have been demonstrated useful as vaccines for amyloid-related disorders. This method for treating amyloid-related disorders, such as Alzheimer's disease, has been called the "amyloid-beta immunotherapy approach." Such vaccines have proven to reduce the formation of amyloid plaques *in vivo* resulting in enhanced cognitive ability. Without wishing to be bound by any particular theory, it is believed that an amyloid-beta peptide (1-42), or fragment thereof, is administered to a patient in order to trigger an immune response against the offending peptide and protecting against disease development. It is believed that the vaccine generates antibodies that bind to amyloid-beta in the brain and enhance its removal from the nervous system.

Alzheimer's disease (AD) is a devastating disease, currently affecting 4.5 million Americans with annual costs estimated to exceed $100 billion. Due to the aging of the population, this number is projected to triple in incidence by 2050, meaning that 16 million Americans could be afflicted if interventions are not found.

There is mounting evidence that amyloid beta peptide, the Aβ 1-42 peptide and Aβ 1-40, deposits found in AD patients' brains, generated from amyloid precursor protein (APP), major etiological factors for AD. See, for example, Walsh, D. M. and D. J. Selkoe, *Deciphering the molecular basis of memory failure in Alzheimer's disease*. Neuron, 2004. 44(1): p. 181-93.

A vaccine study published in 2000 represents a milestone in AD therapeutics. Aβ 1-42 was used as an active vaccine to effectively remove Aβ plaques in the brains of Tg mice. Corresponding behavioral improvements were also observed Morgan, D., et al., *A beta peptide vaccination prevents memory loss in an animal model of Alzheimer's disease*. Nature, 2000. 408(6815): p. 982-5. Passive immunotherapy has also shown results similar to the active Aβ vaccine study Bard, F., et al., *Peripherally administered antibodies against amyloid beta-peptide enter the central nervous system and reduce pathology in a mouse model of Alzheimer disease*. Nat Med, 2000. 6(8): p. 916-9. It is also now clear that antibodies to Aβ 1-42 peptide/protein can effectively inhibit the deposition of Aβ in mouse brains (See Morgan, D., et al.) and this has significantly decreased memory deficits in an APP/PS1 Tg mouse model Dickey, C. A., et al., *Selectively reduced expression of synaptic plasticity-related genes in amyloid precursor protein+presenilin*-1 *transgenic mice.* J Neurosci, 2003. 23(12): p. 5219-26. Given this, there is scientific consensus that immunotherapy targeting Aβ is likely to have therapeutic benefit in treating AD Morgan, D., *Antibody therapy for Alzheimer's disease.* Expert Rev Vaccines, 2003. 2(1): p. 53-9.

Following encouraging results with Tg mice, a human trial using the wild type Aβ peptide (AN1792) as a vaccine was initiated using QS21 as an adjuvant. The study was suspended due to 6% of subjects developing brain inflammation after multiple vaccinations Bayer, A. J., et al., *Evaluation of the safety and immunogenicity of synthetic Abeta42 (AN1792) in patients with AD.* Neurology, 2005. 64(1): p. 94-101; Mathews, P. M. and R. A. Nixon, *Setback for an Alzheimer's disease vaccine: lessons learned.* Neurology, 2003. 61(1): p. 7-8. On the other hand, some clinical benefit was demonstrated in a follow-up study of the same vaccinated subjects, and it is also hypothesized that the adjuvant may itself have caused part or all of the problems. The hope for AD vaccine development is to find a solution to minimize the adverse effects in humans. Our goal is to develop a stronger vaccine candidate designed to avoid the problems associated with currently proposed vaccine therapy.

The Aβ 1-42 peptide (Aβ 42) is highly hydrophobic and "sticky", leading it to aggregate. It will form a dimer, tetramer, and larger oligomers which have been demonstrated to confer severe neuronal toxicity causing high levels of neuronal cell death in human brains. The fibrilization step that proceeds after the formation of the oligomers is also responsible for the inflammation that occurs in the brain of an AD patient Parihar, M. S, and T. Hemnani, *Alzheimer's disease pathogenesis and therapeutic interventions.* J Clin Neurosci, 2004. 11(5): p. 456-67.

Recent research progress indicated that soluble oligomeric Aβ plays very important roles in cognitive impairment in AD patients and in transgenic mouse models, see Kirkitadze, M. D., G. Bitan, and D. B. Teplow, *Paradigm shifts in Alzheimer's disease and other neurodegenerative disorders: the emerging role of oligomeric assemblies.* J Neurosci Res, 2002. 69(5): p. 567-77. Also, antibody against oligomeric Aβ has been shown as therapeutic function in AD mouse model, see Chauhan, N. B., *Intracerebroventricular passive immunization with anti-oligoAbeta antibody in TgCRND8.* J Neurosci Res, 2007. 85(2): p. 451-63. Thus a vaccine targeting this toxic Aβ will have less adverse effect and have great therapeutic potential.

Polymers have been widely used in drug delivery systems, and several biocompatible polymers are approved for clinical use by the United States Food and Drug Administration (FDA). Polymer formulations of vaccines have also been investigated for a number of years, aiming to enhance the potency of single-dose vaccines. A polymer formulation AD vaccine delivery system would eliminate the need for an adjuvant, thus avoiding the complications associated with the use of adjuvants. In addition, and without wishing to be bound by any particular theory, it is believed that encapsulation can effectively inhibit the aggregation and generate the same or a better immunoresponse without inducing inflammation. Moreover, it is believed that a provided encapsulated amyloid-beta peptide will address two of the major deficiencies with current AD vaccines: a) the strong T cell response caused by the T cell epitope and aggregation of the Aβ 1-42 peptide, and b) the inflammation caused by both the Aβ aggregation and the adjuvant administered.

In certain embodiments, administration of encapsulated amyloid-beta (1-42) peptide, or fragment thereof, in accordance with the present invention will enhance the *in vivo* half-life of such an amyloid-beta peptide vaccine thus minimizing the number of injections (or other mode of administration) required to elicit the desired immunological response. In other embodiments, administration of encapsulated amyloid-beta (1-42) peptide, or fragment thereof, in accordance with the present invention will reduce aggregation of the peptide while inducing the desired immunological response As described herein, micelles of the present invention have encapsulated within them an amyloid-beta (1-42) peptide, or fragment thereof. According to one embodiment, the present invention provides a method for treating amyloidosis comprising administering to a patient a micelle, having an amyloid-beta (1-42) peptide, or fragment thereof, encapsulated therein, comprising a multiblock copolymer which comprises a polymeric hydrophilic block, a poly(amino acid) block that is optionally crosslinkable or crosslinked, and another poly (amino acid) block, characterized in that said micelle has an inner core, optionally a crosslinkable or crosslinked outer core, and a hydrophilic shell.

As used herein, the term "amyloidosis" refers to a disorder associated with amyloid plaques. In certain embodiments, the amyloidosis is Alzheimer's disease, Parkinson's disease, or Huntington's disease.

In certain embodiments, the present invention provides a method for treating Alzheimer's disease comprising administering to a patient a micelle, having an amyloid-beta (1-42) peptide, or fragment thereof, encapsulated therein, comprising a multiblock copolymer which comprises a polymeric hydrophilic block, a poly(amino acid) block that is optionally crosslinkable or crosslinked, and another poly(amino acid) block, characterized in that said micelle has an inner core, optionally a crosslinkable or crosslinked outer core, and a hydrophilic shell.

Methods for testing the effectiveness of such micelles, peptides, and compositions as described herein are well known to one of ordinary skill in the art and include those described in detail in the Examples, infra.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated amyloid-beta (1-42) peptide, or fragment thereof, are contemplated by the present invention. In certain embodiments, a patient is administered a micelle of the present invention wherein the dosage of amyloid-beta (1-42) peptide, or fragment thereof, is equivalent to what is typically administered for that peptide. In other embodiments, a patient is administered a micelle of the present invention wherein the dosage of amyloid-beta (1-42) peptide, or fragment thereof, is lower than is typically administered for that peptide.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXEMPLIFICATION

Example 1

Peptide Encapsulation

Peptides were dissolved in pure DMSO at 10 mg/ml, then diluted to 1 mg/ml with 1×PBS and then mixed with polymer at 10% (w/w). This mixture was processed for encapsulation with standard protocol.

Example 1a

Encapsulated Aβ 1-25 Peptide (Wild-type)—"EnCF1"

5.0 mg of Aβ 1-25 peptide (SEQ ID NO: 3) was combined with 45.0 mg of poly(ethylene glycol)$_{225}$-b-poly(aspartic acid)$_{10}$-b-poly(benzyl glutamate)$_{30}$ in a screw-top vial. The peptide and copolymer were dissolved in 11 mL of 30% (v/v) tert-butanol solution in water with stirring. After 30 minutes, a clear, colorless solution was obtained, and stirring was continued for an additional 3 hours. The stirbar was removed and the sample was frozen and lyophilized overnight to obtain a white cake. The white cake could be reconstituted in pure water or phosphate buffer saline to form a clear, colorless solution of polymer micelle-encapsulated peptide.

Example 1b

Encapsulated Aβ 1-35 Peptide (Wild-type)—"EnCF2"

3.0 mg of Aβ 1-35 peptide (SEQ ID NO: 2) was encapsulated using 27.0 mg of poly(ethylene glycol)$_{225}$-b-poly(aspartic acid)$_{10}$-b-poly(benzyl glutamate)$_{30}$ using the method described in Example 1a.

Example 1c

Encapsulated P24M 1-35 (Aβ 1-35 Peptide with Mutation at AA 24)

7.0 mg of P24M 1-35 peptide (SEQ ID NO: 9) was encapsulated using 63.0 mg of poly(ethylene glycol)$_{225}$-b-poly(aspartic acid)$_{10}$-b-poly(benzyl glutamate)$_{30}$ using the method described in Example 1a.

Example 1d

Encapsulated P24M 1-25 (Aβ 1-25 Peptide with Mutation at AA 24)

10.0 mg of P24M 1-25 peptide (SEQ ID NO: 10) was encapsulated using 90.0 mg of poly(ethylene glycol)$_{225}$-b-poly(aspartic acid)$_{10}$-b-poly(benzyl glutamate)$_{30}$ using the method described in Example 1a.

Example 1e

Encapsulated PDM 1-35 (Aβ 1-35 Peptide with Dutch Mutation at AA 22)

10.0 mg of PDM 1-35 peptide (SEQ ID NO: 15) was encapsulated using 90.0 mg of poly(ethylene glycol)$_{225}$-b-poly(aspartic acid)$_{10}$-b-poly(benzyl glutamate)$_{30}$ using the method described in Example 1a.

Example 1f

Encapsulated PDM 1-25 (Aβ 1-25 Peptide with Dutch Mutation at AA 22)

10.0 mg of PDM 1-25 peptide (SEQ ID NO: 16) was encapsulated using 90.0 mg of poly(ethylene glycol)$_{225}$-b-poly(aspartic acid)$_{10}$-b-poly(benzyl glutamate)$_{30}$ using the method described in Example 1a.

Example 1g

Encapsulated P22W 1-35 (Aβ 1-35 Peptide with Mutation at AA 22)

10.0 mg of P22W 1-35 peptide (SEQ ID NO: 12) was encapsulated using 90.0 mg of poly(ethylene glycol)$_{225}$-b-poly(aspartic acid)$_{10}$-b-poly(benzyl glutamate)$_{30}$ using the method described in Example 1a.

Example 1h

Encapsulated P22W 1-25 (Aβ 1-25 Peptide with Mutation at AA 22)

10.0 mg of P22W 1-25 peptide (SEQ ID NO: 13) was encapsulated using 90.0 mg of poly(ethylene glycol)$_{225}$-b-poly(aspartic acid)$_{10}$-b-poly(benzyl glutamate)$_{30}$ using the method described in Example 1a.

Example 1i

Encapsulated PFDM 1-25 (Aβ 1-25 Peptide with Flemish and Dutch Mutation)

6.5 mg of PFDM 1-25 peptide (SEQ ID NO: 19) was encapsulated using 58.5 mg of poly(ethylene glycol)$_{225}$-b- poly(aspartic acid)$_{10}$-b-poly(benzyl glutamate)$_{30}$ using the method described in Example 1a.

Example 1j

Encapsulated 3X2F5 (Aβ 1-7 Peptide with 5 Copies (35 AA Peptide))

5.9 mg of 3X2F5 peptide (SEQ ID NO: 20) was encapsulated using 53.1 mg of poly(ethylene glycol)$_{225}$-b-poly(aspartic acid)$_{10}$-b-poly(benzyl glutamate)$_{30}$ using the method described in Example 1a.

Example 1k

Encapsulated Aβ 1-16 Peptide (Wild-type)

5.0 mg of Aβ 1-16 peptide (SEQ ID NO: 4) was encapsulated using 45.0 mg of poly(ethylene glycol)$_{225}$-b-poly(aspartic acid)$_{10}$-b-poly(benzyl glutamate)$_{30}$ using the method described in Example 1a.

Example 1l

Encapsulated Aβ 1-42 Peptide (Wild-type)

500 μL of a 10 mg/mL solution of Aβ 1-42 peptide (SEQ ID NO: 1) in DMSO (5.0 mg of peptide) was combined with 45.0 mg of poly(ethylene glycol)$_{225}$-b-poly(aspartic acid)$_{10}$-b-poly(benzyl glutamate)$_{30}$ in a screw-top vial. The peptide and copolymer were dissolved in 10.4 mL of a 30% (v/v) tert-butanol solution in water with stirring. After 30 minutes, a slightly cloudy solution was obtained, and stirring was continued for an additional 3 hours. The stirbar was removed and the sample was frozen and lyophilized overnight to obtain a white powder. The powder was redissolved in 10.4 mL of a 30% (v/v) tert-butanol solution in water with stirring. After 30 minutes, a slightly cloudy solution was obtained, and stirring was continued for an additional 3 hours. The stirbar was removed and the sample was frozen and lyophilized overnight to obtain a white cake.

Example 1m

Encapsulated Fluorescein-labeled Aβ 1-40 Peptide (Wild-type)

80 μL of a 1 mg/100 μL solution of Fluorescein-labeled Aβ 1-40 peptide (SEQ ID NO: 7) in DMSO (800.0 μg of peptide) was encapsulated with 45.0 mg of poly(ethylene glycol)$_{225}$-b-poly(aspartic acid)$_{10}$-b-poly(benzyl glutamate)$_{30}$ using the method described in Example 1l.

Example 1n

Encapsulated Aβ 33-40 Peptide (Wild-type)

500 μL of a 10 mg/mL solution of Aβ 33-40 peptide (SEQ ID NO: 5) in DMSO (5.0 mg of peptide) was encapsulated with 45.0 mg of poly(ethylene glycol)$_{225}$-b-poly(aspartic acid)$_{10}$-b-poly(benzyl glutamate)$_{30}$ using the method described in Example 1l.

Example 1o

Encapsulated Aβ 33-42 Peptide (Wild-type)

700 μL of a 6.7 mg/mL solution of Aβ 33-42 peptide (SEQ ID NO: 6) in DMSO (4.7 mg of peptide) was encapsulated with 45.0 mg of poly(ethylene glycol)$_{225}$-b-poly(aspartic acid)$_{10}$-b-poly(benzyl glutamate)$_{30}$ using the method described in Example 1l.

Example 2

Vaccination

Study 1 was conducted using a vaccine comprised of polymer-encapsulated Aβ1-42 as an antigen. There were 2 groups of 3 C57 mice. Groups received their first vaccination at age 14 weeks, and the second vaccination 2 weeks later. Group 1 was vaccinated with the encapsulated Aβ1-42 peptide, and Group 2 was vaccinated with polymer only (control).

Study 2 was conducted using a vaccine made of various polymer-encapsulated Aβ fragments and control. Fragment 1 ("F1") is Aβ1-25 (SEQ ID NO: 3) which contains a partial T cell epitope, fragment 2 ("F2") is Aβ1-35 (SEQ ID NO: 2) which contains entire T cell epitope.

There were 8 groups of female BALB/c mice, with 4 mice in each group (total 32 mice):
Group 1—naked Aβ1-25 (fragment 1, F1)
Group 2—polymer mixed with F1 (F1+P)
Group 3—polymer-encapsulated F1 (EnCF1)
Group 4—naked Aβ1-35 (fragment 2, F2)
Group 5—polymer mixed with F2 (F2+P)
Group 6—polymer-encapsulated F2 (EnCF2)
Group 7—polymer only (P, control)
Group 8—naïve control (no injection)

where each polymer corresponds to the polymer utilized in Example 1, above.

Mice received their first vaccination at age 10 weeks; a second vaccination 2 weeks later, and a final vaccination was administrated 2 weeks after the last injection. Each vaccination was administrated subcutaneously with 100 μg peptide at 1 mg/ml (when peptide was used). Mice were bled 10 days after each injection.

Blood Tissue and Plasma Collection Procedures

Ten days after each injection, mice were bled by submandibular phlebotomy using an 18-gauge needle and collected into an EDTA inclusive tube. Plasma was separated by centrifugation 1500 g for 20 minutes with StatSampler from StatSpin (MA). Isolated plasma was aliquoted and frozen at −80° C. The plasma samples were subjected for antibody detection, epitope mapping, antibody isotyping, and cytokine profiles.

Antibody Titer Determination

Anti-Aβ antibody (6E10) was purchased from Signet Laboratories (Dedham, Mass.) and used as a positive control. Antibody levels post-vaccination were assayed via ELISA using Aβ1-42 peptide as the binding antigen. Briefly, 96 well plates were coated with 50 μl Aβ1-42 in cap-binding complex (CBC) buffer (50 mM sodium carbonate, pH 9.6) at 10 μg/ml. A CBC plate is a plate coated with CBC buffer used as a background detection method in order to correct the non-specific binding of sera to the micro plate. Then, both Aβ and CBC coated plates were incubated overnight at 4° C. After 5 washes, plates were subjected to a blocking step with 180 μl blocking buffer (1×PBS containing 1.5% BSA), and incubated for 1 hour at 37° C. Plates were then washed 5 times with wash buffer, and samples diluted with blocking buffer and added to both Aβ and CBC plates at two-fold serial dilutions starting at 1:100. Samples were incubated at 37° C. for 1 hour, and washed 12 times with wash buffer. HRP-conjugated anti-mouse IgG (Sigma Aldrich) were loaded into each well at a 1:5000 dilution, incubated for 1 hour at 37° C., and then washed 12 times. TMB peroxidase substrate was dissolved in PCB buffer, and 100 µl were added to each well. Colorimetric reactions were stopped with 25 µl 2N $H_2SO_4$. Plates were read at 450 nm/630 nm, and samples with readings 3 times higher than controls were considered positive. The highest dilution was used as the endpoint titer.

Epitope Mapping

Different Aβ peptide fragments (Aβ 1-16, 12-28, 22-35, and 29-42) as well as Aβ1-42 at 20 µg/ml were used to coat a 96-well plate with 50 µl per well. The plate was blocked with 180 µl blocking buffer for 1 hour at 37° C., then washed 5 times with wash buffer. Pre- and post-immune sera were loaded with serials dilutions. The samples were screened by ELISA using the same protocol described above for the titer assay.

Antibody Isotyping

Luminex assay was used for antibody isotyping. To further confirm the inflammation and the contribution of cytokines to Ig subclass switching modulation, we detected Ig isotyping by using the Beadlyte® Mouse Immunoglobulin Isotyping Kit by Upstate Cell Signaling Solutions (Temecula, Calif.), following manufacturer's instructions.

Total Ig isotyping was assayed instead of anti-Aβ-specific antibody because any Ig difference in the same mouse is due to the antigen stimulation. In addition, this method allows the monitoring of overall Ig change pre- and post-vaccination. This method produces an IgG1/IgG2a ratio and this ratio helps to differentiate Th1 or Th2 responses in vaccinated mice. Because IgG1 is driven by IL-4 (Th2), and IgG2a is driven by IFN-γ (Th1), an increase in post-vaccination ratio indicates a Th2 response, and a decrease in post-vaccination ratio indicates a Th1 response.

Cytokine Expression

The cytokine expression profiles were detected using the Bio-Rad Bio-Plex kits (Bio-Rad, catalogue # 171F11181). Samples and standards were prepared using company protocols with the initial concentration of standards ranging from 32 ng/ml to 1.95 pg/ml. Plasma samples were prepared for analysis by diluting 1 volume of the serum sample with 3 volumes of the Bio-Plex mouse sample diluent. Wells on the 96-well filter plate were pre-wetted with 100 µl of Bio-Plex assay buffer. The buffer was removed by vacuum filtration. The multiplex bead-working solution was vortexed for 15 to 20 sec at medium speed, and 50 µl was pipetted into each well. One-hundred (100) µl of Bio-Plex wash buffer was also pipetted into each well, and then removed by vacuum filtration. Fifty (50) µl of diluted standard was added to wells in the first two columns, and sample was added the remaining wells. The plate was covered with aluminum foil and placed onto a microplate shaker. Samples were incubated for 30 minutes at room temperature.

At the end of the incubation, the reagents were removed by vacuum filtration, and plates were washed 3 times. The Bio-Plex detection antibody working solution was vortexed gently and 25 µl was added to each well. The entire plate was then covered with a new sheet of sealing tape, followed by a sheet of foil. The plate was then incubated at room temperature with shaking for 30 minutes. Afterward, the sealing tape was removed and the liquid extracted by vacuum filtration. This was followed by 3 washes, with blotting in between each wash.

Streptavidin-PE was vigorously vortexed, and 50 µl pipetted into each well. The plate was again covered with sealing tape and foil, and then incubated at room temperature with shaking for 10 minutes. After incubation, the sealing tape was again removed, the liquid extracted by vacuum filtration, and 3 wash steps with blotting in between were performed. The beads were then re-suspended in each well with 125 µl of Bio-Plex assay buffer. The plate was again covered with a new sheet of sealing tape and incubated at room temperature with shaking for 30 seconds.

Finally, the plates were read. Because of the naturally-occurring variability of cytokine levels, optical density readings for each cytokine were normalized to a 0-1 scale that was used to compare animal groups.

Immunostaining

To evaluate antibodies generated from BALB/c mice, cross-reaction to human Aβ was evaluated in transgenic (tg) mouse brain tissue. Tg mice were euthanized with an overdose of anesthesia, brain blood was removed by intracardial perfusion, and brain tissue was harvested as per established protocol. Immunostaining assay was completed as previously described by Nilsson, L. N., et al., *Cognitive impairment in PDAPP mice depends on ApoE and ACT-catalyzed amyloid formation*. Neurobiol Aging, 2004. 25(9): p. 1153-67.

Western Blotting

Aβ1-42 was reconstituted with pure DMSO at 5 mg/ml and then further diluted with 1×PBS to 0.0625 µg/µl (aggregated Aβ) with or without Aβ12-28 at 0.0625 µg/µl, and then incubated on shaker at 37° C. for overnight. Load 10 µl of aggregated Aβ1-42, Aβ12-28 inhibited peptide and none-aggregated Aβ1-42 to each lane of Tricine gel (Invitrogen, CA, USA). Gel was transferred onto Nitrocellulose membrane, and then blotted with different antibodies by following the standard protocol.

Example 3

Results

After encapsulation of the Aβ1-42 peptide, the encapsulated peptide became a water soluble reagent. Antibody response after two injections of encapsulated Aβ1-42 peptide are shown in FIG. 1.

Figure 2:
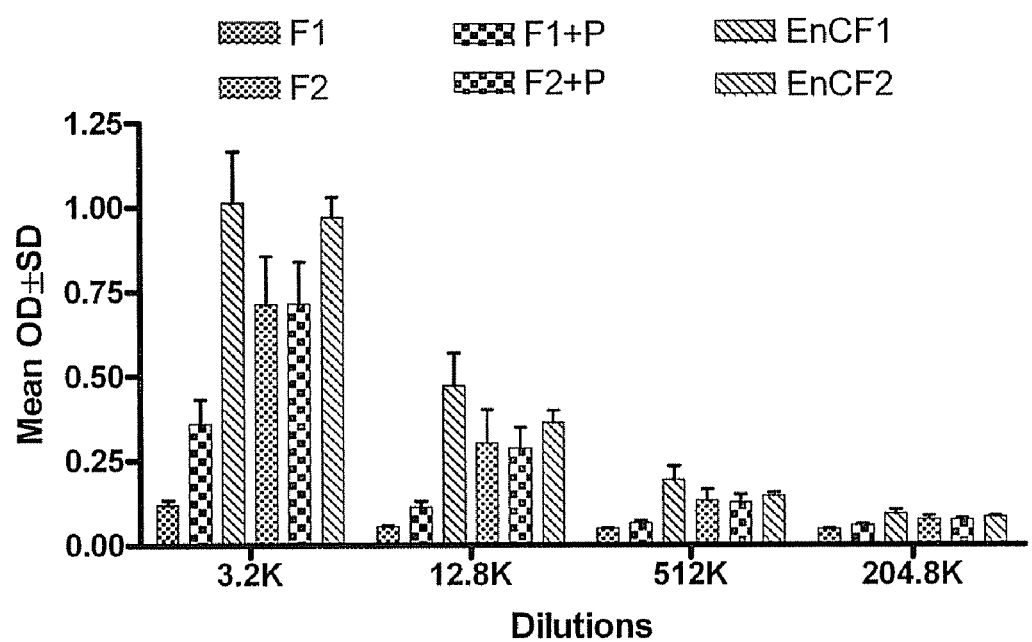
FIG. 2 depicts antibody responses to different vaccine formulae after three injections where antibody titers in sera were collected from BALB/c mice 7 days after third vaccination with encapsulated F1 and F2 peptides (EnCF1 and EnCF2).

FIG. 2 depicts different antibody response to different vaccine formula after three injections where antibody titers in sera were collected from BALB/c mice 7 days after third vaccination with different formulations of Aβ F1 and F2 peptides.

Figure 3:
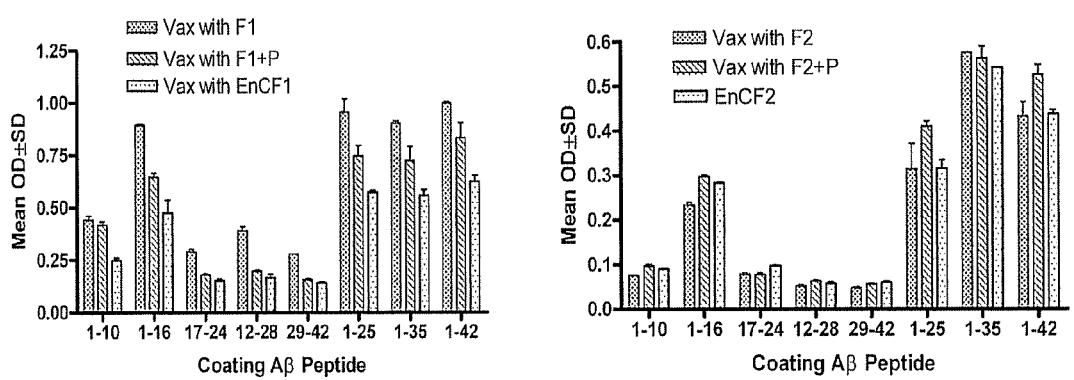
FIG. 3 depicts the results from subjecting EnCF1 and EnCF2 to B cell epitope mapping to determine conformation change post modification.

Encapsulated F1 and F2 peptide fragments ("EnCF1" and "EnCF2") were subjected to B cell epitope mapping to determine conformation change post modification. As depicted in FIG. 3, there was no epitope change observed post vaccination among the tested vaccine formulae.

Figure 4:
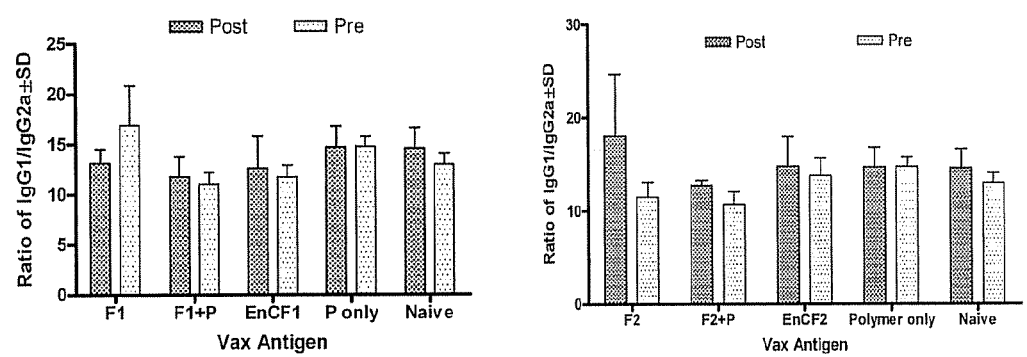
FIG. 4 depicts the results of Ig isotoping pre- and post-vaccination of peptide fragments (F1 and F2), peptide fragments and polymer (F1+P and F2+P), polymer alone (P Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Peptide fragments (F1 and F2), peptide fragments and polymer (F1+P and F2+P), polymer alone (P), and encapsulated peptide fragments (EnCF1 and EnCF2) were assayed for Ig isotyping pre-and post-vaccination as compared to total serum Ig. As depicted in FIG. 4, no significant differences in IgG1/IgG2a ratios the tested formulae were observed when compared pre-versus post-vaccination as compared with naïve control.

Figure 5:
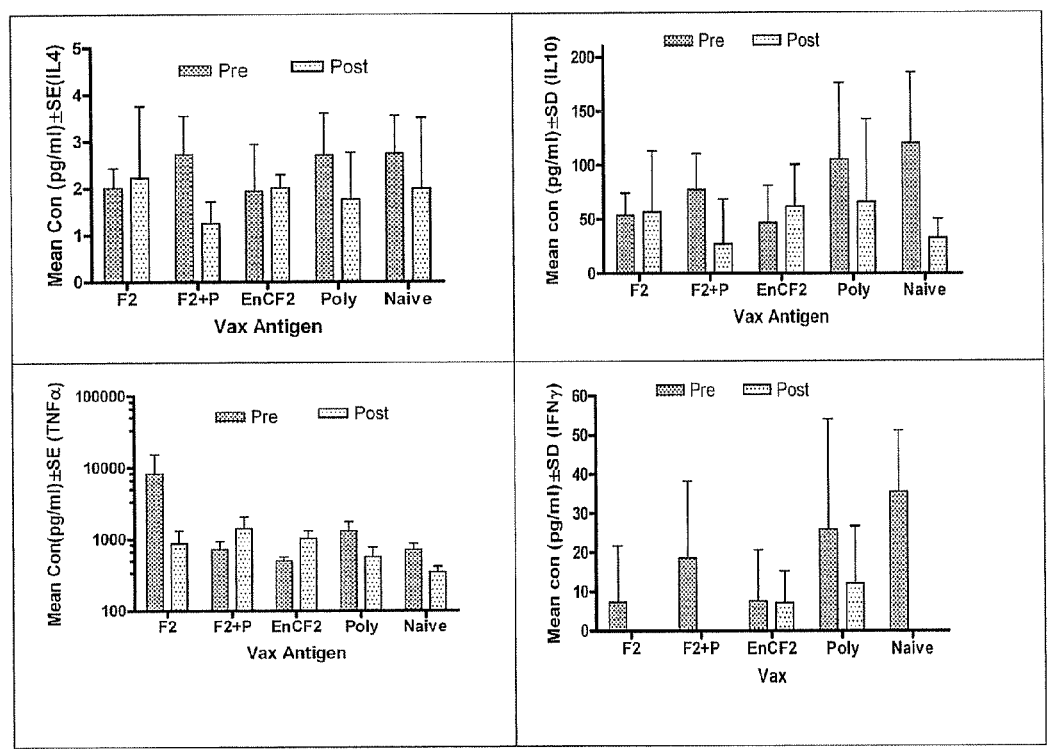

Peptide fragments (F1 and F2), peptide fragments and polymer (F1+P and F2+P), polymer alone (P), and encapsulated peptide fragments (EnCF1 and EnCF2) were analyzed to determine their effect on global inflammation assaying plasma cytokines. As depicted in FIG. 5, no inflammation cytokine increase was observed after vaccination as compared with naïve control.

Figure 6:
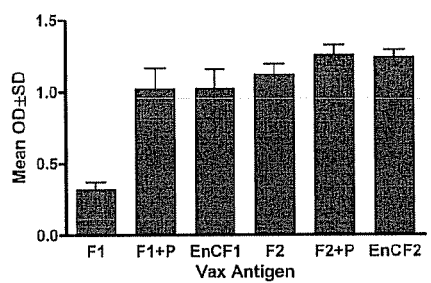
Figure 6:
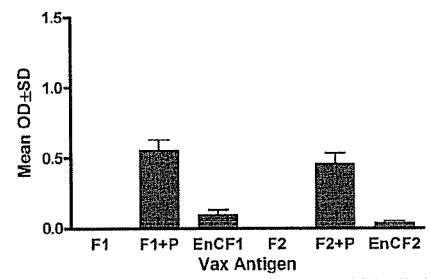

Antibody response to the encapsulation polymer that was tested to identify possible adjuvant effect after five inoculations. As depicted in FIG. 6, no antibody response to the encapsulation polymer was observed against even after 5 vaccinations.

Figure 7:
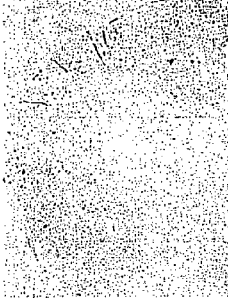
Figure 7:
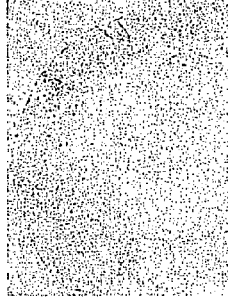
Figure 7:
Figure 7:
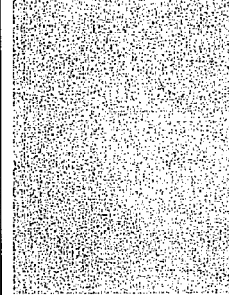
Figure 7:

In order to determine the affinity to human plaque of antibodies generated from encapsulated peptides of the present invention, encapsulated peptides were administered to human APP/PS1 transgenic mice. The brain tissue of these mice was subjected to immunostaining. As depicted in FIG. 7, antibodies generated from polymer encapsulated peptide can recognize Aβ plaque in the brain from human APP/PS1 transgenic mice. In FIG. 7, the following headings are used:

the picture labeled 6E10 is the result of APP/PS1 mouse brain tissue stained with 6E10 antibody;

the picture labeled PCTAD1 is the result of APP/PS1 mouse brain tissue stained with anti-sera from BALB/c mice vaccinated with Aβ1-25 peptide alone;

the picture labeled PCTAD2 is the result of APP/PS1 mouse brain tissue stained with anti-sera from BALB/c mice vaccinated with Aβ1-25 peptide mixed with polymer;

the picture labeled PCTAD3 is the result of APP/PS1 mouse brain tissue stained with anti-sera from BALB/c mice vaccinated with polymer encapsulated Aβ1-25;

the picture labeled PCTAD4 is the result of APP/PS1 mouse brain tissue stained with anti-sera from BALB/c mice vaccinated with Aβ1-35 peptide alone;

the picture labeled with PCTAD5 is the result of APP/PS1 mouse brain tissue stained with anti-sera from BALB/c mice vaccinated with Aβ1-35 peptide mixed with polymer; and the picture labeled with PCTAD6 is the result of APP/PS1 mouse brain tissue stained with anti-sera from BALB/c mice vaccinated with polymer encapsulated Aβ1-35.

Figure 8:
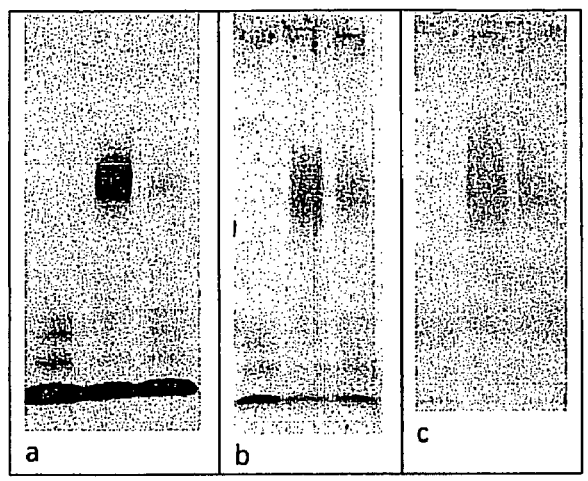

Western blotting results using anti-sera generated from polymer encapsulated peptide indicated that the encapsulated peptides result in more specific recognition of the higher isoform of Aβ (see FIG. 8). FIG. 8 depicts the Western blot result of Aβ1-42 peptide at different aggregation conditions where lane 1 no-aggregated Aβ1-42 peptide; lane 2 overnight aggregated Aβ1-42 peptide; lane 3 is Aβ1-42 mixed with Aβ12-28. 9(a) is blotted with 6E10 antibody; 9(b) is blotted with anti-sera from polymer encapsulated Aβ1-25 peptide vaccine and 9(c) is blotted with polymer encapsulated Aβ1-35 peptide vaccine.

Discussion

The experiments described herein demonstrate that administration of a provided encapsulated amyloid-beta peptide fragment vaccine, in the absence of adjuvant, overcomes many of the adverse effects reported from human AD vaccine clinical trials. FIGS. 1 and 2 show that encapsulated peptide maintained antigenicity but did not cause any inflammatory side effects (FIGS. 3 and 4). It was also shown that provided encapsulated amyloid-beta peptide fragment induced a stronger antibody response than any other formula (FIG. 2). Without wishing to be bound by any particular theory, it is believed that such encapsulation may protect antigen processing and allow for slow release of the antigen. In addition, there was no adjuvant effect seen after administration of provided encapsulated amyloid-beta peptide fragment in vivo and in vitro.

It has been reported that inflammation cytokines are correlated with aging and status of disease. See, for example, Zuliani, G., et al., *Plasma cytokines profile in older subjects with late onset Alzheimer's disease or vascular dementia*. J Psychiatr Res, 2007. 41(8): p. 686-93. Indeed, AD Tg mice have been demonstrated to show both age- and genotyping-dependent inflammation as measured through cytokine response. See, for example Abbas, N., et al., *Up-regulation of the inflammatory cytokines IFN-gamma and IL-12 and down-regulation of IL-4 in cerebral cortex regions of APP(SWE) transgenic mice*. J Neuroimmunol, 2002. 126(1-2): p. 50-7.

Checking global inflammation through cytokine expression is one of the best ways to know what happened and is going to happen when the vaccine was delivered. As discussed above, no global inflammation response was detected (FIG. 5), and no abnormal response was observed in our vaccination study. We therefore use Ig isotyping as a way to evaluate this. Specifically, the ratio of IgG1/IgG2a indirectly determines whether the test vaccine will cause a Th1 or Th2 response. It was surprisingly found that provided encapsulated amyloid-beta peptide fragment shows no preference for either Th1 or Th2 response, and therefore maintains a neutral immune response (FIG. 4).

It was also determined that the antibody generated from BALB/c mice can react to plaque of mouse brain of in APP/PS1 transgenic mouse with human APP gene by immunostaining with anti-sera induced by different vaccine formula. We have tested the recognition of our antibody generated from BALB/c mice to aggregated Aβ peptide by Western blotting. Our result revealed that antibodies generated from the encapsulated peptide have a very specific recognition to oligomeric Aβ (FIG. 8). As depicted in FIG. 8, antibody induced by different size of Aβ peptide fragment has specific reorganization property. For example, encapsulated 1-35 has more specific recognition to aggregated Aβ. The importance of our discovery is that this Aβ conformation specific vaccine will allow us to target on the toxic form of Aβ. Without wishing to be bound by any particular theory, it is believed that this formulation will significantly reduce induction of the autoimmune response because antibody induced by our vaccine was not targeted on the endogenous form of Aβ, but rather targeted an unnatural oligomer of Aβ.

We claim:

1. A micelle having an amyloid (1-42) peptide or fragment or mutant peptide thereof, encapsulated therein, wherein the amyloid-beta (1-42) peptide or fragment or mutant peptide is selected from the group consisting of SEQ ID Nos: 1-20 and wherein the micelle comprises a multiblock copolymer selected from the following compounds of the formula:

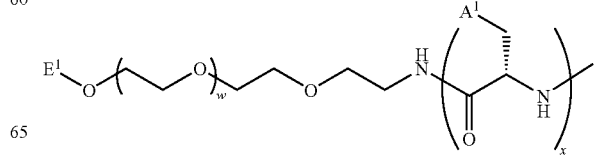

-continued

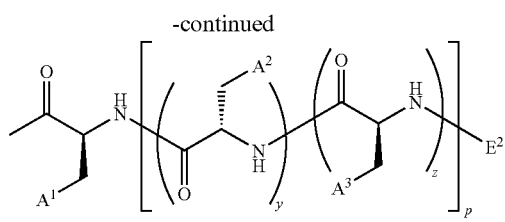

wherein each w is 25-1000, each x is 1-50, each y is 1-50, each z is 1-100, p is the sum of y and z, and each dotted bond represents the point of attachment to the rest of the molecule:

| Compound | A¹ | A² |
|---|---|---|
| 1 | -COOH | phenyl |
| 2 | -COOH | phenyl |
| 3 | -COOH | phenyl |
| 4 | -COOH | phenyl |
| 5 | -COOH | phenyl |
| 6 | -COOH | phenyl |
| 7 | -COOH | phenyl |
| 8 | -COOH | phenyl |
| 9 | -COOH | phenyl |
| 10 | -COOH | phenyl |
| 11 | -SH | phenyl |

-continued

| | A¹ | A² |
|---|---|---|
| 12 | -SH | phenyl |
| 13 | -SH | phenyl |
| 14 | -SH | phenyl |
| 15 | -SH | phenyl |
| 16 | -SH | phenyl |
| 17 | -SH | phenyl |
| 18 | -SH | phenyl |
| 19 | -SH | phenyl |
| 20 | -SH | phenyl |
| 21 | -COOH | phenyl |
| 22 | -COOH | phenyl |
| 23 | -COOH | phenyl |
| 24 | -COOH | phenyl |
| 25 | -COOH | phenyl |

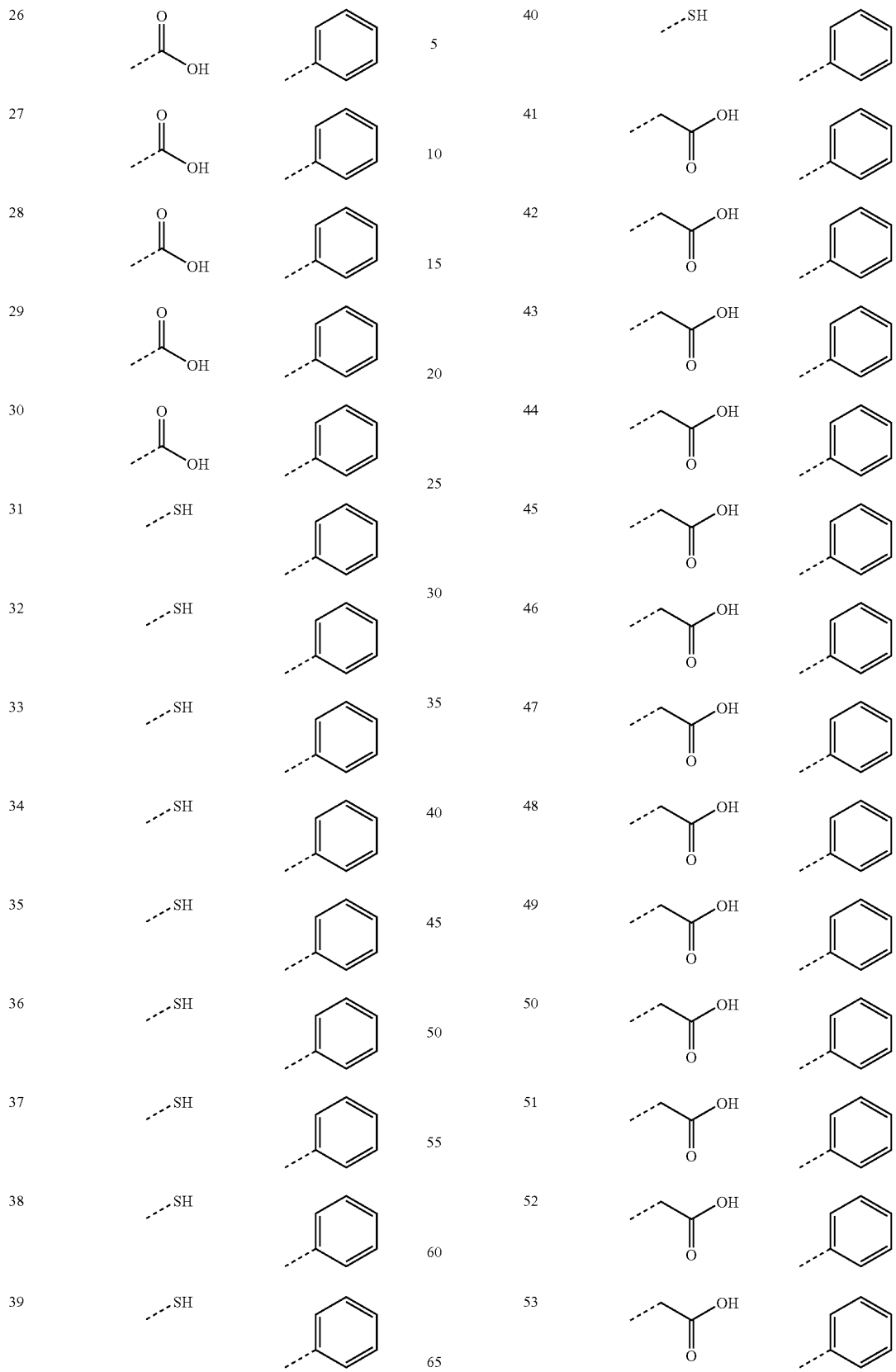

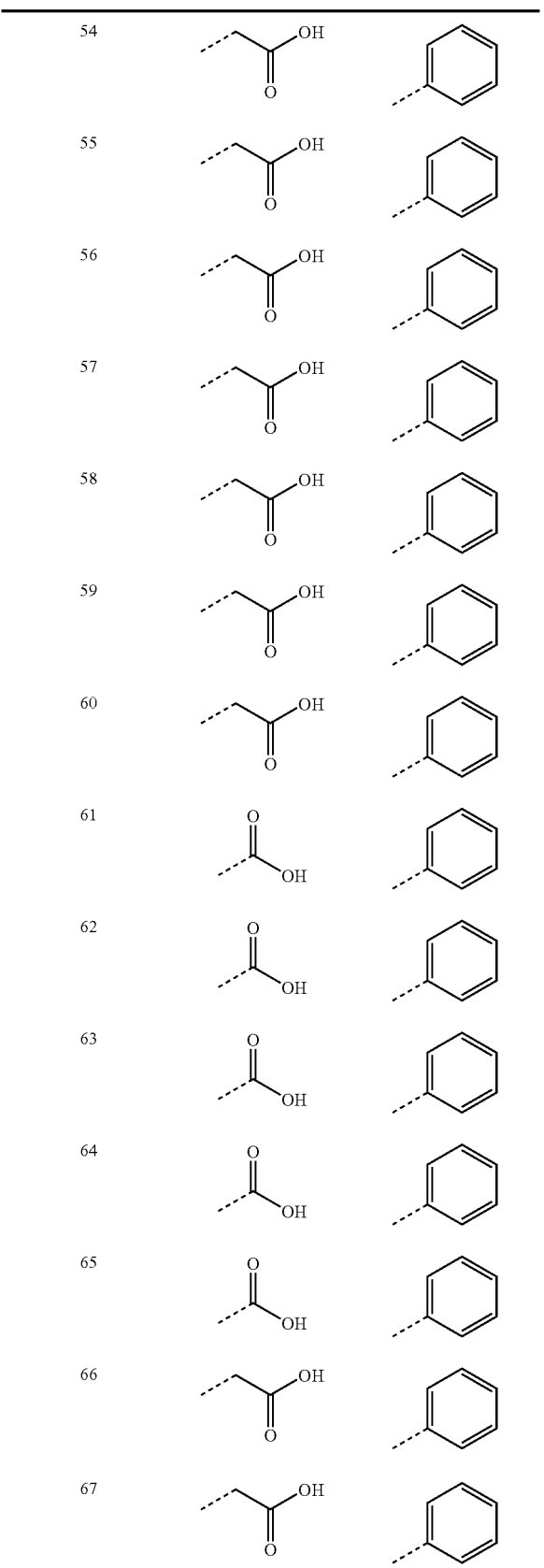
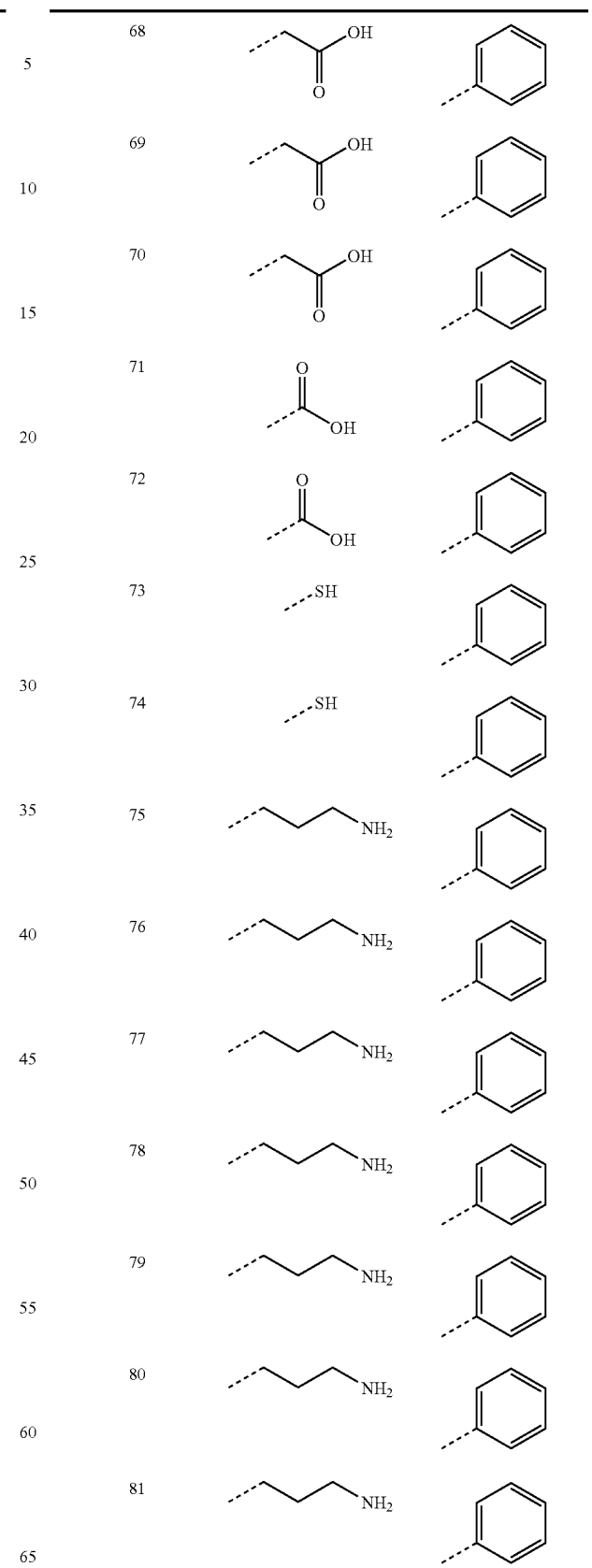

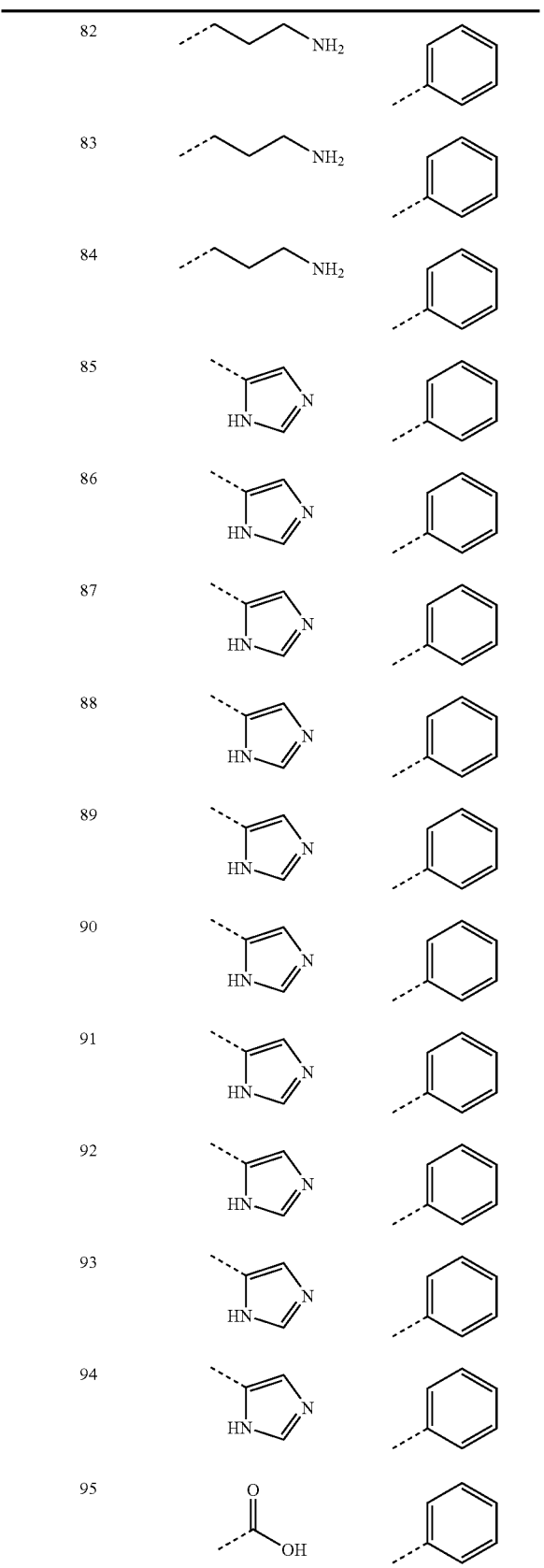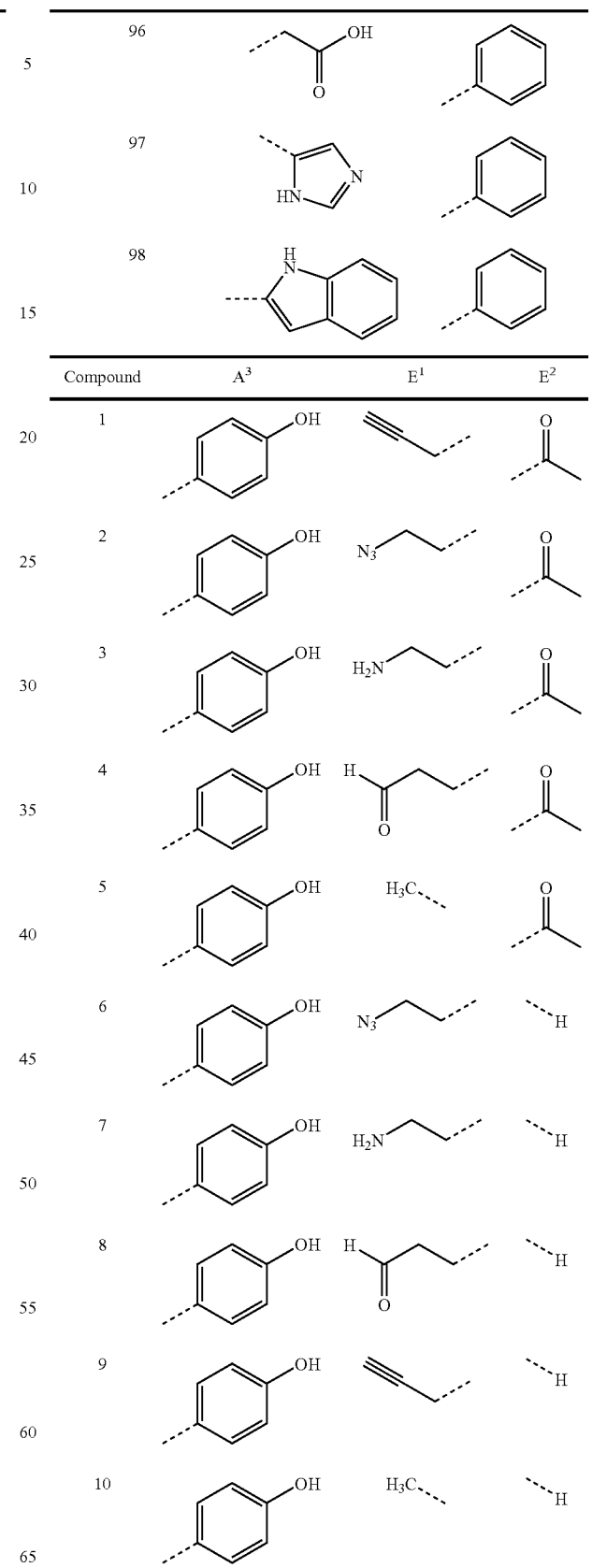

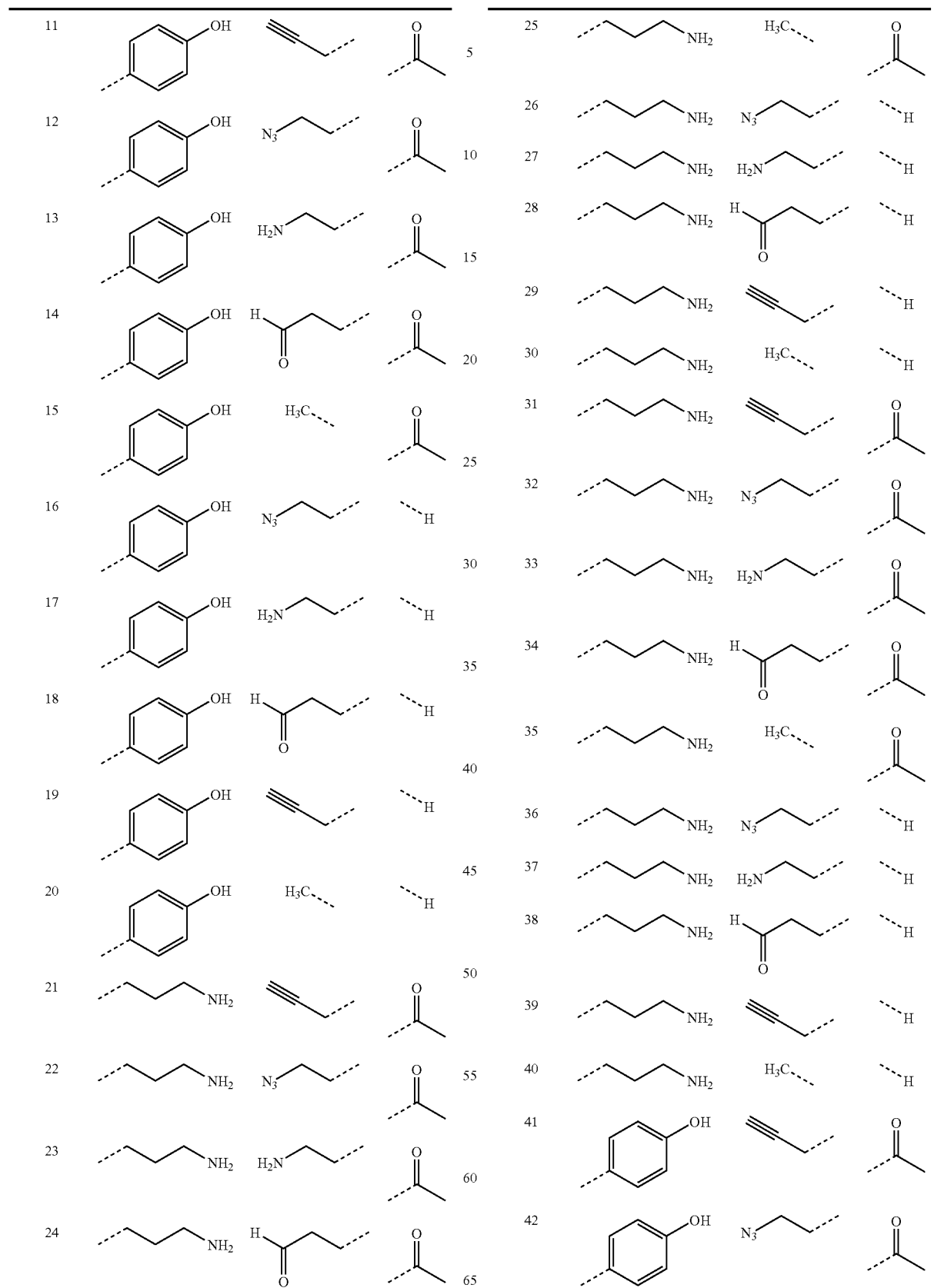

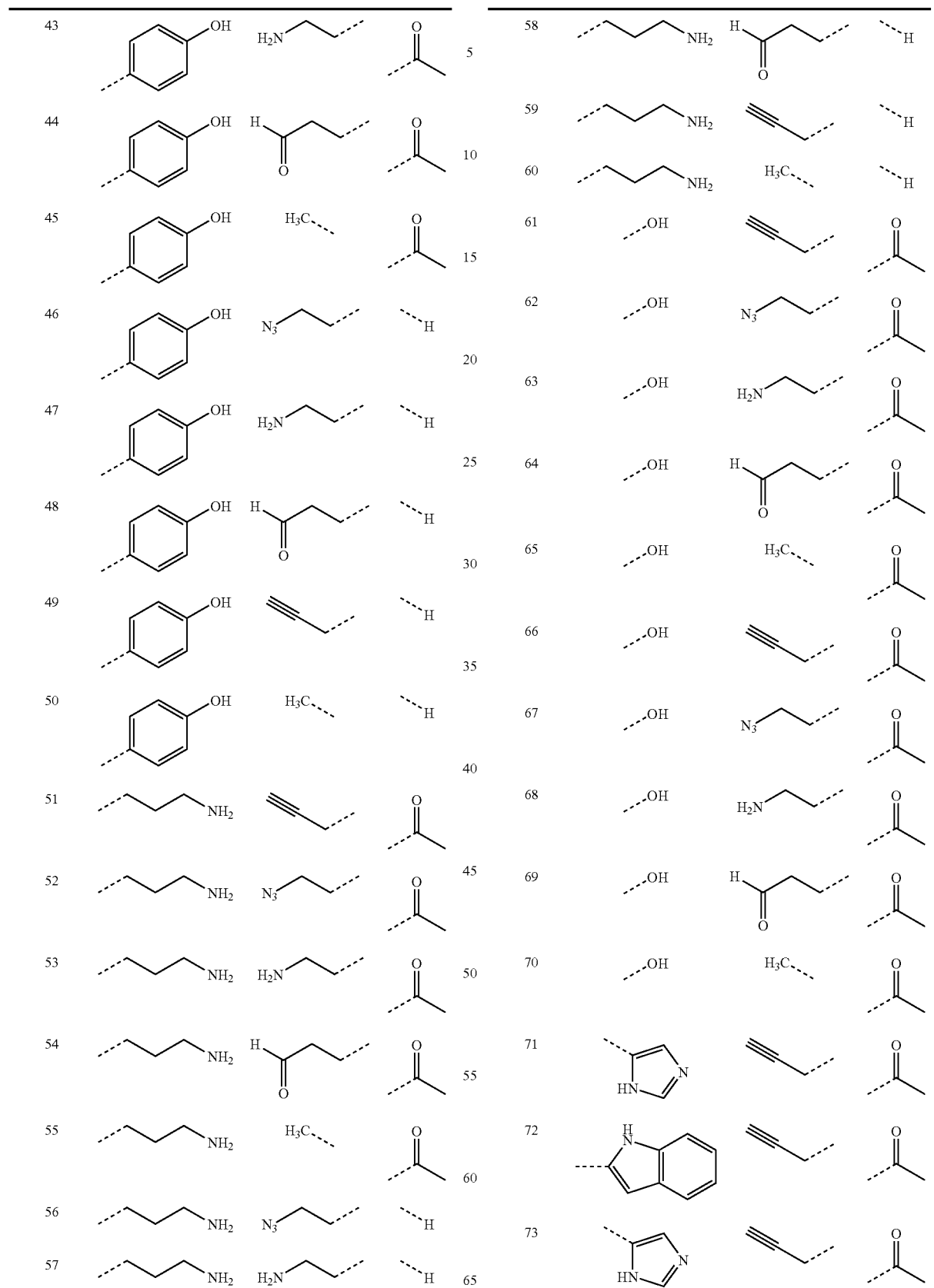

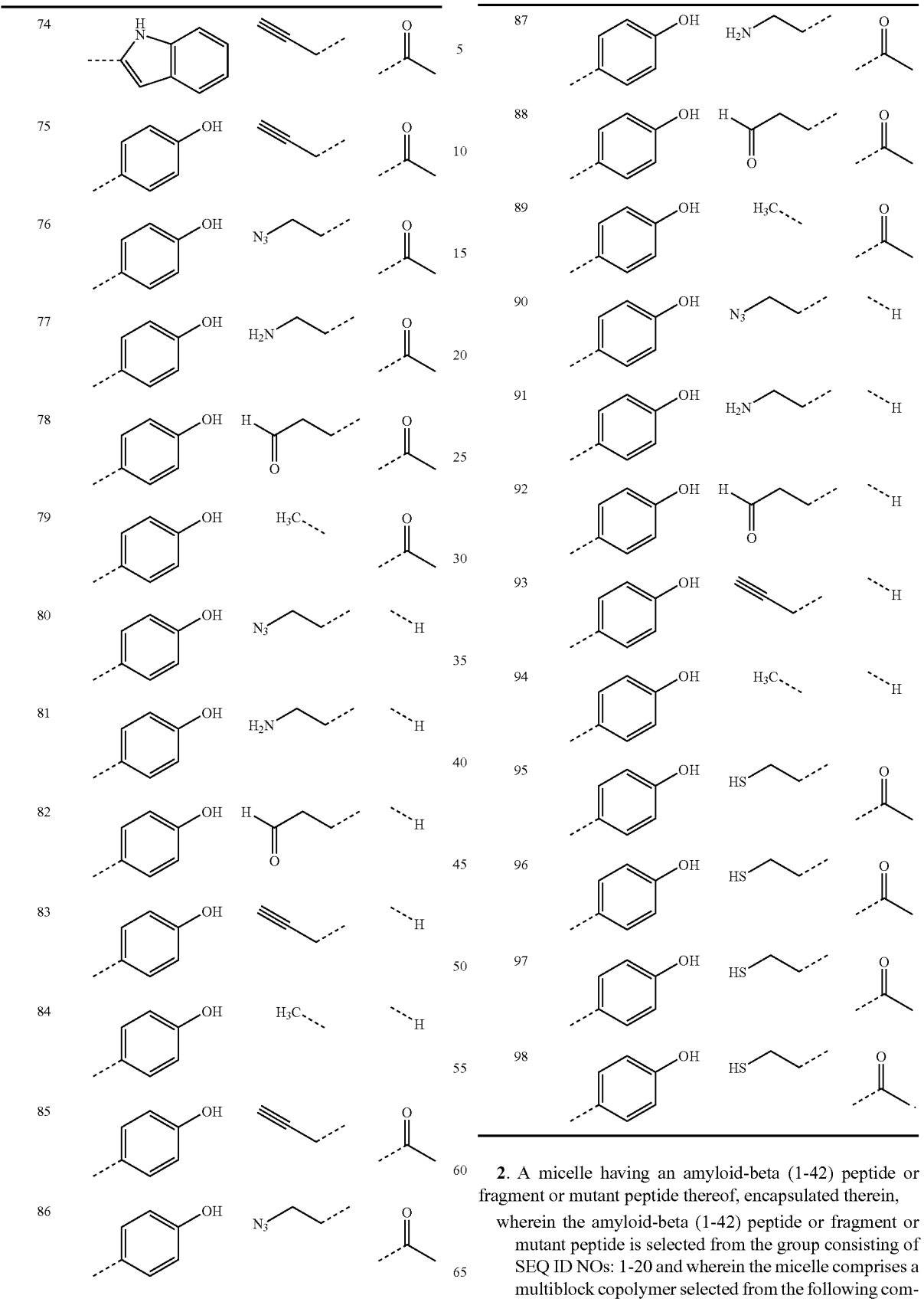
2. A micelle having an amyloid-beta (1-42) peptide or fragment or mutant peptide thereof, encapsulated therein, wherein the amyloid-beta (1-42) peptide or fragment or mutant peptide is selected from the group consisting of SEQ ID NOs: 1-20 and wherein the micelle comprises a multiblock copolymer selected from the following compounds of the formula:

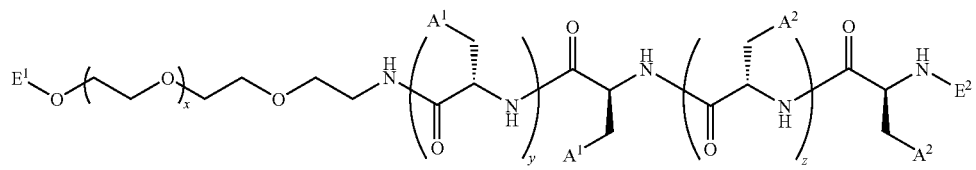

wherein each x is 100-500, each y is 4-20, each z is 5-50, and each dotted bond represents the point of attachment to the rest of the molecule:

| Compound | A¹ | A² | E¹ | E² |
|---|---|---|---|---|
| 99 | –C(O)OH | phenyl | propargyl | acetyl |
| 100 | –C(O)OH | benzyl ester | propargyl | acetyl |
| 101 | –C(O)OH | benzyl ester (CH₂) | propargyl | acetyl |
| 102 | –C(O)OH | propylamine | propargyl | acetyl |
| 103 | –C(O)OH | imidazole | propargyl | acetyl |
| 104 | –C(O)OH | indole | propargyl | acetyl |
| 105 | –CH₂C(O)OH | phenyl | propargyl | acetyl |
| 106 | –CH₂C(O)OH | benzyl ester | propargyl | acetyl |
| 107 | –CH₂C(O)OH | benzyl ester (CH₂) | propargyl | acetyl |

-continued

| Compound | A¹ | A² | E¹ | E² |
|---|---|---|---|---|
| 108 | -CH₂-C(=O)OH | -(CH₂)₃-NH₂ | -C≡CH | -C(=O)CH₃ |
| 109 | -CH₂-C(=O)OH | 1H-imidazol-4-yl | -C≡CH | -C(=O)CH₃ |
| 110 | -CH₂-C(=O)OH | 1H-indol-2-yl | -C≡CH | -C(=O)CH₃ |
| 111 | -SH | phenyl | -C≡CH | -C(=O)CH₃ |
| 112 | -SH | -C(=O)-O-CH₂-C₆H₅ | -C≡CH | -C(=O)CH₃ |
| 113 | -SH | -CH₂-C(=O)-O-CH₂-C₆H₅ | -C≡CH | -C(=O)CH₃ |
| 114 | -SH | -(CH₂)₃-NH₂ | -C≡CH | -C(=O)CH₃ |
| 115 | -SH | 1H-imidazol-4-yl | -C≡CH | -C(=O)CH₃ |
| 116 | -SH | 1H-indol-2-yl | -C≡CH | -C(=O)CH₃ |
| 117 | -C(=O)OH | phenyl | H₂N-CH₂-CH₂- | -C(=O)CH₃ |
| 118 | -C(=O)OH | -C(=O)-O-CH₂-C₆H₅ | H₂N-CH₂-CH₂- | -C(=O)CH₃ |
| 119 | -C(=O)OH | -CH₂-C(=O)-O-CH₂-C₆H₅ | H₂N-CH₂-CH₂- | -C(=O)CH₃ |

-continued

| Compound | A¹ | A² | E¹ | E² |
|---|---|---|---|---|
| 120 | -COOH | -CH₂CH₂CH₂-NH₂ | H₂N-CH₂CH₂- | -C(=O)CH₃ |
| 121 | -COOH | -(1H-imidazol-4-yl) | H₂N-CH₂CH₂- | -C(=O)CH₃ |
| 122 | -COOH | -(1H-indol-2-yl) | H₂N-CH₂CH₂- | -C(=O)CH₃ |
| 123 | -CH₂COOH | -phenyl | H₂N-CH₂CH₂- | -C(=O)CH₃ |
| 124 | -CH₂COOH | -C(=O)O-CH₂-phenyl | H₂N-CH₂CH₂- | -C(=O)CH₃ |
| 125 | -CH₂COOH | -CH₂C(=O)O-CH₂-phenyl | H₂N-CH₂CH₂- | -C(=O)CH₃ |
| 126 | -CH₂COOH | -CH₂CH₂CH₂-NH₂ | H₂N-CH₂CH₂- | -C(=O)CH₃ |
| 127 | -CH₂COOH | -(1H-imidazol-4-yl) | H₂N-CH₂CH₂- | -C(=O)CH₃ |
| 128 | -CH₂COOH | -(1H-indol-2-yl) | H₂N-CH₂CH₂- | -C(=O)CH₃ |
| 129 | -SH | -phenyl | H₂N-CH₂CH₂- | -C(=O)CH₃ |
| 130 | -SH | -C(=O)O-CH₂-phenyl | H₂N-CH₂CH₂- | -C(=O)CH₃ |
| 131 | -SH | -CH₂C(=O)O-CH₂-phenyl | H₂N-CH₂CH₂- | -C(=O)CH₃ |

-continued

| Compound | A¹ | A² | E¹ | E² |
|---|---|---|---|---|
| 132 | -SH | -(CH₂)₃-NH₂ | H₂N-CH₂CH₂- | -C(O)CH₃ |
| 133 | -SH | -(1H-imidazol-4-yl) | H₂N-CH₂CH₂- | -C(O)CH₃ |
| 134 | -SH | -(1H-indol-2-yl) | H₂N-CH₂CH₂- | -C(O)CH₃ |
| 135 | -COOH | -phenyl | N₃-CH₂CH₂- | -C(O)CH₃ |
| 136 | -COOH | -OC(O)-CH₂-C₆H₅ (benzyl ester) | N₃-CH₂CH₂- | -C(O)CH₃ |
| 137 | -COOH | -CH₂-C(O)O-CH₂-C₆H₅ | N₃-CH₂CH₂- | -C(O)CH₃ |
| 138 | -COOH | -(CH₂)₃-NH₂ | N₃-CH₂CH₂- | -C(O)CH₃ |
| 139 | -COOH | -(1H-imidazol-4-yl) | N₃-CH₂CH₂- | -C(O)CH₃ |
| 140 | -COOH | -(1H-indol-2-yl) | N₃-CH₂CH₂- | -C(O)CH₃ |
| 141 | -CH₂-COOH | -phenyl | N₃-CH₂CH₂- | -C(O)CH₃ |
| 142 | -CH₂-COOH | -OC(O)-CH₂-C₆H₅ | N₃-CH₂CH₂- | -C(O)CH₃ |
| 143 | -CH₂-COOH | -CH₂-C(O)O-CH₂-C₆H₅ | N₃-CH₂CH₂- | -C(O)CH₃ |

| Compound | A¹ | A² | E¹ | E² |
|---|---|---|---|---|
| 144 | -CH₂-COOH | -(CH₂)₃-NH₂ | N₃-CH₂CH₂- | -C(O)CH₃ |
| 145 | -CH₂-COOH | -CH₂-(1H-imidazol-4-yl) | N₃-CH₂CH₂- | -C(O)CH₃ |
| 146 | -CH₂-COOH | -CH₂-(1H-indol-2-yl) | N₃-CH₂CH₂- | -C(O)CH₃ |
| 147 | -SH | -phenyl | N₃-CH₂CH₂- | -C(O)CH₃ |
| 148 | -SH | -C(O)-O-CH₂-phenyl | N₃-CH₂CH₂- | -C(O)CH₃ |
| 149 | -SH | -CH₂-C(O)-O-CH₂-phenyl | N₃-CH₂CH₂- | -C(O)CH₃ |
| 150 | -SH | -(CH₂)₃-NH₂ | N₃-CH₂CH₂- | -C(O)CH₃ |
| 151 | -SH | -CH₂-(1H-imidazol-4-yl) | N₃-CH₂CH₂- | -C(O)CH₃ |
| 152 | -SH | -CH₂-(1H-indol-2-yl) | N₃-CH₂CH₂- | -C(O)CH₃ |
| 153 | -CH₂-(1H-imidazol-4-yl) | -phenyl | HC≡C-CH₂- | -C(O)CH₃ |
| 154 | -CH₂-(1H-imidazol-4-yl) | -C(=CH₂)-O-CH₂-phenyl | HC≡C-CH₂- | -C(O)CH₃ |
| 155 | -CH₂-(1H-imidazol-4-yl) | -CH₂-C(O)-O-CH₂-phenyl | HC≡C-CH₂- | -C(O)CH₃ |

-continued

| Compound | A¹ | A² | E¹ | E² |
|---|---|---|---|---|
| 156 | imidazole | propylamine | alkyne | acetyl |
| 157 | imidazole | phenyl | N₃-propyl | acetyl |
| 158 | imidazole | benzyl ester (–C(O)O–CH₂–Ph) | N₃-propyl | acetyl |
| 159 | imidazole | benzyl ester (–CH₂C(O)O–CH₂–Ph) | N₃-propyl | acetyl |
| 160 | imidazole | propylamine | N₃-propyl | acetyl |
| 161 | –COOH | phenyl | HS-propyl | acetyl |
| 162 | –COOH | benzyl ester (–C(O)O–CH₂–Ph) | HS-propyl | acetyl |
| 163 | –COOH | benzyl ester (–CH₂C(O)O–CH₂–Ph) | HS-propyl | acetyl |
| 164 | –COOH | propylamine | HS-propyl | acetyl |
| 165 | –COOH | imidazole | HS-propyl | acetyl |
| 166 | –COOH | indole | HS-propyl | acetyl |
| 167 | –CH₂COOH | phenyl | HS-propyl | acetyl |

-continued

| Compound | A¹ | A² | E¹ | E² |
|---|---|---|---|---|
| 168 | –CH₂–COOH | –C(O)O–CH₂–C₆H₅ | HS–CH₂CH₂– | –C(O)CH₃ |
| 169 | –CH₂–COOH | –CH₂–C(O)O–CH₂–C₆H₅ | HS–CH₂CH₂– | –C(O)CH₃ |
| 170 | –CH₂–COOH | –CH₂CH₂–NH₂ | HS–CH₂CH₂– | –C(O)CH₃ |
| 171 | –CH₂–COOH | (1H-imidazol-4-yl) | HS–CH₂CH₂– | –C(O)CH₃ |
| 172 | –CH₂–COOH | (1H-indol-2-yl) | HS–CH₂CH₂– | –C(O)CH₃ |
| 173 | –CH₂CH₂–NH₂ | –C₆H₅ | HS–CH₂CH₂– | –C(O)CH₃ |
| 174 | –CH₂CH₂–NH₂ | –C(O)O–CH₂–C₆H₅ | HS–CH₂CH₂– | –C(O)CH₃ |
| 175 | –CH₂CH₂–NH₂ | –CH₂–C(O)O–CH₂–C₆H₅ | HS–CH₂CH₂– | –C(O)CH₃ |
| 176 | –CH₂CH₂–NH₂ | (1H-imidazol-4-yl) | HS–CH₂CH₂– | –C(O)CH₃ |
| 177 | –CH₂CH₂–NH₂ | (1H-indol-2-yl) | HS–CH₂CH₂– | –C(O)CH₃ |
| 178 | –CH₂CH₂–NH₂ | –C₆H₅ | HC≡C–CH₂– | –C(O)CH₃ |
| 179 | –CH₂CH₂–NH₂ | –C(O)O–CH₂–C₆H₅ | HC≡C–CH₂– | –C(O)CH₃ |

-continued

| Compound | A¹ | A² | E¹ | E² |
|---|---|---|---|---|
| 180 | -CH₂CH₂CH₂-NH₂ | -CH₂-C(=O)-O-CH₂-C₆H₅ | -CH₂-C≡CH | -C(=O)-CH₃ |
| 181 | -CH₂CH₂CH₂-NH₂ | 1H-imidazol-4-yl | -CH₂-C≡CH | -C(=O)-CH₃ |
| 182 | -CH₂CH₂CH₂-NH₂ | 1H-indol-2-yl | -CH₂-C≡CH | -C(=O)-CH₃ |
| 183 | -CH₂CH₂CH₂-NH₂ | phenyl | -CH₂CH₂-N₃ | -C(=O)-CH₃ |
| 184 | -CH₂CH₂CH₂-NH₂ | -C(=O)-O-CH₂-C₆H₅ | -CH₂CH₂-N₃ | -C(=O)-CH₃ |
| 185 | -CH₂CH₂CH₂-NH₂ | -CH₂-C(=O)-O-CH₂-C₆H₅ | -CH₂CH₂-N₃ | -C(=O)-CH₃ |
| 186 | -CH₂CH₂CH₂-NH₂ | 1H-imidazol-4-yl | -CH₂CH₂-N₃ | -C(=O)-CH₃ |
| 187 | -CH₂CH₂CH₂-NH₂ | 1H-indol-2-yl | -CH₂CH₂-N₃ | -C(=O)-CH₃ |
| 188 | -CH₂CH₂CH₂-NH₂ | phenyl | -CH₂CH₂-CHO | -C(=O)-CH₃ |
| 189 | -CH₂CH₂CH₂-NH₂ | -C(=O)-O-CH₂-C₆H₅ | -CH₂CH₂-CHO | -C(=O)-CH₃ |
| 190 | -CH₂CH₂CH₂-NH₂ | -CH₂-C(=O)-O-CH₂-C₆H₅ | -CH₂CH₂-CHO | -C(=O)-CH₃ |
| 191 | -CH₂CH₂CH₂-NH₂ | 1H-imidazol-4-yl | -CH₂CH₂-CHO | -C(=O)-CH₃ |

-continued

| Compound | A¹ | A² | E¹ | E² |
|---|---|---|---|---|
| 192 | ⋯⋯CH₂CH₂CH₂NH₂ | ⋯2-indolyl (NH) | H-CH₂CH₂-C(=O)- (H on top, O on bottom) | -C(=O)CH₃ |

3. A micelle having an amyloid-beta (1-42) peptide or fragment or mutant peptide thereof, encapsulated therein, wherein the amyloid-beta (1-42) peptide or fragment or mutant peptide is selected from the group consisting of SEQ ID NOs: 1-20 and wherein the micelle comprises a multiblock copolymer selected from the following compounds of the formula:

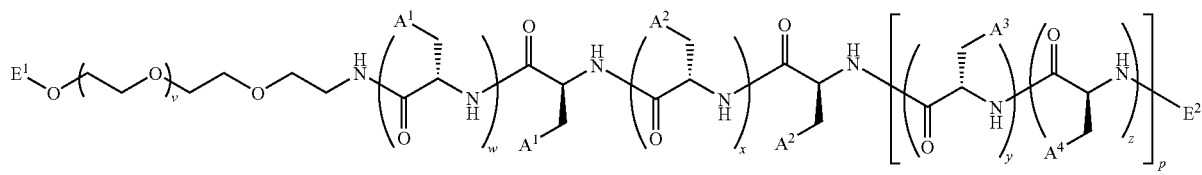

wherein each v is 100-500, each w is 4-20, x is 4-20, each y is 5-50, each z is 5-50, p is the sum of y and z, and each dotted bond represents the point of attachment to the rest of the molecule:

| Compound | A¹ | A² | A³ | A⁴ | E¹ | E² |
|---|---|---|---|---|---|---|
| 193 | -C(=O)OH | -SH | phenyl | 4-hydroxyphenyl | HC≡C-CH₂- | -C(=O)CH₃ |
| 194 | -C(=O)OH | -SH | phenyl | 4-hydroxyphenyl | H₂N-CH₂CH₂- | -C(=O)CH₃ |
| 195 | -C(=O)OH | -SH | phenyl | 4-hydroxyphenyl | N₃-CH₂CH₂- | -C(=O)CH₃ |
| 196 | -C(=O)OH | -SH | phenyl | 4-hydroxyphenyl | H-C(=O)-CH₂CH₂- | -C(=O)CH₃ |
| 197 | -C(=O)OH | -SH | phenyl | 4-hydroxyphenyl | H₃C- | -C(=O)CH₃ |
| 198 | -CH₂-C(=O)OH | -SH | phenyl | 4-hydroxyphenyl | HC≡C-CH₂- | -C(=O)CH₃ |
| 199 | -CH₂-C(=O)OH | -SH | phenyl | 4-hydroxyphenyl | H₂N-CH₂CH₂- | -C(=O)CH₃ |

-continued

| Compound | A$^1$ | A$^2$ | A$^3$ | A$^4$ | E$^1$ | E$^2$ |
|---|---|---|---|---|---|---|
| 200 | -CH$_2$-COOH | -SH | phenyl | 4-hydroxyphenyl | N$_3$-CH$_2$CH$_2$- | -C(O)CH$_3$ |
| 201 | -CH$_2$-COOH | -SH | phenyl | 4-hydroxyphenyl | H-C(O)-CH$_2$CH$_2$- | -C(O)CH$_3$ |
| 202 | -CH$_2$-COOH | -SH | phenyl | 4-hydroxyphenyl | H$_3$C- | -C(O)CH$_3$ |
| 203 | -COOH | -SH | phenyl | 4-hydroxyphenyl | HC≡C-CH$_2$- | -H |
| 204 | -COOH | -SH | phenyl | 4-hydroxyphenyl | H$_2$N-CH$_2$CH$_2$- | -H |
| 205 | -COOH | -SH | phenyl | 4-hydroxyphenyl | N$_3$-CH$_2$CH$_2$- | -H |
| 206 | -COOH | -SH | phenyl | 4-hydroxyphenyl | H-C(O)-CH$_2$CH$_2$- | -H |
| 207 | -COOH | -SH | phenyl | 4-hydroxyphenyl | H$_3$C- | -H |
| 208 | -CH$_2$-COOH | -SH | phenyl | 4-hydroxyphenyl | HC≡C-CH$_2$- | -H |
| 209 | -CH$_2$-COOH | -SH | phenyl | 4-hydroxyphenyl | H$_2$N-CH$_2$CH$_2$- | -H |
| 210 | -CH$_2$-COOH | -SH | phenyl | 4-hydroxyphenyl | N$_3$-CH$_2$CH$_2$- | -H |
| 211 | -CH$_2$-COOH | -SH | phenyl | 4-hydroxyphenyl | H-C(O)-CH$_2$CH$_2$- | -H |
| 212 | -CH$_2$-COOH | -SH | phenyl | 4-hydroxyphenyl | H$_3$C- | -H. |

4. A micelle having an amyloid-beta (1-42) peptide or fragment or mutant peptide thereof, encapsulated therein, wherein the amyloid-beta (1-42) peptide or fragment or mutant peptide is selected from the group consisting of SEQ ID NOs: 1-20 and wherein the micelle comprises a multiblock copolymer selected from the following compounds of the formula:

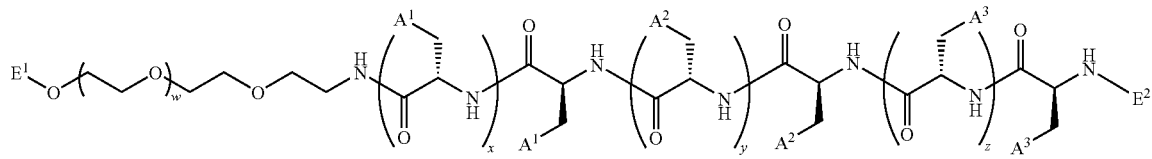

wherein each w is 25-1000, each x is 1-50, y is 1-50, each z is 1-100, and each dotted bond represents the point of attachment to the rest of the molecule:

| Compound | A¹ | A² | A³ | E¹ | E² |
|---|---|---|---|---|---|
| 213 | —C(O)OH | —SH | phenyl | alkynyl | —C(O)CH₃ |
| 214 | —C(O)OH | —SH | 4-hydroxyphenyl | alkynyl | —C(O)CH₃ |
| 215 | —C(O)OH | —SH | —(CH₂)₃NH₂ | alkynyl | —C(O)CH₃ |
| 216 | —C(O)OH | —SH | imidazolyl | alkynyl | —C(O)CH₃ |
| 217 | —C(O)OH | —SH | indolyl | alkynyl | —C(O)CH₃ |
| 218 | —C(O)OH | —SH | —C(O)OCH₂Ph | alkynyl | —C(O)CH₃ |
| 219 | —C(O)OH | —SH | —CH₂C(O)OCH₂Ph | alkynyl | —C(O)CH₃ |
| 220 | —CH(OH)C(O)— | —SH | phenyl | alkynyl | —C(O)CH₃ |
| 221 | —CH(OH)C(O)— | —SH | 4-hydroxyphenyl | alkynyl | —C(O)CH₃ |

| Compound | A¹ | A² | A³ | E¹ | E² |
|---|---|---|---|---|---|
| 222 | CH₂COOH | SH | CH₂CH₂CH₂NH₂ | alkyne | C(O)CH₃ |
| 223 | CH₂COOH | SH | imidazol-4-yl | alkyne | C(O)CH₃ |
| 224 | CH₂COOH | SH | 1H-indol-2-yl | alkyne | C(O)CH₃ |
| 225 | CH₂COOH | SH | OC(O)CH₂-C₆H₅ (benzyl ester) | alkyne | C(O)CH₃ |
| 226 | CH₂COOH | SH | CH₂C(O)O-CH₂-C₆H₅ | alkyne | C(O)CH₃ |
| 227 | COOH | SH | phenyl | alkyne | H |
| 228 | COOH | SH | 4-hydroxyphenyl | alkyne | H |
| 229 | COOH | SH | CH₂CH₂CH₂NH₂ | alkyne | H |
| 230 | COOH | SH | imidazol-4-yl | alkyne | H |
| 231 | COOH | SH | 1H-indol-2-yl | alkyne | H |
| 232 | COOH | SH | OC(O)CH₂-C₆H₅ | alkyne | H |
| 233 | COOH | SH | CH₂C(O)O-CH₂-C₆H₅ | alkyne | H |

-continued

| Compound | A¹ | A² | A³ | E¹ | E² |
|---|---|---|---|---|---|
| 234 | -CH₂-C(=O)OH | -SH | phenyl | -C≡CH (propargyl) | -H |
| 235 | -CH₂-C(=O)OH | -SH | 4-hydroxyphenyl | -C≡CH (propargyl) | -H |
| 236 | -CH₂-C(=O)OH | -SH | -(CH₂)₃-NH₂ | -C≡CH (propargyl) | -H |
| 237 | -CH₂-C(=O)OH | -SH | 1H-imidazol-4-yl | -C≡CH (propargyl) | -H |
| 238 | -CH₂-C(=O)OH | -SH | 1H-indol-2-yl | -C≡CH (propargyl) | -H |
| 239 | -CH₂-C(=O)OH | -SH | -C(=O)-O-CH₂-phenyl | -C≡CH (propargyl) | -H |
| 240 | -CH₂-C(=O)OH | -SH | -CH₂-C(=O)-O-CH₂-phenyl | -C≡CH (propargyl) | -H |
| 241 | -C(=O)OH | -SH | phenyl | -CH₂CH₂-N₃ | -C(=O)-CH₃ |
| 242 | -C(=O)OH | -SH | 4-hydroxyphenyl | -CH₂CH₂-N₃ | -C(=O)-CH₃ |
| 243 | -C(=O)OH | -SH | -(CH₂)₃-NH₂ | -CH₂CH₂-N₃ | -C(=O)-CH₃ |
| 244 | -C(=O)OH | -SH | 1H-imidazol-4-yl | -CH₂CH₂-N₃ | -C(=O)-CH₃ |
| 245 | -C(=O)OH | -SH | 1H-indol-2-yl | -CH₂CH₂-N₃ | -C(=O)-CH₃ |
| 246 | -C(=O)OH | -SH | -C(=O)-O-CH₂-phenyl | -CH₂CH₂-N₃ | -C(=O)-CH₃ |

-continued

| Compound | A¹ | A² | A³ | E¹ | E² |
|---|---|---|---|---|---|
| 247 | -COOH | -SH | -C(=O)O-CH2-C6H5 | N3-CH2CH2- | -C(=O)CH3 |
| 248 | -CH2-COOH | -SH | -C6H5 | N3-CH2CH2- | -C(=O)CH3 |
| 249 | -CH2-COOH | -SH | -C6H4-OH (para) | N3-CH2CH2- | -C(=O)CH3 |
| 250 | -CH2-COOH | -SH | -CH2CH2-NH2 | N3-CH2CH2- | -C(=O)CH3 |
| 251 | -CH2-COOH | -SH | -imidazole | N3-CH2CH2- | -C(=O)CH3 |
| 252 | -CH2-COOH | -SH | -indole | N3-CH2CH2- | -C(=O)CH3 |
| 254 | -CH2-COOH | -SH | -C(=O)O-CH2-C6H5 | N3-CH2CH2- | -C(=O)CH3 |
| 255 | -CH2-COOH | -SH | -CH2-C(=O)O-CH2-C6H5 | N3-CH2CH2- | -C(=O)CH3 |
| 256 | -COOH | -SH | -C6H5 | N3-CH2CH2- | -H |
| 257 | -COOH | -SH | -C6H4-OH (para) | N3-CH2CH2- | -H |
| 258 | -COOH | -SH | -CH2CH2-NH2 | N3-CH2CH2- | -H |
| 259 | -COOH | -SH | -imidazole | N3-CH2CH2- | -H |
| 260 | -COOH | -SH | -indole | N3-CH2CH2- | -H |

-continued

| Compound | A¹ | A² | A³ | E¹ | E² |
|---|---|---|---|---|---|
| 261 | -C(=O)OH | -SH | -C(=O)O-CH₂-C₆H₅ | N₃-CH₂CH₂- | H |
| 262 | -C(=O)OH | -SH | -CH₂-C(=O)O-CH₂-C₆H₅ | N₃-CH₂CH₂- | H |
| 263 | -CH₂-C(=O)OH | -SH | -C₆H₅ | N₃-CH₂CH₂- | H |
| 264 | -CH₂-C(=O)OH | -SH | -C₆H₄-OH (para) | N₃-CH₂CH₂- | H |
| 265 | -CH₂-C(=O)OH | -SH | -CH₂CH₂CH₂-NH₂ | N₃-CH₂CH₂- | H |
| 266 | -CH₂-C(=O)OH | -SH | -(1H-imidazol-4-yl) | N₃-CH₂CH₂- | H |
| 267 | -CH₂-C(=O)OH | -SH | -(1H-indol-2-yl) | N₃-CH₂CH₂- | H |
| 268 | -CH₂-C(=O)OH | -SH | -C(=O)O-CH₂-C₆H₅ | N₃-CH₂CH₂- | H |
| 269 | -CH₂-C(=O)OH | -SH | -CH₂-C(=O)O-CH₂-C₆H₅ | N₃-CH₂CH₂- | H |
| 270 | -C(=O)OH | -SH | -C₆H₅ | H-C(=O)-CH₂CH₂- | -C(=O)-CH₃ |
| 271 | -C(=O)OH | -SH | -C₆H₄-OH (para) | H-C(=O)-CH₂CH₂- | -C(=O)-CH₃ |
| 272 | -C(=O)OH | -SH | -CH₂CH₂CH₂-NH₂ | H-C(=O)-CH₂CH₂- | -C(=O)-CH₃ |

-continued

| Compound | A¹ | A² | A³ | E¹ | E² |
|---|---|---|---|---|---|
| 273 | -COOH | -SH | imidazol-4-yl | -CH₂CH₂CHO | -C(O)CH₃ |
| 274 | -COOH | -SH | 1H-indol-2-yl | -CH₂CH₂CHO | -C(O)CH₃ |
| 275 | -COOH | -SH | -C(O)O-CH₂-C₆H₅ | -CH₂CH₂CHO | -C(O)CH₃ |
| 276 | -COOH | -SH | -CH₂C(O)O-CH₂-C₆H₅ | -CH₂CH₂CHO | -C(O)CH₃ |
| 277 | -CH₂COOH | -SH | -C₆H₅ | -CH₂CH₂CHO | -C(O)CH₃ |
| 278 | -CH₂COOH | -SH | -C₆H₄-OH | -CH₂CH₂CHO | -C(O)CH₃ |
| 279 | -CH₂COOH | -SH | -CH₂CH₂CH₂NH₂ | -CH₂CH₂CHO | -C(O)CH₃ |
| 280 | -CH₂COOH | -SH | imidazol-4-yl | -CH₂CH₂CHO | -C(O)CH₃ |
| 281 | -CH₂COOH | -SH | 1H-indol-2-yl | -CH₂CH₂CHO | -C(O)CH₃ |
| 282 | -CH₂COOH | -SH | -C(O)O-CH₂-C₆H₅ | -CH₂CH₂CHO | -C(O)CH₃ |
| 283 | -CH₂COOH | -SH | -CH₂C(O)O-CH₂-C₆H₅ | -CH₂CH₂CHO | -C(O)CH₃ |
| 284 | -COOH | -SH | -C₆H₅ | -CH₂CH₂CHO | -H |

-continued

| Compound | A¹ | A² | A³ | E¹ | E² |
|---|---|---|---|---|---|
| 285 | -COOH | -SH | -C₆H₄-OH (4-hydroxyphenyl) | -CH₂CH₂CHO | -H |
| 286 | -COOH | -SH | -CH₂CH₂CH₂NH₂ | -CH₂CH₂CHO | -H |
| 287 | -COOH | -SH | imidazol-4-yl | -CH₂CH₂CHO | -H |
| 288 | -COOH | -SH | 1H-indol-2-yl | -CH₂CH₂CHO | -H |
| 289 | -COOH | -SH | -C(=O)OCH₂C₆H₅ (benzyl ester) | -CH₂CH₂CHO | -H |
| 290 | -COOH | -SH | -CH₂C(=O)OCH₂C₆H₅ | -CH₂CH₂CHO | -H |
| 291 | -CH₂COOH | -SH | -C₆H₅ (phenyl) | -CH₂CH₂CHO | -H |
| 292 | -CH₂COOH | -SH | -C₆H₄-OH (4-hydroxyphenyl) | -CH₂CH₂CHO | -H |
| 293 | -CH₂COOH | -SH | -CH₂CH₂CH₂NH₂ | -CH₂CH₂CHO | -H |
| 294 | -CH₂COOH | -SH | imidazol-4-yl | -CH₂CH₂CHO | -H |
| 295 | -CH₂COOH | -SH | 1H-indol-2-yl | -CH₂CH₂CHO | -H |
| 296 | -CH₂COOH | -SH | -C(=O)OCH₂C₆H₅ (benzyl ester) | -CH₂CH₂CHO | -H |

-continued

| Compound | A¹ | A² | A³ | E¹ | E² |
|---|---|---|---|---|---|
| 297 | ⋯CH₂COOH | ⋯SH | ⋯CH₂C(O)OCH₂Ph | H(O)CCH₂CH₂⋯ | ⋯H |

5. A micelle having an amyloid-beta (1-42) peptide or fragment or mutant peptide thereof, encapsulated therein, wherein the amyloid-beta (1-42) peptide or fragment or mutant peptide is selected from the group consisting of SEQ ID NOs: 1-20 and wherein the micelle comprises a multiblock copolymer selected from:

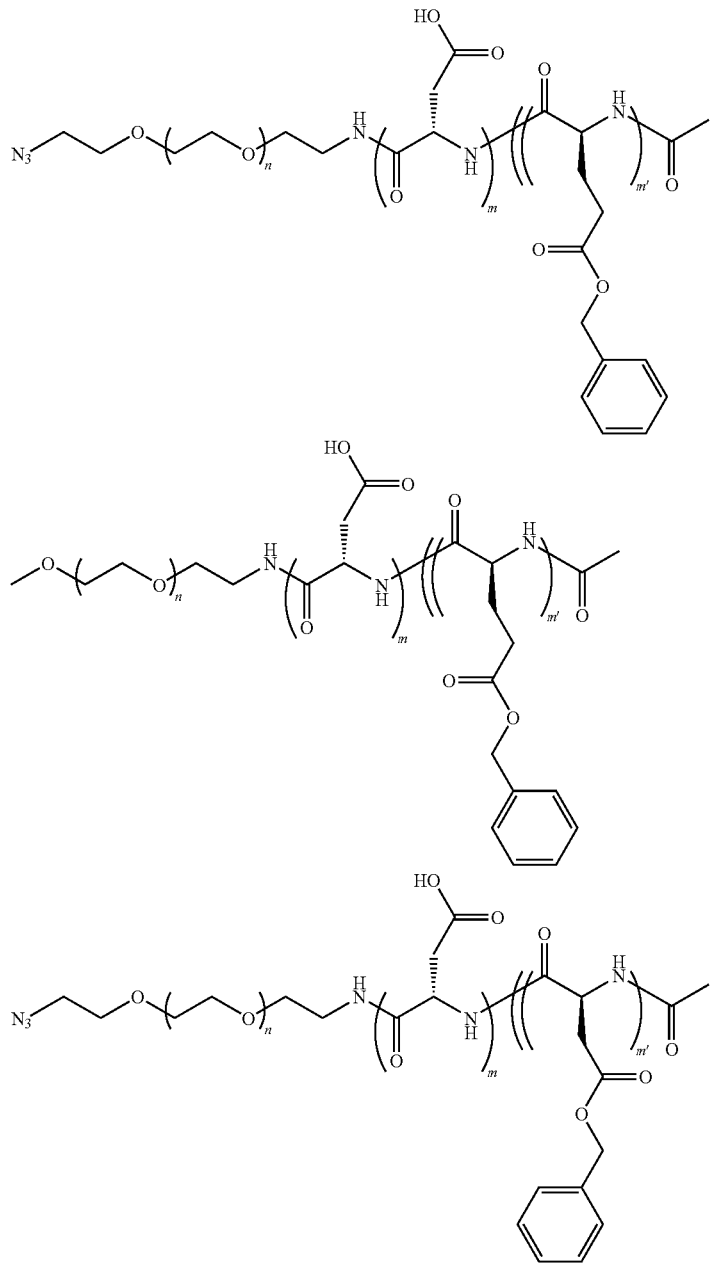

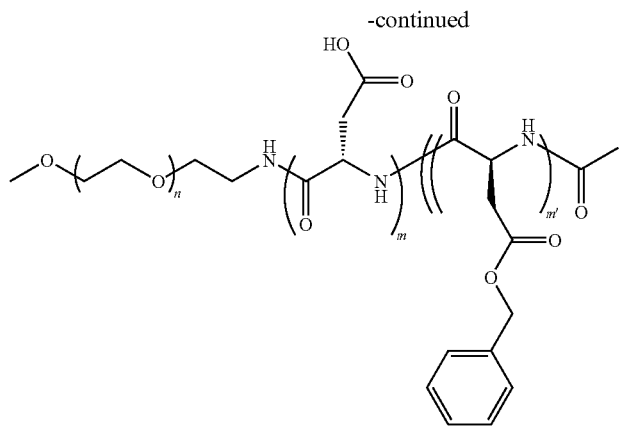
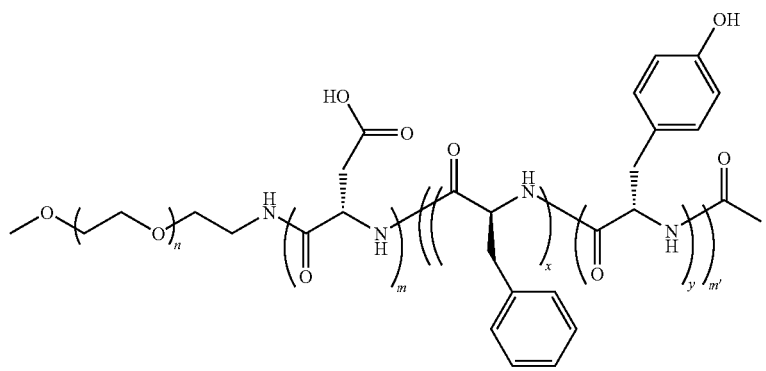
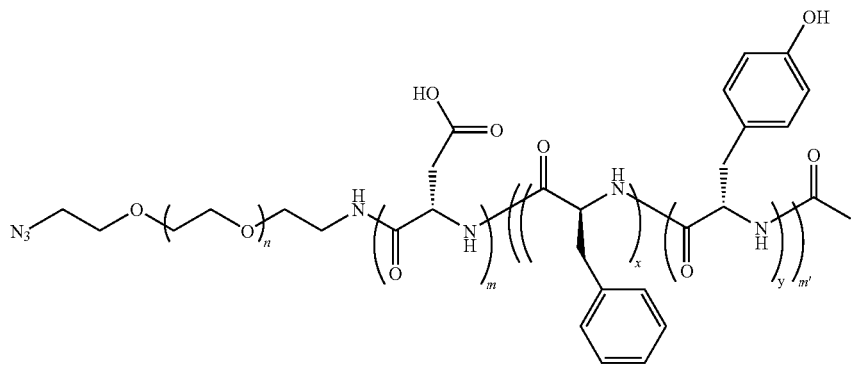
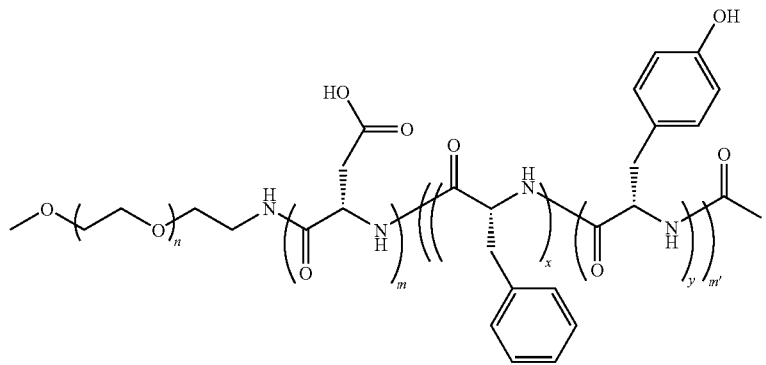

-continued
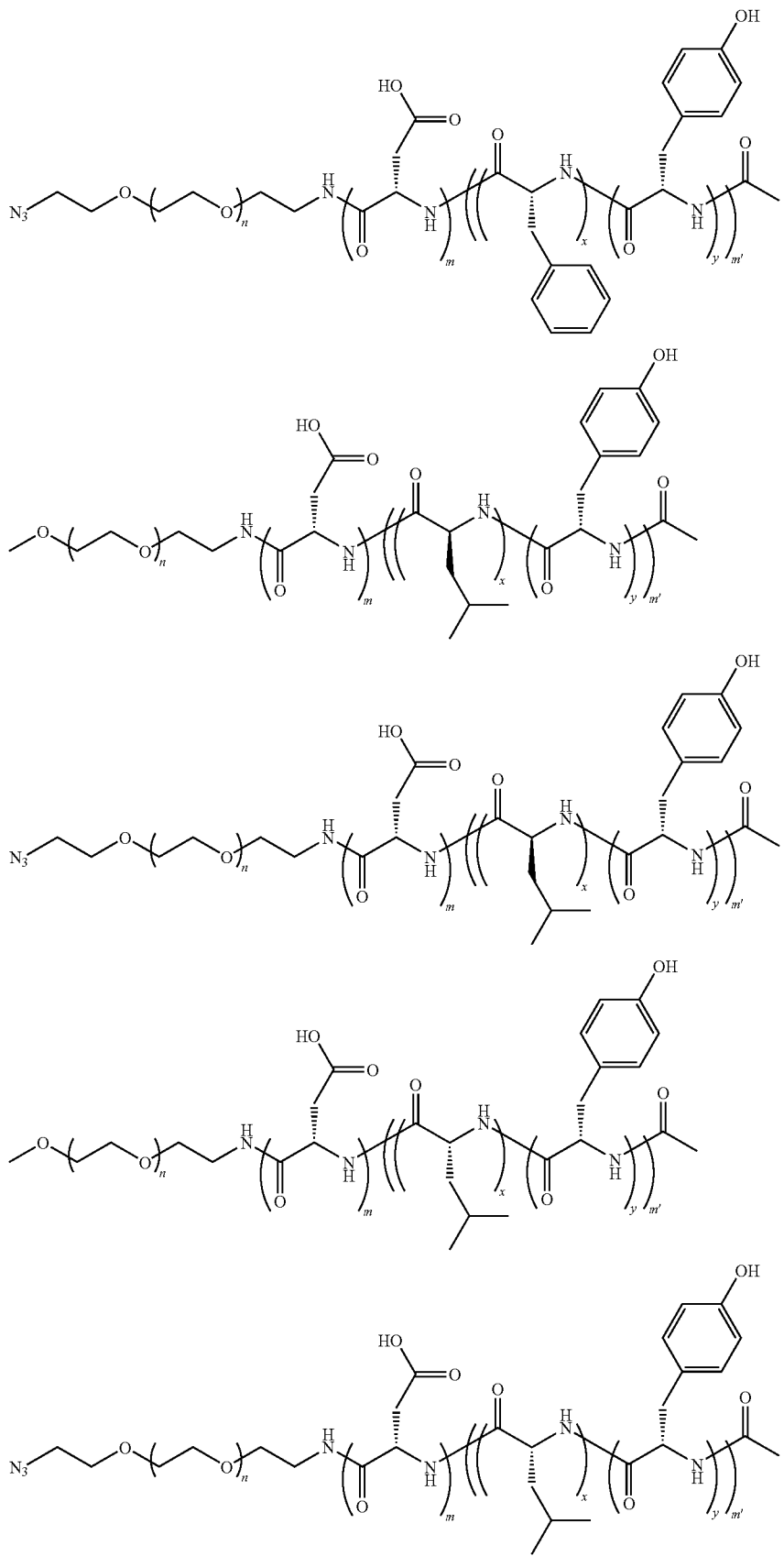

-continued
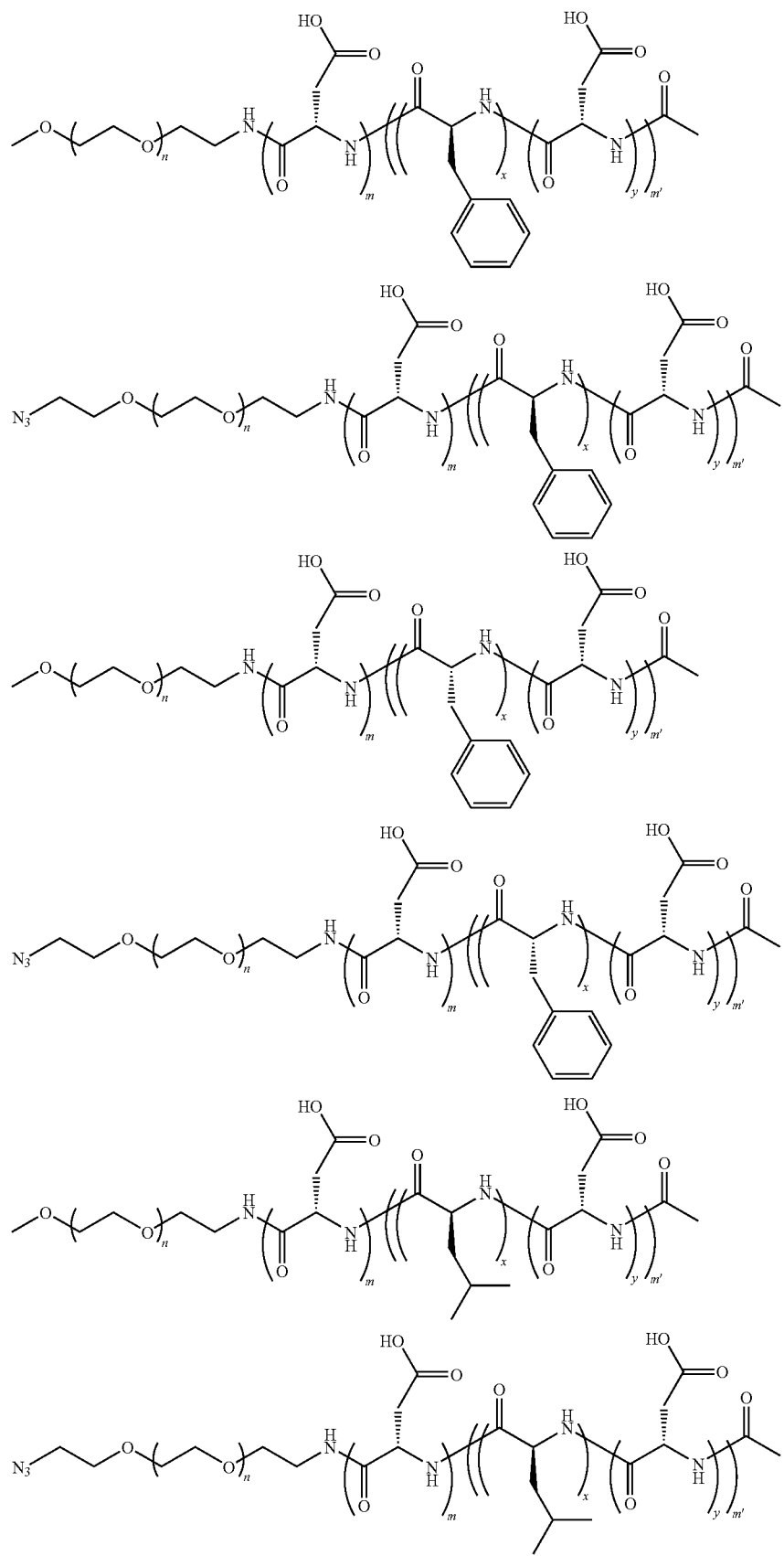

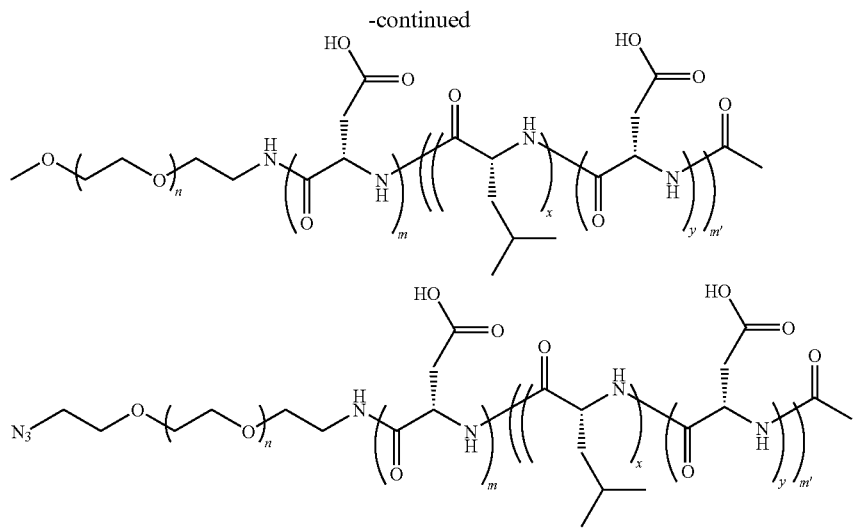

wherein each n is 200-300, each m is 5-15, each x is 1-100, each y is 1-100, and each m' is 20-100 such that x+y =m'.

6. A micelle having an amyloid-beta (1-42) peptide or fragment or mutant peptide thereof, encapsulated therein,
wherein the amyloid-beta (1-42) peptide or fragment or mutant peptide is selected from the group consisting of SEQ ID NOs: 1-20 and wherein the micelle comprises a multiblock copolymer selected from:

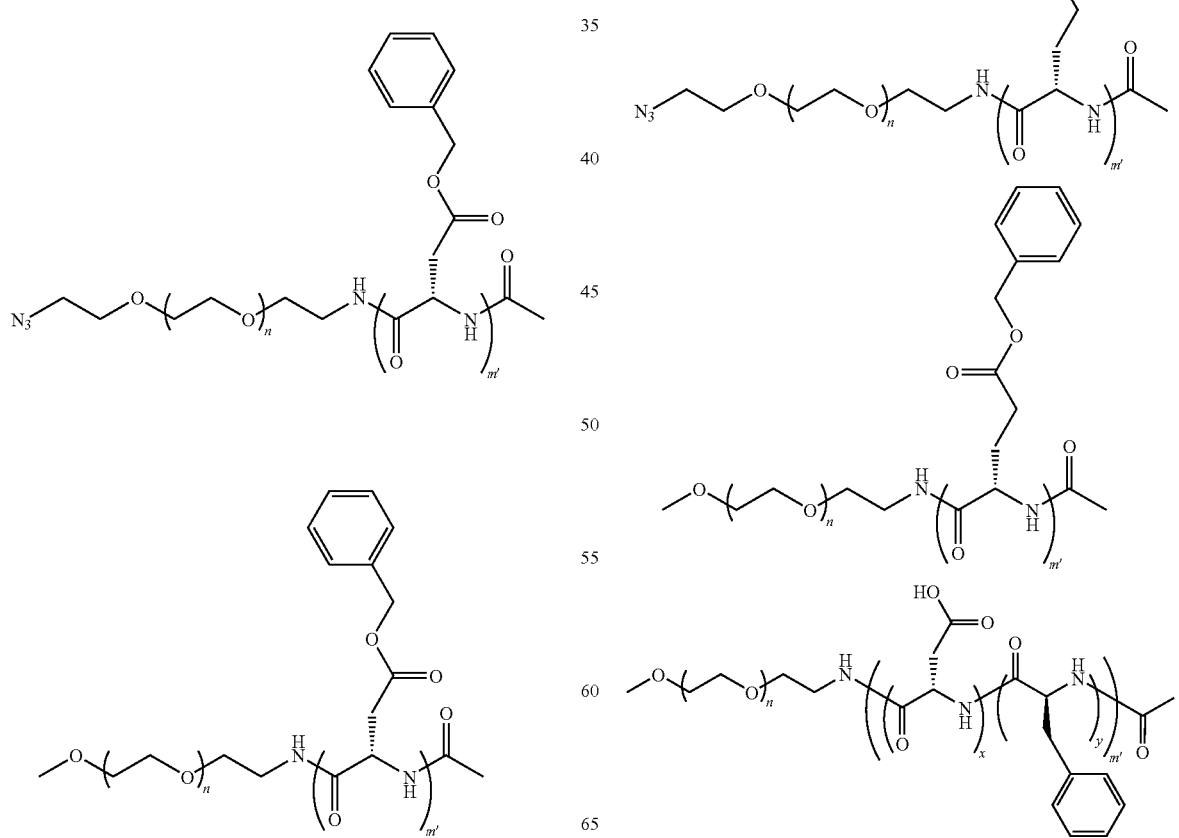

221
-continued
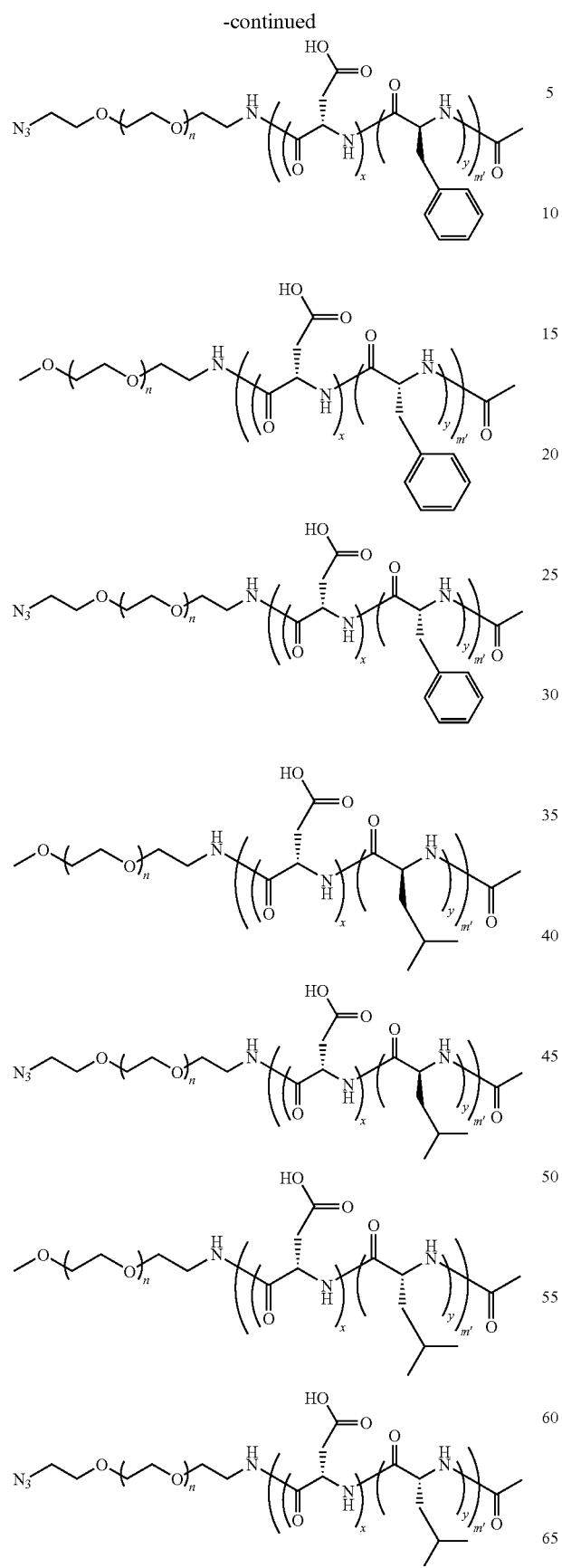
222
-continued
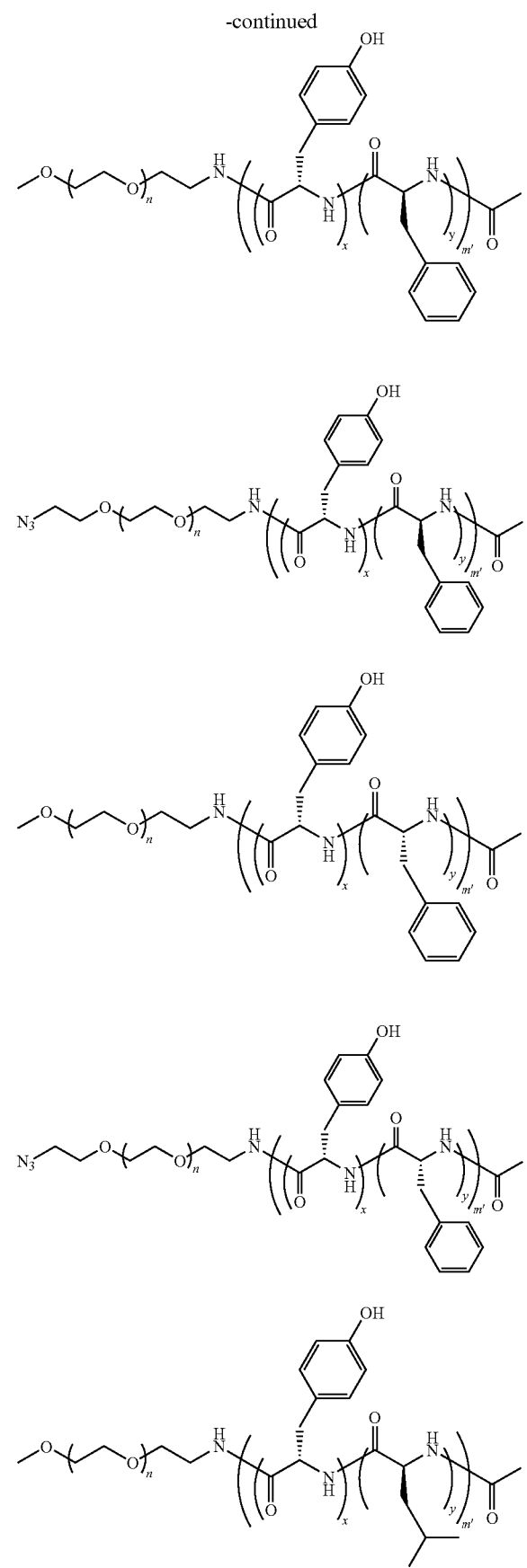

-continued

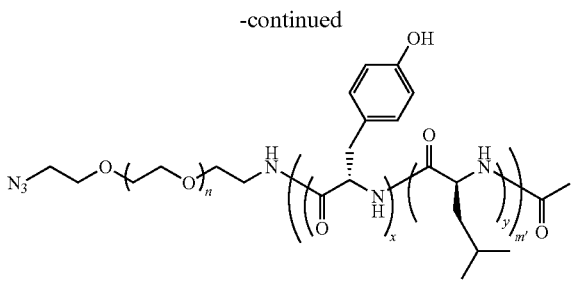

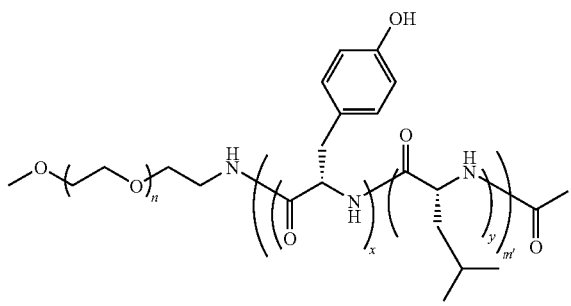

-continued

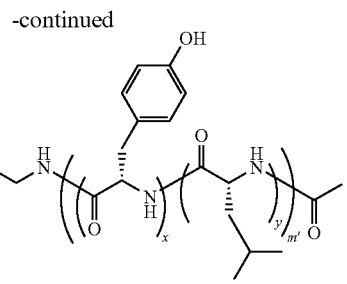

wherein each n is 200-300, each x is 1-100, each y is 1-100, and each m' is 20-100 such that x+y=m'.

7. A composition comprising the micelle according to any one of claims 1-6, and a pharmaceutically acceptable carrier, adjuvant, or vehicle.

8. The micelle according to any one of claims 1-6 having SEQ ID NO: 1 encapsulated therein.

9. The micelle according to any one of claims 1-6, having SEQ ID NO: 2, 3, 4, 5, 6 or 7 encapsulated therein.

10. The micelle according to any one of claims 1-6, having SEQ ID NO: 8, 9, 10, 11, 12, 13, 14, 15, 16, 17, 18, 19 or 20 encapsulated therein.

* * * * *